United States Patent
Crawford et al.

(10) Patent No.: US 11,912,742 B2
(45) Date of Patent: Feb. 27, 2024

(54) HETEROLOGOUS PRODUCTION OF LEUPEPTIN PROTEASE INHIBITORS AND ANALOGS THEREOF

(71) Applicant: YALE UNIVERSITY, New Haven, CT (US)

(72) Inventors: Jason Crawford, Shelton, CT (US); Jhe-Hao Li, New Haven, CT (US); Joonseok Oh, West Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 90 days.

(21) Appl. No.: 17/363,433

(22) Filed: Jun. 30, 2021

(65) Prior Publication Data

US 2022/0002354 A1    Jan. 6, 2022

Related U.S. Application Data

(60) Provisional application No. 63/046,938, filed on Jul. 1, 2020.

(51) Int. Cl.
*C07K 14/195* (2006.01)
*C12N 15/70* (2006.01)

(52) U.S. Cl.
CPC ............ *C07K 14/195* (2013.01); *C12N 15/70* (2013.01)

(58) Field of Classification Search
CPC .................. C07K 14/195; C07K 5/06034; C07K 5/0606; C07K 5/06078; C07K 5/0808; C12N 15/70; C12N 15/52; C12R 2001/19; C12P 13/02; C12P 17/12; C12P 17/182; C12P 21/02
See application file for complete search history.

(56) References Cited

FOREIGN PATENT DOCUMENTS

WO    2016193954 A2 * 12/2016

OTHER PUBLICATIONS

Whisstock et al. Quaterly Reviews of Biophysics, 2003, "Prediction of protein function from protein sequence and structure", 36(3): 307-340. (Year: 2003).*
Witkowski et al. Conversion of a beta-ketoacyl synthase to a malonyl decarboxylase by replacement of the active-site cysteine with glutamine, Biochemistry. Sep. 7, 1999;38(36):11643-50. (Year: 1999).*
Kisselev L., Polypeptide release factors in prokaryotes and eukaryotes: same function, different structure. Structure, 2002, vol. 10:8-9. (Year: 2002).*

* cited by examiner

*Primary Examiner* — Iqbal H Chowdhury
(74) *Attorney, Agent, or Firm* — Saul Ewing LLP; Kathryn Doyle; Domingos J. Silva

(57) ABSTRACT

The present disclosure includes a construct comprising a leupeptin biosynthesis operon, the operon comprising leupA, leupB, leupC, and leupD genes operably linked to a promoter. Also included are cells comprising the construct, and methods for production of leupeptin peptide.

8 Claims, 13 Drawing Sheets

Specification includes a Sequence Listing.

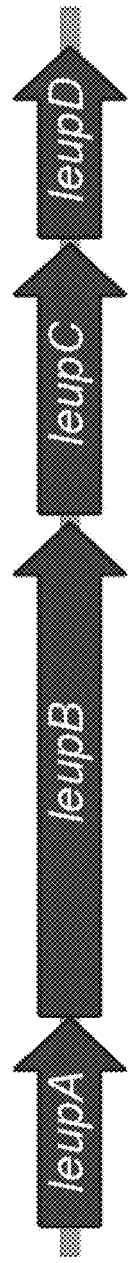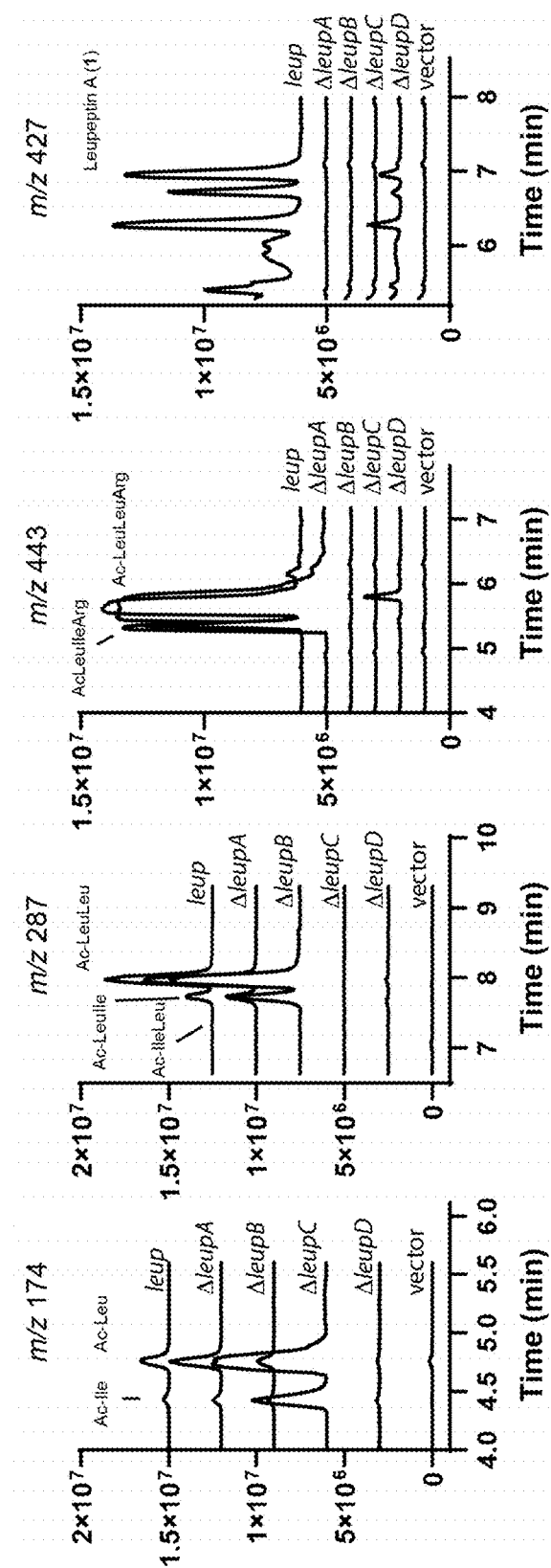
FIG. 1C
FIG. 1D

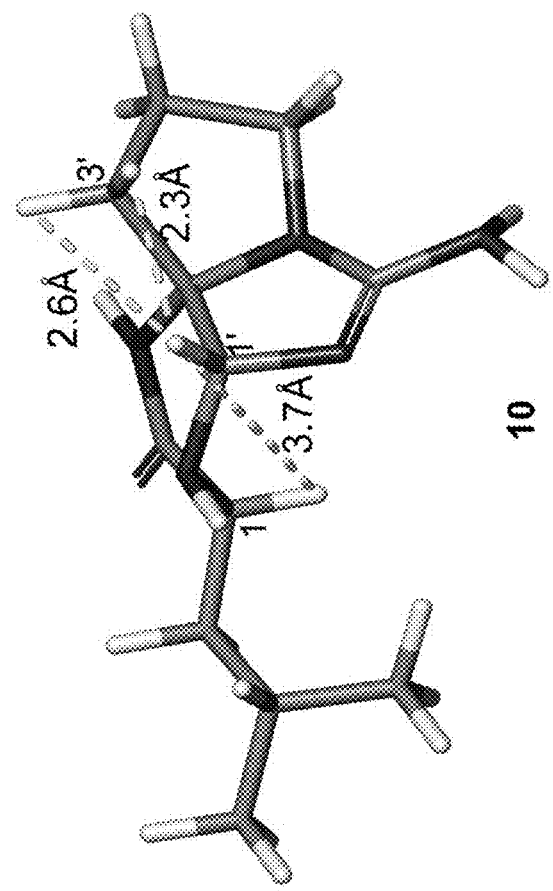
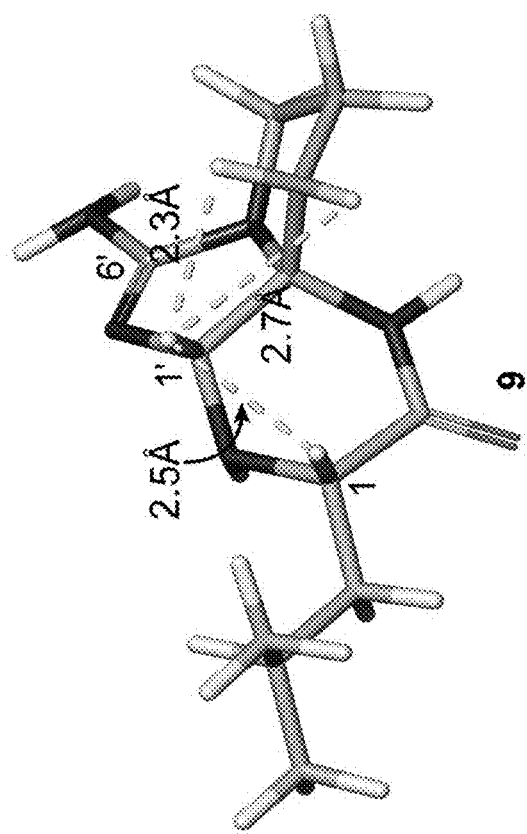
FIG. 3C

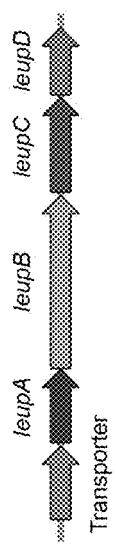

| Strain Name | leupA (a.a. identity) | leupB (a.a. identity) | leupC (a.a. identity) | leupD (a.a. identity) | Putative Transporter | |
|---|---|---|---|---|---|---|
| X. bovienii SS-2004 | XBJ1_0575 D3UWE5 | XBJ1_0574 D3UWE4 | XBJ1_0573 D3UWE3 | XBJ1_0572 D3UWE2 | | |
| X. nematophila ATCC 19061 | XNC1_4602 D3VFV8 (72.6%) | XNC1_4601 D3VFV7 (58.2%) | XNC1_4600 D3VFV6 (59.4%) | XNC1_4599 D3VFV5 (39.7%) | | |
| P. luminescens TT01 | Plu4181 Q7MZU3 (88.3%) | Plu4180 Q7MZU4 (80.8%) | Plu4179 Q7MZU5 (82.3%) | Plu4178 Q7MZU6 (83.3%) | | |
| P. asymbiotica ATCC 43949 | PAU_03811 B6VLC5 (88.6%) | PAU_03810 B6VLC4 (81.8%) | PAU_03809 B6VLC3 (85.3%) | PAU_03808 B6VLC2 (82.3%) | | |
| P. temperata J3 | AXDT_v1_2070002 WP_023045873.1 (88.8%) | AXDT_v1_2070004 ERT11308.1 AXDT_v1_2070003 ERT11307.1 (84.7%) | AXDT_v1_2070005 WP_023045876.1 (84.9%) | AXDT_v1_2070006 WP_023045877.1 (84.2%) | | leupB is split into 2 ORFs |
| K. oxytoca KCTC1686 | KOX_07030 A0A0H3H148 (68.7%) | KOX_07025 A0A0H3H9Z6 (52.9%) | KOX_07020 A0A0H3H3W0 (54.3%) | KOX_07015 A0A0H3H443 (43.9%) | KOX_07035 A0A0H3H648 | |
| C. violaceum ATCC 12472 | CV_4318 Q7NMBD2 (78.7%) | CV_4319 Q7NQ23 (62.8%) | CV_4320 Q7NQ22 (62.7%) | CV_4321 Q7NQ21 (46.9%) | CV_4317 Q7NQ24 | |
| P. fluorescens Pf0-1 | Pfl01_2559 Q3KD55 (61.1%) | Pfl01_2558 Q3KD56 (52.1%) | Pfl01_2557 Q3KD57 (47.3%) | Pfl01_2556 Q3KD58 (36.5%) | | |
| P. entomophila L48 | PSEEN0621 Q1IFJ2 (65.5%) | PSEEN0622 Q1IFJ1 (53.1%) | PSEEN0623 Q1IFJ0 (49.2%) | PSEEN0624 Q1IFI9 (41.6%) | | |
| B. marinus SJ | BMS_0637 E1X572 (50.5%) | BMS_0638 E1X573 (37.4%) | BMS_0639 E1X574 (35.3%) | BMS_0636 E1X571 (27.0%) | | Also known as Halobacteriovorax marinus ATCC BAA-682 |
| S. cattleya ATCC 35852 | SCATT_p03720 G8XFJ5 (54.4%) | SCATT_p03730 F8JK72 (39.0%) | SCATT_p03690 F8JK76 (37.3%) | SCATT_p03710 F8JK74 (29.2%) | SCATT_p03700 F8JK75 | |
| S. collinus Tu 365 | B446_33045 S5V9T0 (53.3%) | B446_33040 S5VRQ3 (41.8%) | B446_33060 S5V6W8 (37.3%) | B446_33050 S5VE08 (27.0%) | B446_33055 S5VFT5 | |
| S. albulus CCRC 11814 | AROYv1_890085 WP_016577536.1 (54.5%) | AROYv1_890086 WP_020930524.1 (37.8%) | AROYv1_890082 WP_037635192.1 (36.4%) | AROYv1_890084 WP_020930523.1 (25.7%) | AROYv1_890083 WP_016577180.1 | |
| S. roseochromogenus subsp. oscitans | AWQX_v1_3860017 WP_023553530.1 (53.6%) | AWQX_v1_3860016 WP_023553529.1 (41.2%) | AWQX_v1_3860020 WP_031227262.1 (37.8%) | AWQX_v1_3860018 WP_023553531.1 (29.2%) | AWQX_v1_3860019 WP_078630522.1 | |
| S. purpureus KA281 | ARAD_v1_170630 WP_019891210.1 (53.6%) | ARAD_v1_170631 WP_106960040.1 (39.2%) | ARAD_v1_170627 WP_019891207.1 (39.9%) | ARAD_v1_170629 WP_019891209.1 (30.2%) | ARAD_v1_170628 WP_019891208.1 | |

FIG. 5

HETEROLOGOUS PRODUCTION OF LEUPEPTIN PROTEASE INHIBITORS AND ANALOGS THEREOF

CROSS-REFERENCE TO RELATED APPLICATIONS

The present application is entitled to priority un 35 U.S.C. § 119(e) to U.S. Provisional Patent Application No. 63/046,938, filed Jul. 1, 2020, which is hereby incorporated in its entirety herein.

STATEMENT REGARDING FEDERALLY SPONSORED RESEARCH OR DEVELOPMENT

This invention was made with government support under CA186575 and GM097096 awarded by National Institutes of Health. The government has certain rights in the invention.

SEQUENCE LISTING

The ASCII text filed named "047162-7289US1_Sequence Listing" created on Jun. 25, 2021, comprising 24 KB, is hereby incorporated by reference in its entirety.

BACKGROUND OF THE DISCLOSURE

Protease inhibitors are important molecules in medical use, pharmaceutical manufacturing, and biomedical research. Many antiviral and antitumor drugs are protease inhibitors. In particular, leupeptin is the one of the most well-known, broad-spectrum serine/cysteine protease inhibitors that is used worldwide for protein purification workflows.

Leupeptin is a tripeptide aldehyde (N-Acetyl-L-leucyl-L-leucyl-L-argininal, also known as Ac-Leu-Leu-Arg-H) isolated from several *Streptomyces* species that inhibits trypsin-like proteases. Leupeptin is known to inhibit a wide spectrum of mammalian lysosomal hydrolases and serves as a model inhibitor in autophagy research. Leupeptin also prevents aminoglycoside ototoxicity by inhibiting calpain protease activity. The tripeptide aldehyde moiety also inspired synthetic structure-function studies of leupeptin analogues and showed variable inhibitory activities against other proteases.

Although leupeptin is a well-known natural product, its biosynthesis origin has remained unknown for decades. In addition, the market still relies significantly on microbial fermentation from *Streptomyces* producers for its production.

A need exists in the art for methods and platforms for rapid, efficient, and large-scale production of leupeptin and analogues thereof. The present disclosure addresses this need.

SUMMARY OF THE INVENTION

As described herein, the present invention relates to a construct comprising a leupeptin biosynthesis operon, the operon comprising leupA, leupB, leupC, and leupD genes operably linked to a promoter. Also included are cells comprising the construct, and methods for production of leupeptin peptide.

As such, in one aspect, the invention provides a construct comprising a leupeptin biosynthesis operon, the operon comprising leupA, leupB, leupC, and leupD genes operably linked to one or more promoters.

In certain embodiments, the leupeptin biosynthesis operon is derived from a gammaproteobacteria.

In certain embodiments, the gammaproteobacteria is selected from group consisting of a *Xenorhabdus*, a *Photorhabdus*, and a *Klebsiella*.

In various embodiments of the above aspect or any other aspect of the invention delineated herein, the gammaproteobacteria is selected from the group consisting of *Bacteriovorax marinus, Chromobacterium violaceum, Psuedomonas entomophila, Pseudomonas fluorescens, Klebsiella oxytoca, Xenorhabdus nematophila, Xenorhabdus bovienii, Photorhabdus luminescens, Photorhabdus temperate*, and *Photorhabdus asymbiotica*.

In certain aspects, the construct comprises the nucleic acid sequence of any one of SEQ ID NOs: 1-5.

In another aspect, the invention provides a cell comprising a construct comprising a leupeptin biosynthesis operon, the operon comprising leupA, leupB, leupC, and leupD genes operably linked to a promoter.

In certain embodiments, the leupeptin biosynthesis operon is derived from a gammaproteobacteria.

In certain embodiments, the gammaproteobacteria is selected from group consisting of a *Xenorhabdus*, a *Photorhabdus*, and a *Klebsiella*.

In various embodiments of the above aspects or any other aspect of the invention delineated herein, the gammaproteobacteria is selected from the group consisting of *Bacteriovorax marinus, Chromobacterium violaceum, Psuedomonas entomophila, Pseudomonas fluorescens, Klebsiella oxytoca, Xenorhabdus nematophila, Xenorhabdus bovienii, Photorhabdus luminescens, Photorhabdus temperate*, and *Photorhabdus asymbiotica*.

In certain embodiments, the cell is a bacterial cell.

In certain embodiments, the cell does not comprise an endogenous leupeptin biosynthesis pathway.

In certain embodiments, the construct comprises the nucleic acid sequence of any one of SEQ ID NOs: 1-5.

In another aspect, the invention provides a method of producing a leupeptin peptide, the method comprising contacting a bacterial cell with the construct of any one or more of the aspects or embodiments of the invention delineated herein, culturing the bacterial cell, and isolating the leupeptin peptide produced by the bacterial cell.

In certain embodiments, the bacterial cell is *E. coli*.

In certain embodiments, the construct is heterologous with respect to the bacterial cell.

In another aspect, the invention provides a compound selected from the group consisting of:

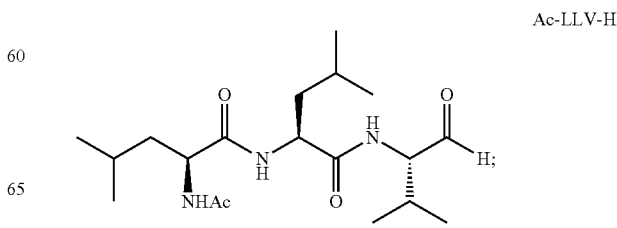

Ac-LLV-H

-continued
Ac-LMR-H
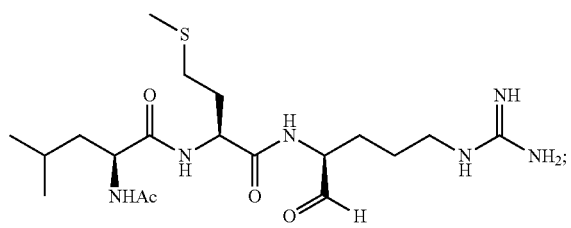
Ac-MLR-H
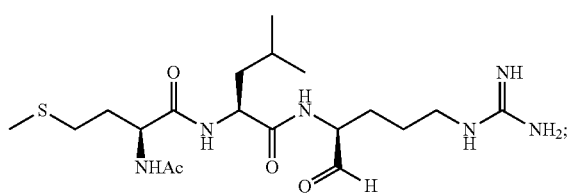
Ac-LMY-H
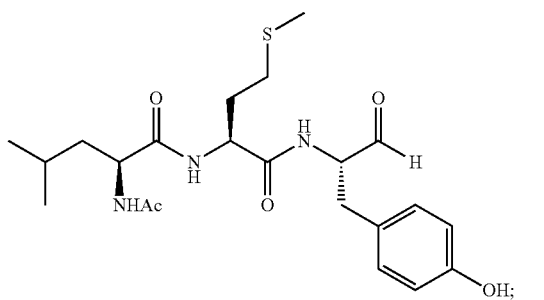
Ac-MLY-H
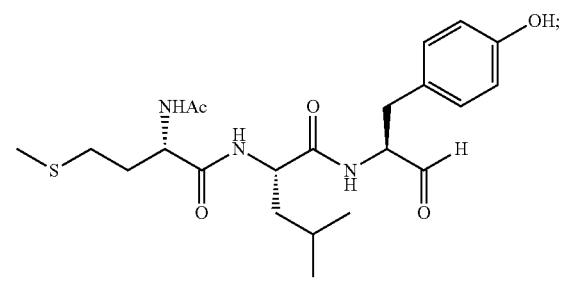
Ac-LMF-H
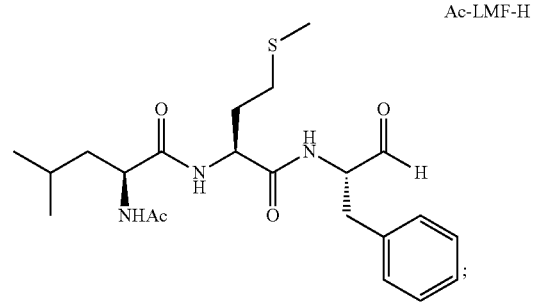
-continued
Ac-MLF-H
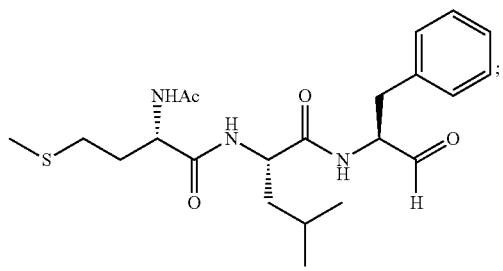
Ac-LMM-H
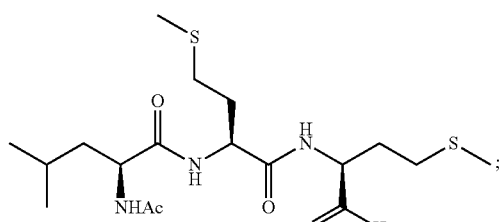
Ac-LFY-H
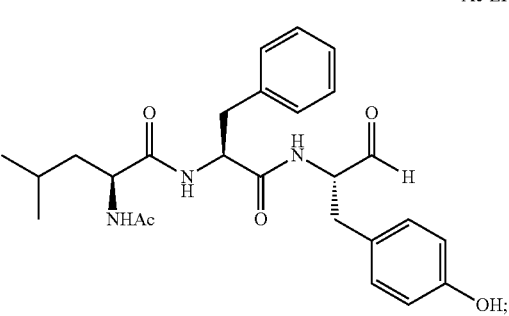
Ac-FLY-H
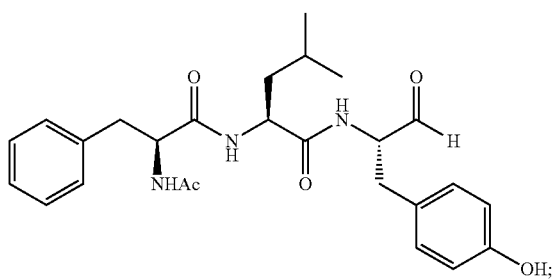
Ac-LFF-H
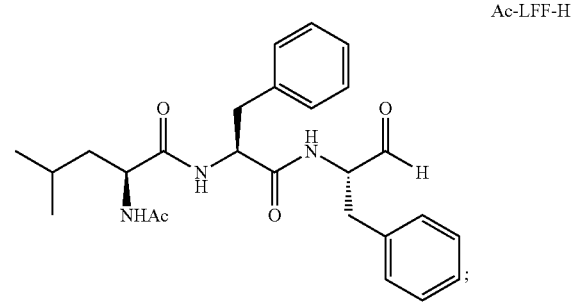

Ac-FLF-H
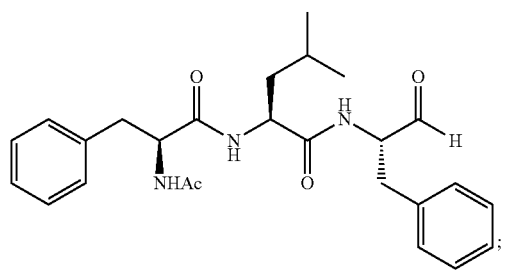
Ac-FMR-H
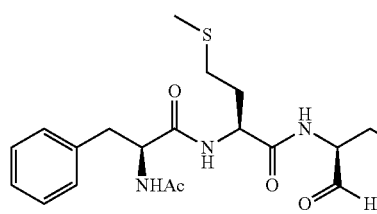
Ac-MFY-H
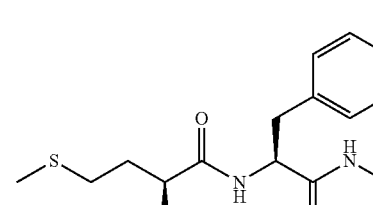
Ac-FMY-H
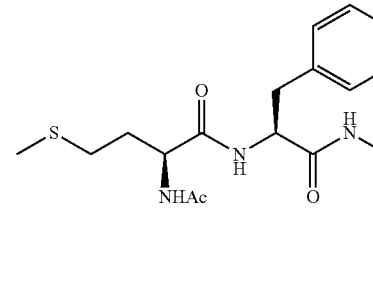
Ac-MFF-H
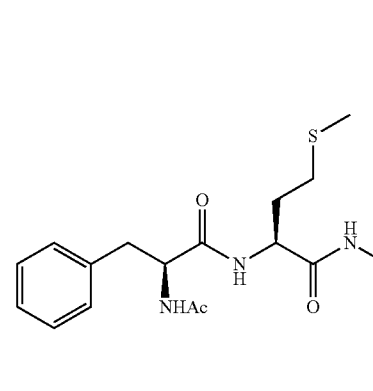
Ac-FMF-H
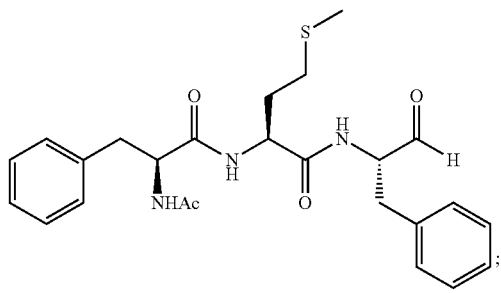
Ac-MMR-H
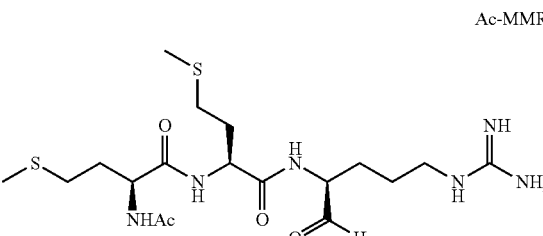
Ac-MMY-H
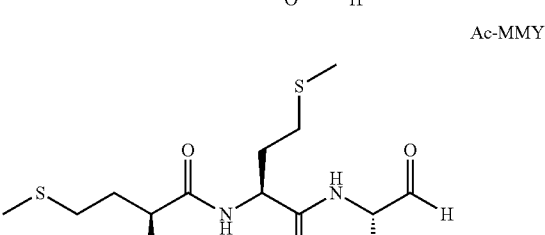
Ac-MMF-H
or a salt, solvate, geometric isomer, or stereoisomer thereof.
In another aspect, the invention provides a compound selected from the group consisting of:
9
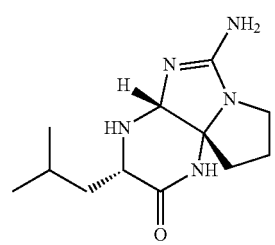

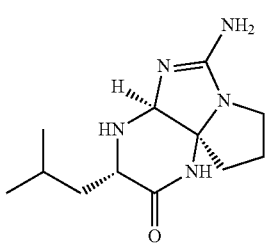

or a salt, solvate, geometric isomer, or stereoisomer thereof.

In another aspect, the invention provides a pharmaceutical composition comprising at least one pharmaceutically acceptable carrier and at least one compound of any one of the aspects or embodiments of the invention delineated herein.

BRIEF DESCRIPTION OF THE DRAWINGS

The following detailed description of specific embodiments of the disclosure will be better understood when read in conjunction with the appended drawings. For the purpose of illustrating the disclosure, there are shown in the drawings exemplary embodiments. It should be understood, however, that the disclosure is not limited to the precise arrangements and instrumentalities of the embodiments shown in the drawings.

FIGS. 1A-1D depict leupeptin production and genetic origins in *Photorhabdus* and *Xenorhabdus* species. FIG. 1A. Extracted ion count (EIC) chromatogram (m/z=427.3027; 10 parts per million window) of the leupeptin standard and organic extracts of *Photorhabdus temperata*, *Photorhabdus luminescens*, *Photorhabdus asymbiotica*, *Xenorhabdus nematophila*, and *Xenorhabdus bovienii* versus LB medium control. FIG. 1B. Leupeptin A (1) exists in equilibrium with different species including the hydrate, free aldehyde, and cyclized carbinolamine. Additionally, the arginal moiety is known to undergo racemization. FIG. 1C. Conserved leupeptin BGC (leup) identified in *Photorhabdus* and *Xenorhabdus* species. FIG. 1D. LC-MS analysis of organic extracts derived from *E. coli* BL21 (DE3) expressing the representative *X. bovienii* leup operon, its individual gene deletions, and vector control.

FIG. 2A: Proposed biosynthesis of leupeptin A (1), B (2), C (3), and other pathway-dependent pyrazinones (8-12) including lumizinone A. FIG. 2B: Relative to major leupeptin A (1), minor pathway-dependent tripeptide aldehydes (2, 3, 6a, 6b, 7a, 7b) were derivatized with methoxyamine and their combined EIC chromatograms are shown.

FIGS. 3A-3E metabolites biosynthesized from leupeptin via proteolytic activity of Plu4509. FIG. 3A: Detection of plu4509-regulated metabolites in *P. luminescens*. FIG. 3B: Structures and key NMR correlations of 9-12. FIG. 3C: Relative configurational analysis of 9 and 10 utilizing ROESY calibration. Mechanistic study of compounds generation from leupeptin and synthetic precursor utilizing overexpressed strain harboring plu4509 (FIG. 3D) and purified plu4509 protein (FIG. 3E). *P<0.1, P<0.01, *P<0.001,****P<0.0001, n.d.: not detected. Statistical analysis in FIG. 3C is made based upon comparison with the media group.

FIG. 5 illustrates bioinformatics of leup orthologs. Genes are reported with UniProtKB entry or NCBI accession number. Amino acid identity was calculated by comparison with genes in *X. bovienii* SS-2004.

DETAILED DESCRIPTION OF THE DISCLOSURE

Figure 1A:
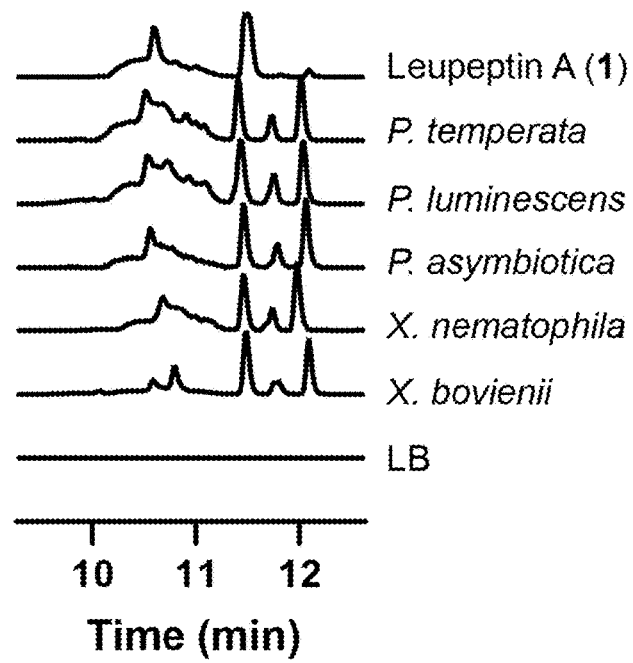

Leupeptin is a bacterial small molecule that is used worldwide as a broad-spectrum serine and cysteine protease inhibitor. However, its biosynthesis and genetic distribution have not been established. A genetic system to heterologously produce leupeptin in other organisms, such as *E. coli*, would be an effective platform for reduced manufacturing costs.

To that end, the current disclosure describes recently decoded and related leupeptin pathways, one of which produces both trypsin-type and chymotrypsin-type protease inhibitors (derived from *Xenorhabdus bovienii*) and one that produces trypsin-type protease inhibitors (derived from *Klebsiella oxytoca*), providing flexibility in the heterologous production of specific protease inhibitor families.

As described herein, a family of leupeptins was identified in gammaproteobacterial pathogens, including *Photorhabdus*, *Xenorhabdus*, and *Klebsiella* species, amongst others. Through genetic, metabolomic, and heterologous expression analyses, their stepwise construction from discretely expressed ligases and accessory enzymes was established. In *Photorhabdus* species, a hypothetical gene required for colonizing infective juvenile nematode hosts was established as a new class of proteases. This enzyme was responsible for cleaving the tripeptide aldehyde protease inhibitors, which led to the formation of "pro-pyrazinones" featuring a novel hetero-tricyclic architecture. Under aerobic conditions, these molecules were transformed into pyrazinones. In *Klebsiella oxytoca*, the pathway was enriched in clinical isolates associated with respiratory tract infections. Thus, without wishing to be limited by any theory, the bacterial production and proteolytic degradation of leupeptins can be associated with animal colonization phenotypes.

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, illustrative materials and methods are described herein. In describing and claiming the present disclosure, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "autologous" is meant to refer to any material derived from the same individual to which it is later to be re-introduced into the individual.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "heterologous" refers to a nucleic acid molecule or sequence that is not normally found in nature or in the cell into which it has been transferred. The term "heterologous" can also refer to the production of a protein or polypeptide by a cell that does not normally produce that protein, or the production of a protein or polypeptide at a level not normally produced by the cell. Production of heterologous proteins can result from the transcription and translation of heterologous nucleic acids by endogenous protein production mechanisms.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the disclosure. The instructional material of the kit of the disclosure may, for example, be affixed to a container which contains the nucleic acid, peptide, and/or composition of the disclosure or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

As used herein, "leupeptin" refers to the compound:

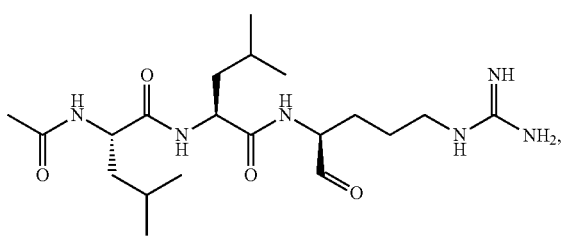 [SMILES: CC(=O)N[C@@H](CC(C)C)C(=O)N[C@@H](CC(C)C)C(=O)N[C@H](C=O)CCCNC(=N)N]

or a salt, solvate, geometric isomer, or stereoisomer thereof.

By the term "modified" or "engineered" as used herein, is meant a changed state or structure of a molecule or cell of the disclosure. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present disclosure, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

A "target site" or "target sequence" refers to a genomic nucleic acid sequence that defines a portion of a nucleic acid to which a binding molecule may specifically bind under conditions sufficient for binding to occur.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure relates in one aspect to the unexpected observation that various bacterial species of the class gammaproteobacteria comprise an operon of four genes, leupA, leupB, leupC, and leupD, which when expressed together enable the biosynthesis of the protease inhibitor leupeptin. Collectively, this operon is known as leup operon. In certain embodiments, the leup operon has been cloned into a construct that is operably linked to one or more promoters, such that a bacterial cell comprising the leup operon construct is able to produce large amounts of leupeptin protein. Also included in the disclosure are bacterial cells comprising the leup operon construct, as well as a method of producing leupeptin protein comprising the culture of bacterial cells comprising the leup operon construct.

Some embodiments of the current disclosure include a construct comprising a leupeptin biosynthesis operon, the expression of which enables the in vivo production of heterologous leupeptin protein. Leupeptin is a protease inhibitor that reversibly inhibits cysteine, serine, and threonine peptidases. Leupeptin is used medically and experimentally as an inhibitor of plasmin, trypsin, papain, kallikrein, and cathepsin B. Leupeptin is a commonly used protease inhibitor in pharmaceutical and biotechnology manufacturing and development, where proteolysis is an undesirable process. Many heterologous protein production methods, including large-scale processes, involve the use of leupeptin or any of its analogs. In the laboratory, leupeptin is routinely used not only to help isolate enzymatic reactions for study, but also neutralize peptidases released during the lysis of cells in protein purification. If left uncontrolled, these cellular proteases can degrade isolated proteins of interest.

In some embodiments, the leup operon-containing construct is derived from a member of the class gammaproteobacteria. In some embodiments, the gammaproteobacteria is of a genus of a *Xenorhabdus*, a *Photorhabdus*, and a *Klebsiella*. In some embodiments, the gammaproteobacteria is at least one of *Bacteriovorax marinus*, *Chromobacterium violaceum*, *Psuedomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperate*, and *Photorhabdus asymbiotica*.

In some embodiments, the disclosure provides a method of producing leupeptin comprising such an expression system comprising a heterologous leup operon expressed in a bacterial cell. In certain embodiments, the method utilizes *E. coli* cells. Because of its importance to industrial-scale bio-manufacturing, bulk quantities of leupeptin are routinely produced. The most common method of manufacture involves the fermentation of large amounts of bacteria of the genus *Streptomyces*, a gram-positive group of Actinobacteria from which leupeptin was first isolated and described in 1969. Fermentation of *Streptomyces* for leupeptin production typically takes a number of days. In one embodiment, the leup operon-containing construct of the disclosure can be transfected into any number of common bacterial species used for large-scale protein production, including *E. coli* and *B. subtilis*, which can result in much faster culturing times.

Molecularly, Leupeptin is characterized by three amino acids and an acyl chain, which can be an acetyl (Leupeptin I or leupeptin PR-LL) or propionyl group or propionyl (Leupeptin II or leupeptin Ac-LL) attached to the N-terminal residue (Leu). Leupeptin's C-terminal group is chemically different from most peptides and proteins, as it has an aldehyde group instead of a carboxyl group. There are two main structural variants of leupeptin: the PR-LL variant, which is active as protease inhibitor, and the Ac-LL variant, which is the most commonly used in industrial applications. Leupeptin analogs are typically characterized by one or both leucine residues being replaced by isoleucine or valine.

Medically, leupeptin has very low toxicity in humans, which makes its therapeutic use possible. Leupeptin is used to modulate intestinal reperfusion, which occurs in cases of shock resulting from burns in the intestinal mucosa and compromising its integrity. Here, the inhibitor prevents enteric bacteria from crossing the luminal wall of the intestine and causing sepsis and/or infecting other parts of the patient. Leupeptin can inhibit acrosin endoprotease of the mammalian sperm cells, and as such can be used as contraceptive. Leupeptin has also been shown to prevent diaphragm contractile dysfunction, which can occur as a side effect of mechanical ventilation. Leupeptin is also used as an inhibitor of lysosomal cysteine proteases.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the disclosure, and, as such, may be considered in making and practicing the disclosure. Particularly useful techniques for particular embodiments will be discussed in the sections that follow.

Compounds

Figure 6:
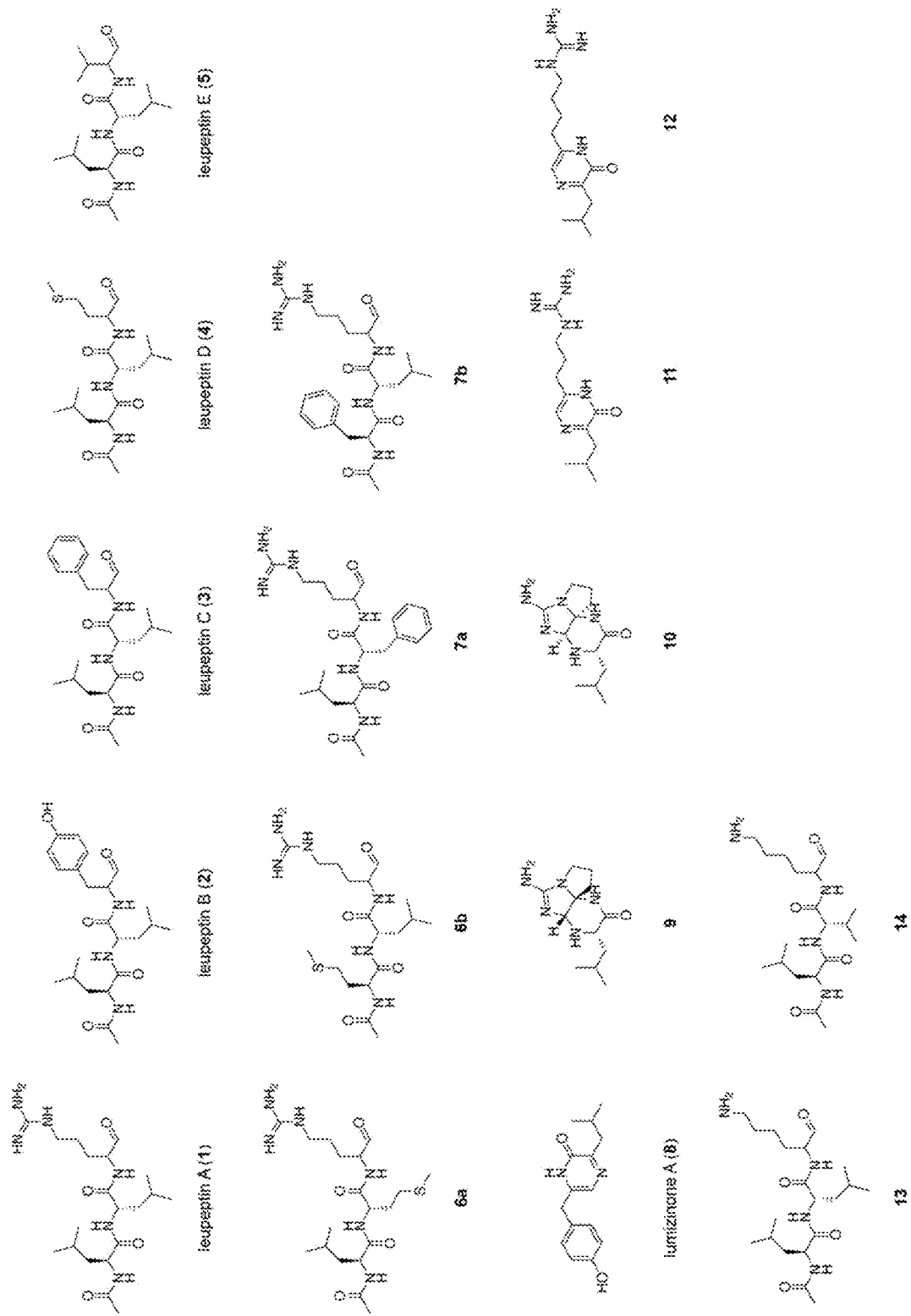
FIG. 6 illustrates certain compounds contemplated within the invention.

The present disclosure provides certain compounds, or a salt, solvate, geometric isomer, or stereoisomer thereof. Certain compounds contemplated in the present disclosure are exemplified in FIG. 6. Certain compounds contemplated in the present disclosure are exemplified in Table 5, which discloses tripeptides, their corresponding aldehydes, and their corresponding oximes.

In certain embodiments, the compound is at least one of:

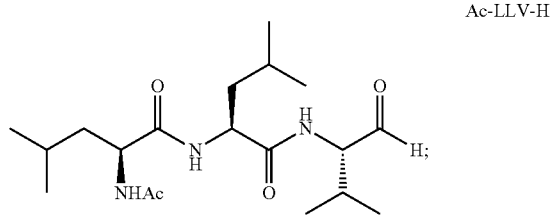

Ac-LLV-H

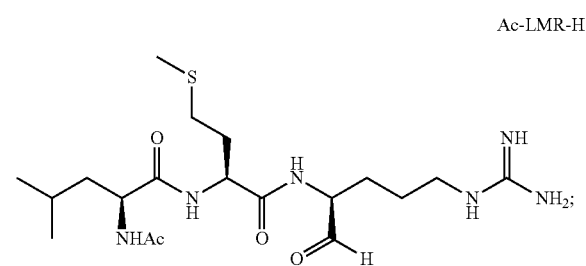

Ac-LMR-H

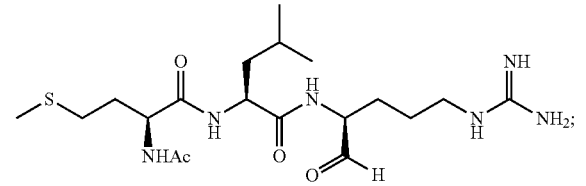

Ac-MLR-H

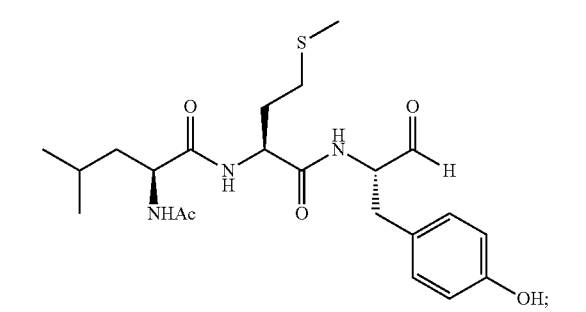

Ac-LMY-H

Ac-MLY-H
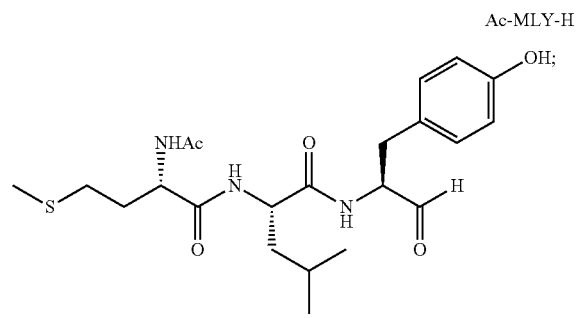
Ac-LMF-H
Ac-MLF-H
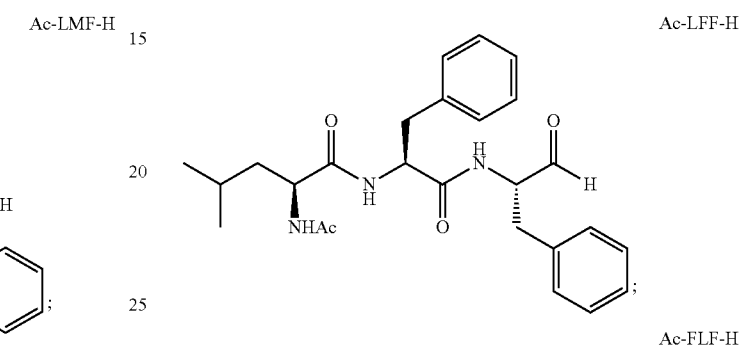
Ac-LMM-H
Ac-LFY-H
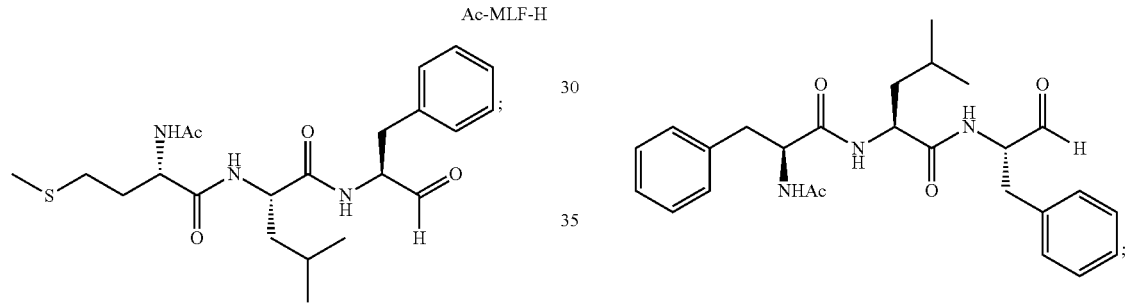
Ac-FLY-H
Ac-LFF-H
Ac-FLF-H
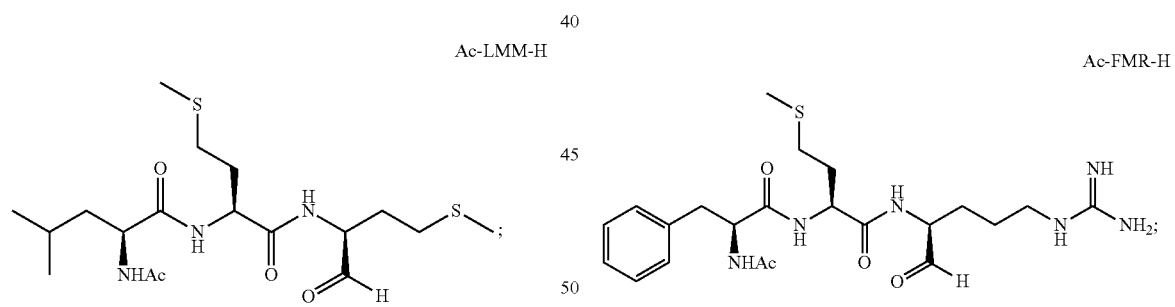
Ac-FMR-H
Ac-MFY-H
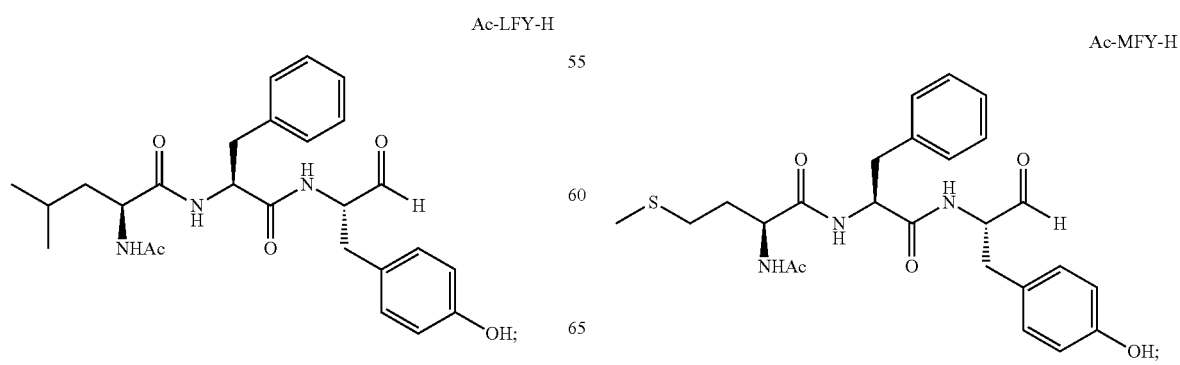

Ac-FMY-H

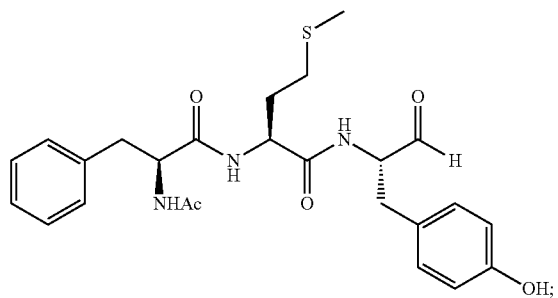

Ac-MFF-H

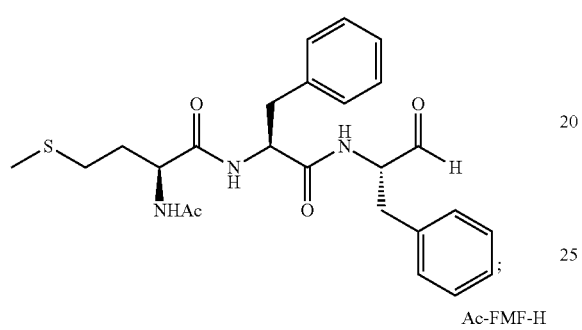

Ac-FMF-H

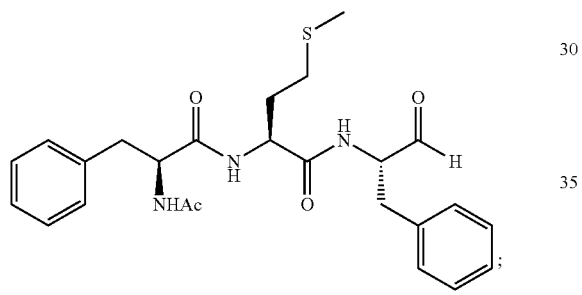

Ac-MMR-H

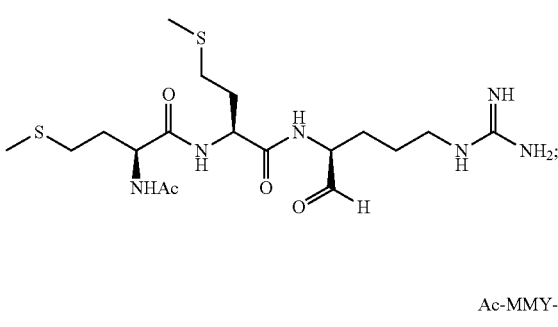

Ac-MMY-H

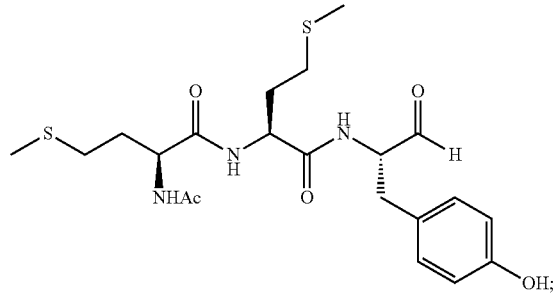

Ac-MMF-H

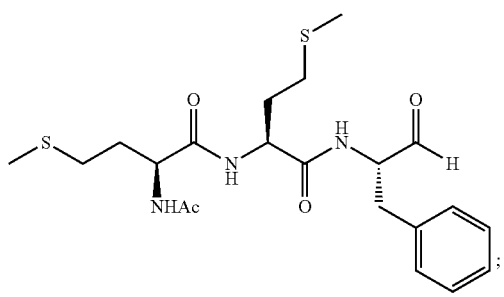

or a salt, solvate, geometric isomer, or stereoisomer thereof.

In certain embodiments, the compound is at least one of:

9

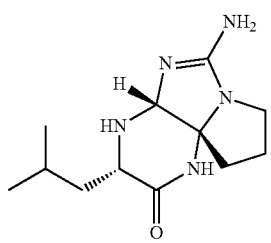

10

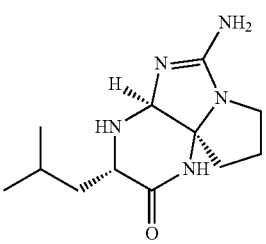

or a salt, solvate, geometric isomer, or stereoisomer thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Pharmaceutical Compositions and Formulations

The disclosure provides pharmaceutical compositions comprising at least one compound of the disclosure or a salt, solvate, geometric isomer, or stereoisomer thereof, which are useful to practice methods of the disclosure. Such a pharmaceutical composition may consist of at least one compound of the disclosure or a salt, solvate, geometric isomer, or stereoisomer thereof, in a form suitable for administration to a subject, or the pharmaceutical composition may comprise at least one compound of the disclosure or a salt, solvate, geometric isomer, or stereoisomer thereof, and one or more pharmaceutically acceptable carriers, one or more additional ingredients, or some combination of these. At least one compound of the disclosure may be present in the pharmaceutical composition in the form of a physiologically acceptable salt, such as in combination with a physiologically acceptable cation or anion, as is well known in the art.

In certain embodiments, the pharmaceutical compositions useful for practicing the method of the disclosure may be administered to deliver a dose of between 1 ng/kg/day and 100 mg/kg/day. In other embodiments, the pharmaceutical compositions useful for practicing the disclosure may be administered to deliver a dose of between 1 ng/kg/day and 1,000 mg/kg/day.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the disclosure may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the disclosure may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the disclosure are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as cattle, pigs, horses, sheep, cats, and dogs.

In certain embodiments, the compositions of the disclosure are formulated using one or more pharmaceutically acceptable excipients or carriers. In certain embodiments, the pharmaceutical compositions of the disclosure comprise a therapeutically effective amount of at least one compound of the disclosure and a pharmaceutically acceptable carrier. Pharmaceutically acceptable carriers, which are useful, include, but are not limited to, glycerol, water, saline, ethanol, recombinant human albumin (e.g., RECOMBUMIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the disclosure may comprise a preservative from about 0.005% to 2.0% by total weight of the composition. The preservative is used to prevent spoilage in the case of exposure to contaminants in the environment. Examples of preservatives useful in accordance with the disclosure include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present disclosure to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the disclosure is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

A medical doctor, e.g., physician or veterinarian, having ordinary skill in the art may readily determine and prescribe the effective amount of the pharmaceutical composition required. For example, the physician or veterinarian could start doses of the compounds of the disclosure employed in the pharmaceutical composition at levels lower than that required in order to achieve the desired therapeutic effect and gradually increase the dosage until the desired effect is achieved.

In certain embodiments, the compositions of the disclosure are administered to the patient in dosages that range from one to five times per day or more. In other embodiments, the compositions of the disclosure are administered to the patient in range of dosages that include, but are not limited to, once every day, every two days, every three days to once a week, and once every two weeks. It will be readily apparent to one skilled in the art that the frequency of administration of the various combination compositions of the disclosure will vary from subject to subject depending on many factors including, but not limited to, age, disease or disorder to be treated, gender, overall health, and other factors. Thus, the disclosure should not be construed to be limited to any particular dosage regime and the precise dosage and composition to be administered to any patient will be determined by the attending physician taking all other factors about the patient into account.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the disclosure include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the disclosure may contain liposomes. The composition of the liposomes and their use are known in the art (i.e., U.S. Pat. No. 6,323,219).

Additional Administration Forms

Additional dosage forms of this disclosure include dosage forms as described in U.S. Pat. Nos. 6,340,475, 6,488,962, 6,451,808, 5,972,389, 5,582,837, and 5,007,790. Additional dosage forms of this disclosure also include dosage forms as described in U.S. patent applications Nos. 20030147952, 20030104062, 20030104053, 20030044466, 20030039688, and 20020051820. Additional dosage forms of this disclosure also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In certain embodiments of the disclosure, the compounds useful within the disclosure are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the disclosure. Accordingly, all values and ranges encompassed by these values and ranges are meant to be encompassed within the scope of the present disclosure. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present disclosure. However, they are in no way a limitation of the teachings or disclosure of the present disclosure as set forth herein.

EXAMPLES

The disclosure is now described with reference to the following Examples. These Examples are provided for the purpose of illustration only, and the disclosure is not limited to these Examples, but rather encompasses all variations that are evident as a result of the teachings provided herein.

Materials & Methods
General Experimental Procedures:

Proton nuclear magnetic resonance spectra ($^1$H NMR) were recorded on a Bruker 400 MHz (synthetic molecules) at room temperature or on an Agilent 600 MHz NMR spectrometer (natural product isolates) equipped with a cold probe and a 3-mm tube spinner, and the chemical shifts were recorded as δ values (ppm) referenced to solvent residual signals. High-resolution mass spectrometry (HRMS) spectra were obtained using an Agilent iFunnel 6550 quadrupole time-of-flight (QTOF) MS instrument fitted with an electrospray ionization (ESI) source coupled to an Agilent 1290 infinity HPLC system, and a Kinetex 5 μm C18 column (250×4.6 mm) was used for the LC/MS analysis with a water:acetonitrile linear gradient containing 0.1% formic acid at 0.7 mL/min: 10% to 100% in 30 min (general gradient). Targeted tandem MS spectra were acquired with the same instrument. Isolations of metabolites were performed using an Agilent PrepStar high-performance liquid chromatography (HPLC) system and Agilent 1260 Infinity system coupled to an Agilent Polaris $C_{18}$-A 5 μm (250×21.2 mm$^2$) column, a Phenomenex Luna 10 μm $C_{18}$ (250×10.0 mm) semiprep column (Phenomenex, Calif., USA), an Agilent Phenyl-Hexyl 5 μm (250×9.5 mm) column, or a Kinetex 5 μm $C_{18}$ (250×4.6 mm) analytical column. UV/Vis spectra were recorded on an Agilent 1260 Infinity system equipped with a photo diode array (PDA) detector (Agilent Technologies, CA, USA). Flash column chromatography was implemented on Lichroprep reverse phase (RP)-$_{18}$ (40-63 mm, Merck, N.J., USA) or a Biotage-Isolera One (Biotage, Charlotte, N.C., USA) equipped with a Biotage SNAP cartridge (KP-$C_{18}$-HS 120 g). Single quadrupole LC-MS analysis was performed on an Agilent 1260 Infinity system using a Phenomenex Luna $C_{18}$(2) (100 Å) 5 μm (4.6×150 mm) column and a PDA detector, coupled with a quadrupole ESI mass spectrometry instrument (Agilent 6120).

*Photorhabdus* and *Xenorhabdus* Culture Extractions:

For leupeptin-related experiments, *Photorhabdus luminescens* TTO1, *Photorhabdus asymbiotica* ATCC 43949, *Photorhabdus termperata* J3 and *Xenorhabdus bovienii* SS-2004 and *Xenorhabdus nematophila* HGB1320 (Richards & Goodrich-Blair, 2010, Appl. Environ. Microbiol. 76(1):221-229) were inoculated from a single colony into 5 mL LB at 30° C. for 2 days. All confluent cultures were extracted with 6 mL n-butanol, centrifuged to remove cells, and 5 mL of n-butanol extract was dried under reduced pressure and subjected to metabolomics analysis. For Δplu4509-related metabolomics, initial comparative metabolomics was implemented with *P. luminescens* (Plu) wildtype (Plu WT) and *P. luminescens* Δ4509, using previously described procedures (Vizcaino et al., 2014, J Ind Microbiol Biotechnol 41(2):285-299). Luria Bertani (LB) liquid cultures (5 mL) were prepared by inoculating single colonies of WT and Δ4509 bacteria. Upon overnight growth under aerobic conditions (30° C. and 250 rpm), each culture (50 μL) was used as seed cultures to inoculate five replicates of hemolymph-mimetic medium (HMM) or LB medium (Crawford et al., 2010, Curr Biol 20(1):69-74; Park et al., 2016, J. Antibiot. (Tokyo) 69(8):616-621), and the cultures were further incubated using identical cultivation conditions for 2 d. Cultures were centrifuged (14,000 g) and supernatants were incubated with XAD-7 HP resins (20 g/L) for 2 h at 37° C. and 250 rpm for small molecule extraction. The pooled filtered resins were extracted with MeOH (10 mL each) and the extract was filtered and evaporated under reduced pressure to yield the representative metabolic samples of WT and mutant. The crude extracts were subjected to comparative metabolomics procedures (Vizcaino et al., 2014, J Ind Microbiol Biotechnol 41(2):285-299), which led to four unique ions present in WT cultures that were completely or largely abrogated in mutant cultures (9-12, FIGS. 3A-3E).

Cloning of Leup Operon for Heterologous Expression:

gDNA extracted with DNeasy Blood & Tissue Kits (Qiagen) from *Xenorhabdus bovienii* str felitae Moldova was used as the template. Primers were used to amplify the leup operon with NdeI and AvrII cut sites (see Table 1). The amplified DNA and pCDFDuet were digested with NdeI and AvrII at 37° C. for 2 hours, purified with NucleoSpin Gel and PCR Clean-up kit (Takara Bio) and ligated with T4 DNA ligase overnight at 4° C. The ligated product was transformed into *E. coli* DH5α through heat shock, recovered for 1 hour at 37° C. in SOC, and plated on LB agar plates with 50 μg/mL spectinomycin. Colonies were inoculated for plasmid extraction. pCDFDuet-Leup was sequence verified and transformed into *E. coli* BL21 (DE3) for heterologous expression. For knock-out of individual leup genes, corresponding primer pairs (Table 1) with additional restriction site and ribosomal binding site were used to PCR amplify the whole pCDFDuet-Leup plasmid, purified with QIAprep Spin Miniprep Kit (Qiagen) and digested with corresponding restriction enzymes. The digested product was then ligated with T4 DNA ligase overnight at 4° C., and the ligation product was heat shock transformed into *E. coli* DH5α, recovered at 37° C. for 1 hour, and plated on LB agar plates with spectinomycin. Colonies were inoculated for plasmid extraction, and plasmids were sequence verified and transformed to *E. coli* BL21 (DE3) for heterologous expression. The cloning of leup operon from *Klebsiella oxytoca* KCTC 1686 (ATCC 8724) followed the above protocol with corresponding restriction enzymes except the following: the leup operon was PCR amplified from single colony with corresponding primers listed in Table 1.

Bacterial Organic Extractions:

E. coli BL21 (DE3) carrying pCDFDuet-Leup or corresponding knock-out strains were grown overnight at 37° C. with shaking (250 rpm) in LB+100 µg/mL spectinomycin. This overnight culture was diluted 1:200 in fresh LB with 100 µg/mL spectinomycin and cultivated in a 37° C. rotating incubator to reach mid-exponential phase. The cultures were then induced with 100 µM IPTG and further cultivated in a 30° C. rotating incubator overnight. To extract, 6.0 mL of n-butanol was individually added to the cultures. Cultures were shaken vigorously and centrifuged to separate the layers. 5 mL of the top n-butanol layer was transferred to a glass vial and dried under reduced pressure. The dried material was dissolved in 150 µL methanol for LC/MS analysis. For peptide aldehyde labeling, 10 µL of methoxyamine stock solution (680 mM in DMSO) or DMSO control were added to the crude extracts in methanol and reacted at room temperature overnight. The reacted crude extracts were then centrifuged and analyzed by LC/MS. High-resolution mass spectrometry (HRMS) data were acquired with an Agilent iFunnel 6550 QTOF MS with a water:acetonitrile general gradient (described elsewhere herein) or shallow gradient containing 0.1% formic acid at 0.7 mL/min: 0-35 min, 5%-60%; 35-35.5 min, 60%-100%; 35.5-39.5 min, 100%.

Mass Spectrometry Analysis of Ac-Leu and Ac-Ile Intermediates:

E. coli BL21 (DE3) carrying pCDFDuet control vector, pCDFDuet-Leup, or pCDFDuet-ΔleupD were grown overnight at 37° C. in LB+100 µg/mL spectinomycin. Overnight cultures were diluted 1:200 in fresh LB with 100 µg/mL spectinomycin and further grown in a 37° C. rotating incubator to reach mid-exponential phase. The cultures were then induced with 100 µM IPTG and grown in a 30° C. rotating incubator overnight. 5 mL of the top n-butanol layers were transferred to a glass vial and dried under reduced pressure. The dried materials were dissolved in 150 µL methanol for LC/MS analysis. An Agilent 6490 TripleQuad coupled with a Kinetex 1.7 µm $C_{18}$ column (100× 2.1 mm) was used for the LC/MS analysis with water: acetonitrile linear gradient containing 0.1% formic acid at 0.3 mL/min: 5% to 35% in 10 min. The dynamic MRM mode was used to monitor Ac-Leu and Ac-Ile with the following transitions: 174 to 86, CE 10.

Isolation and Characterization of Leupeptin B Oxime Adduct:

X. nematophila HGB1320 was inoculated from a frozen cell stock into six 5 mL LB aliquots and grown for two days at 30° C. and 250 rpm. Six 1 L LB aliquots in 4 L Erlenmeyer flasks were inoculated with the 5 mL of X. nematophila cultures and cultivated at 30° C. under aerobic conditions (220 rpm) for two days. The cultures were centrifuged at 6000×g to remove cell debris and the cleared spent medium was pooled and incubated with AMBERLITE® XAD-7 HP resins at 30° C. for 1 hour. The resin was then washed with deionized water and eluted with 1.2 L methanol. The methanol extract (4.02 g) was dried and resuspended in 200 mL methanol, and 0.5 g of methoxyamine was added and stirred overnight at room temperature. The solvent was evaporated with CELITE® adsorbent, dry-loaded onto a reverse phase $C_{18}$ cartridge (60 g), and fractionated using a BIOTAGE™ instrument with a step gradient of water: acetonitrile as follows: 0%, 20%, 40%, 60%, 80% and 100%. The 80% fraction was fractionated with a semiprep column (flow rate 2.0 mL/min, a linear gradient of water:acetonitrile with 0.1% formic acid, 20% to 45% in 30 min), and fractions 28-30 were collected and purified further on the semiprep column (flow rate 2.0 mL/min, a linear gradient of water:acetonitrile with 0.1% formic acid, 30% to 50% in 40 min). The resulting fraction 28 was then purified using a Phenyl-Hexyl column (flow rate 2.0 mL/min, a linear gradient of water: acetonitrile with 0.1% formic acid, 29% to 30% in 30 min) and an analytical $C_{18}$ column (flow rate 0.7 mL/min, a linear gradient of water:acetonitrile with 0.1% formic acid, 35% to 36% in 30 min) yielding 2.7 mg of a cis/trans mixture of the leupeptin B-oxime adduct as a white solid. The chemical structure was elucidated by tandem MS, 1D and 2D NMR ($^1$H, gCOSY, gHSQCAD, gHMBCAD). See Table 3 for NMR data. HR-MS (m/z): [M+H]$^+$ calcd for $C_{24}H_{38}N_4O_5$, 463.2915; found 463.2906.

Cloning of plu4509 for Heterologous Expression:

Cloning of plu4509 was performed in a similar way as described in the section Cloning of Leup Operon, except P. luminescens TT01 gDNA was used as template, a compatible vector (pACYCDuet-1) was employed, and the primers (Table 1) encoded NdeI and HindIII restriction enzyme sites.

Cultivation and Purification of 9-12:

Large-scale cultivations (60 L in total) with Plu WT were performed to obtain practical amounts of the targeted molecules for further chemical and biological investigations. A seed culture of Plu WT (250 µL each), prepared as described elsewhere herein (Photorhabdus and Xenorhabdus Culture Extractions), was used to inoculate 20×5 mL fresh LB cultures, and these cultures were incubated overnight using identical cultivation conditions. Then, each culture was utilized to inoculate 20×1 L LB cultures, which were grown for 2 d (30° C. and 250 rpm). The larger scale cultivation was centrifuged at 14,000 g (r.t.) for 30 min, and XAD-7 HP resins (20 g/L) were added to the supernatants. The mixtures were incubated for 2 h at 37° C. and 100 rpm and the filtered resins were extracted with MeOH (20 L). The methanol residue was filtered and evaporated under reduced pressure or a nitrogen stream to produce the crude material (~200 g). The crude extract was repeatedly chromatographed over a Biotage SNAP cartridge (KP-$C_{18}$-HS 120 g) with a programmed gradient elution method (0→100% MeOH in water for 1 h) to yield 10 fractions (Fr.1-Fr.10). Each fraction was analyzed using LC-MS to detect compounds 9-12 with regard to their retention times and masses found in the initial metabolomic experiments. The targeted compounds were present in Fr.2, and these fractions were further subjected to preparative RP HPLC equipped with an Agilent Polaris $C_{18}$-A column (5 µm, 21×250 mm; 5→30% MeCN in water with 0.1% TFA for 60 min, 8 mL/min, 1 min automated fraction collection), to generate 60 fractions (Fr.2.1-Fr.2.60). Further LC-MS investigation showed that Frs.2.6-15 contained the targeted entities, leading them to be further purified employing repetitive semi-prep HPLC (Phenomenex Luna $C_{18}$(2); isocratic elution of 5.5% MeCN for 9 and 10, and 7% MeCN for 11 and 12 in water with 0.1% TFA).

Structural Characterization of 9-12:

The structures of purified compounds 9-12 were elucidated utilizing the repertoire of spectroscopic and spectrometric techniques, biomimetic synthetic approaches, and chemical derivatization followed by chromatographic comparison of natural and synthetic controls. The molecular formulas of 9 and 10 were assigned as $C_{12}H_{21}N_5O_O$ based upon their protonated HR-ESI-MS mass of m/z 252.1824 (calcd [M+H]$^+$, m/z 252.1819). Larger scale cultivation of Plu WT led to practical amounts of all targeted compounds for NMR analysis, except for 9. Initial interpretation of the NMR data ($^1$H) suggested that 10 could be a diketopiperazine-type molecule comprised of leucine and arginine; however, multidimensional NMR showed key HMBC crosspeaks from H-1' to C-2' and C-6', from H-3' to C-1', and H-3' to C-1', implying the presence of a novel tricyclic system constructed with piperazine, tetrahydropyrrole, and dihydroimidazole. Other COSY and H2BC spectra supported the structure of 10 as shown in FIGS. 3A-3E. Initially, the structural characterization of minor 9 was stalled due to the mass-limitation, but the process was completed upon its biomimetic synthesis (Synthesis Procedures) followed by LC-MS analysis validating the identical retention time and mass of the synthetic material with natural 9. The full multidimensional NMR of minor 9 revealed that the novel compound is indeed a diastereomer of major 10, presumably varying configurations of the C-1'-C-2' hinge. This assumption was verified utilizing ROESY analysis and interproton distance calibration via integration of ROEs. The absolute configuration was established utilizing the biomimetic synthesis, LC-MS comparisons, and the Marfey's approach (Fujii et al., 1997, Analytical Chemistry 69(16):3346-3352), leading to the full structural characterization as shown in FIGS. 3A-3E. Also, the structural assignment of 10 was confirmed by the chromatographic comparison of natural and synthetic controls.

Feeding Studies and In Vitro Assays of Plu4509:

5 mL LB cultures with 50 µg/mL of chloramphenicol were initiated by inoculation of single colonies harboring plu4509 in pACYCDuet-1 in *E. coli* BL21(DE3) versus empty pACYCDuet-1 vector control cells. The cultivations were incubated overnight (37° C. and 250 rpm), and 50 µL of these cultures were employed to inoculate freshly prepared M9 minimal medium with 50 µg/mL of chloramphenicol. These cultures were incubated (37° C. and 250 rpm) to reach O.D. of 0.5, and IPTG (1 mM) with or without leupeptin (100 µM) was added to the overexpressed and empty vector strains. Then the cultures were incubated at 25° C. for 2 d. The cultivations were processed in a similar fashion described in the aforementioned section Cultivation and purification of 9-12. The Plu4509 enzyme was prepared utilizing a standard N-terminal His$_6$-tagged protein purification protocol.

Briefly, 1 L of terrific broth medium (TB salts; 1.2% tryptone, 2.4% yeast extract, and 0.4% glycerol) supplemented with 50 µg/mL chloramphenicol was inoculated with the overnight culture of plu4509 in *E. coli* BL21(DE3) and was grown (37° C. and 250 rpm) to an O.D. of 1. The culture was cooled on ice, induced with 1 mM IPTG, and incubated at 20° C. for 2 d. The cultures were centrifuged at 10000×g for 20 min at 4° C., and the collected pellet was resuspended in 10 mL of lysis buffer followed by the addition of 1 mg/mL of lysozyme. The mixture was incubated on ice for 30 min and then lysed by sonication. The lysate was clarified via centrifugation at 30000×g at 4° C. for 30 min and eluted over a 10 mL column pre-equilibrated with lysis buffer and Ni-NTA resins agarose (Qiagen). The column was washed with 2 mL of lysis buffer (pH 8, NaH$_2$PO$_4$ 50 mM, NaCl 300 mM, imidazole 10 mM, H$_2$O up to 1 L) and 5 mL of wash buffer (pH 8, imidazole 50 mM, Tris-HCl 100 mM, NaCl 300 mM, 10% glycerol, H$_2$O up to 0.5 L), and the protein was eluted with 3 mL of elution buffer (pH 8, imidazole 250 mM, Tris-HCl 100 mM, NaCl 300 mM, glycerol 10%, H$_2$O up to 0.5 L) (1 mL collection window). Purified protein was concentrated utilizing an Amicon Ultra-15 centrifugal filter unit with a 50 kDa cut-off. Concentrated Plu4509 enzyme (20 µM) was then used for in vitro enzyme assays using leupeptin (100 µM) as a substrate.

Multiplex PCR of *Klebsiella* spp:

For the multiplex PCR screen each primer pair (npsB_f+ npsB_r, gapA_fwd+gapA_rev, leupA+leupB_r) was first validated individually on a subset of strains. For the extended screen, all 6 primers (npsB_f, npsB_r, gapA_fwd, gapA_rev, leupA, leupB_r) were combined in the reaction mixture. Strains positive for leupAB in the multiplex PCR were retested with primers leupA and leupD r to confirm the presence of the whole leup operon (without transporter gene KOX_07035). All PCRs were performed using Taq Polymerase (NEB) according to the manufacturer's recommendations and using annealing temperatures of 59° C.

The results of the experiments are now described.

Figure 1B:
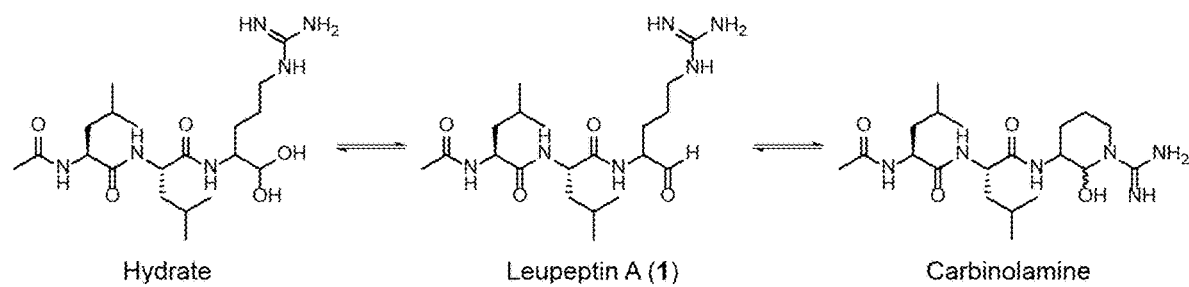

Example 1: Leupeptin Production and Genetic Origins in *Photorhabdus* and *Xenorhabdus* Species Studies of secondary metabolites from bacteria belonging to the *Photorhabdus* genus and the *Xenorhabdus* genus showed that both *Photorhabdus* members (*P. asymbiotica*, *P. luminescens*, and *P. temperata*) and *Xenorhabdus* members (*X. nematophila* and *X. bovienii*) produce the well-known protease inhibitor leupeptin (referred to here as leupeptin A, 1), as established by high-resolution liquid chromatography-mass spectrometry (LC/MS, FIG. 1A). Leupeptin was confirmed by comparison to an authentic standard, which shared identical equilibrium members (aldehyde, hydrate, carbinolamine, FIG. 1B), chromatographic properties, tandem mass spectrometry spectra, and biorthogonal reactivity with hydroxylamine (FIG. 1A). In contrast to previous bioinformatic predictions, a strong candidate NRPS pathway for leupeptin biosynthesis in *Photorhabdus* or *Xenorhabdus* species was not able to be identified.

Consequently, attention turned to candidate ligases that were conserved among the bacteria. A genome synteny analysis was conducted and identified a four-gene cluster (referred to here as the leup operon), encoding two candidate ligases (leupA, leupC), a predicted dual-function reductase-ligase (leupB), and an acetyltransferase (leupD, FIG. 1C). Based on this information, the candidate leup operon was cloned and heterologously expressed it in *E. coli* BL21 (DE3), which led to the leup-dependent production of leupeptin A (FIG. 1D). Thus, a simple heterologous expression strategy was established to access the leupeptins and experimentally confirmed the bioinformatics prediction.

In addition to leupeptin A, the leup operon produced other leupeptin intermediates and isomeric leupeptin analogs in *E. coli*. To support the structures of these related molecules, isotopically labeled $^{13}C_6$-leucine was first fed to leup+ cultures and found the corresponding +6 and +12 masses of leupeptin, as expected from the labeling of one or two of its leucine residues. Labeled intermediates Ac-Leu, Ac-Leu-Leu, and Ac-Leu-Leu-Arg tripeptide (leupeptic acid, carboxylic acid terminus) were also readily detected. Distinct isomeric analogs were also identified in this data that were not labeled with leucine, which was consistent with isoleucine incorporation. The intermediates of these species were confirmed by LC/MS and tandem-MS comparisons to synthetic standards.

While the acetyltransferase and oxidoreductase functionalities were expected, the role of ligases in leupeptin biosynthesis was apparently unexpected. Additionally, the leup operon encodes three ligases, and the order of reactivity cannot be inferred from sequence alone, which is in contrast to many multidomain NRPS systems. To establish the order of ligase reactivity and provide genetic support for leupeptin biosynthesis, the four leupeptin biosynthesis genes were individually deleted. In the acetyltransferase mutant (ΔleupD), a dramatic attenuation of all leupeptin products was observed in lysogeny broth (LB) medium, which supported its expected role in the formation of the Ac-Leu starter substrate (FIG. 1D). Trace amounts of Ac-Leu and Ac-Ile were detected in the vector negative control samples, which was consistent with the dramatic reduction of metabolites observed rather than being a complete loss of function mutant. To avoid potential medium substrate effects, the experiment was also conducted in M9 minimal medium where Ac-Leu and Ac-Ile were undetectable by LC/MS. As expected, the level of Ac-Leu and Ac-Ile were much higher in leup+*E. coli* samples. Additionally, the starter substrates were found at similar levels between the ΔleupD and vector control samples, unexpectedly indicating that *E. coli* also produces these acetyl-amino acid precursors at basal levels. In one ligase mutant (ΔleupC), a complete loss of dipeptides (Ac-Leu-Leu, Ac-Leu-Ile, and Ac-Ile-Leu), tripeptides (Ac-Leu-Leu-Arg and Ac-Leu-Ile-Arg), and leupeptins was observed with the inverse accumulation of starter substrates Ac-Leu and Ac-Ile (FIG. 1D). These results suggest that LeupC is an AMP-ligase responsible for coupling the second amino acid with the Ac-Leu and Ac-Ile substrates. The dual function reductase-ligase LeupB mutant (ΔleupB) accumulated dipeptide and abolished tripeptide formation, suggesting that the ligase functionality of this didomain was responsible for introducing the third amino acid. Finally, the ligase LeupA mutant (ΔleupA) accumulated tripeptides and abolished leupeptin formation. The closest characterized homologs of LeupA are fatty acid ligases, which produce acyl-CoA thioesters. Without wishing to be bound by theory, in certain non-limiting embodiments, LeupA can generate leupeptin-CoA thioester and the oxidoreductase functionality of the LeupB didomain protein can catalyze thioester reduction to release the final aldehyde products. This reductive release strategy has been observed in other biosynthetic systems, including in NRPS thioester chain termination. Collectively, these studies establish the leupeptin biosynthetic gene cluster and the sequential order of reactivity utilizing "free" intermediates in product formation, in contrast to thiolation domain bound intermediates.

Example 2: Determining a Proposed Pathway of Biosynthesis of Leupeptins

Figure 2A:
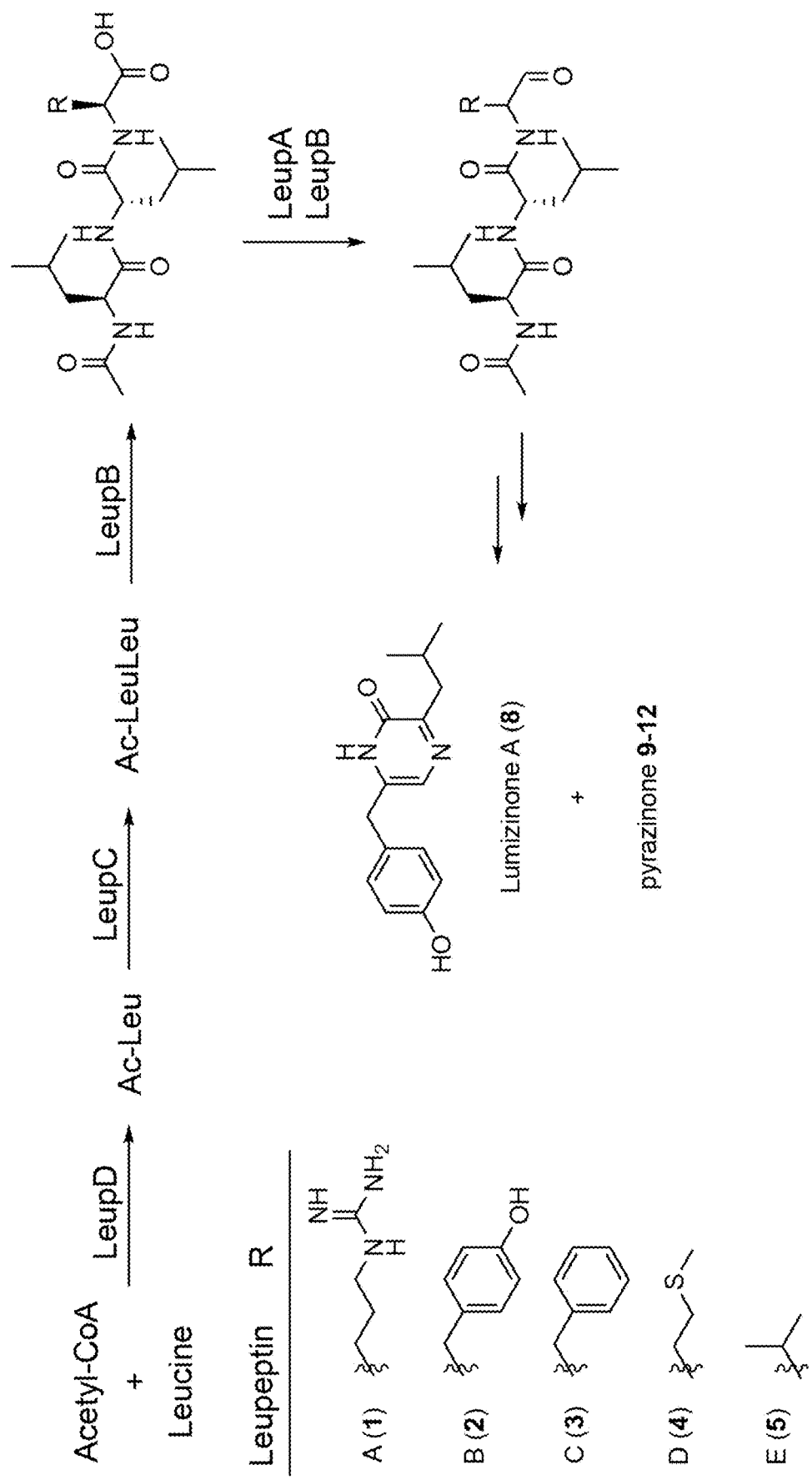
FIGS. 2A-2B illustrate proposed biosynthesis of the leupeptins.
Figure 2B:
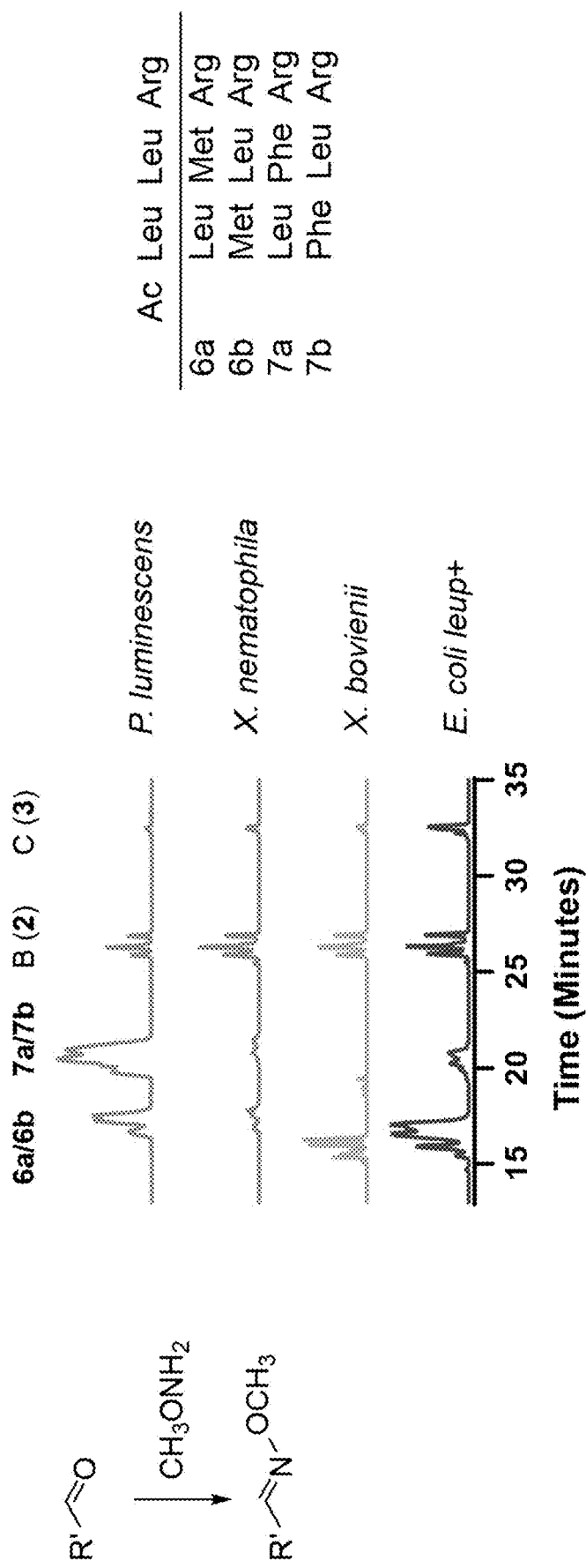

The chromatography of reactive carbonyl species like leupeptin can be complex (FIG. 1A). When the bacterial extracts were treated with methoxyamine to convert leupeptins into their respective oxime products, simpler and easier to interpret chromatograms were produced. This allowed for the efficient identification and characterization of other leupeptin analogs. Strikingly, the third arginine amino acid residue of major leupeptin A (1) could be substituted with tyrosine (leupeptin B, 2), phenylalanine (C, 3), methionine (D, 4), and valine (E, 5), as established by tandem MS of their oxime products. As representative members, leupeptin B was isolated from *X. nematophila* HGB1320 as its oxime adduct and confirmed by NMR (1D NMR, gCOSY, gHSQCAD, gHMBCAD), and leupeptin C was confirmed by comparison to a synthetic standar. While these molecules have previously been synthesized and confirmed to inhibit chymotrypsin-type proteases, this is the first time that these molecules have been identified as natural metabolites. Intriguingly, this indicates that the single leup operon promiscuously produces both trypsin-type (e.g., leupeptin A) and chymotrypsin-type (e.g., leupeptins B, C) protease inhibitors. Several analogs where leucine is replaced with phenylalanine or methionine (6a/6b, 7a/7b) were also identified, as well as their corresponding peptide precursors. In prior synthetic studies, these P2 and P3 modifications were shown to fine tune inhibitor selectivity. In addition, lumizinone A (8), which is a pyrazinone calpain protease inhibitor isolated from *P. luminescens*,[38] was also identified from this pathway (FIG. 2). This finding suggested that the tripeptide aldehydes (e.g., leupeptin B) could be converted via proteolysis into their respective dipeptide aldehydes, which are spontaneously cyclized and oxidized to their corresponding pyrazinones (e.g., lumizinone A). Taken together, this pathway produces a broad spectrum of pyrazinone, tripeptide- and dipeptide-aldehyde protease inhibitors.

In a parallel study investigating the metabolic effects of hypothetical protein Plu4509 in *P. luminescens*, a novel protease was unexpectedly identified that accepts leupeptins as substrates. A mutant required for the vertical transmission of *Photorhabdus khanii* NC1 to its host nematode *Heterorhabditis bacteriophora* M31e has been identified. Therefore, this mutant was incapable of colonizing infective juvenile progeny relative to wildtype bacteria during the nematode developmental lifecycle. The insertion was mapped to a gene predicted to encode a hypothetical protein with homology to plu4509 from the type strain *P. luminescens* TTO1. To further characterize the role of this gene, a deletion mutant of plu4509 was constructed in *P. luminescens* TTO1, and this mutant was indeed defective in transmission relative to wildtype.

Example 3: Metabolites Biosynthesized from Leupeptin Via Proteolytic Activity of Plu4509

Figure 3A:
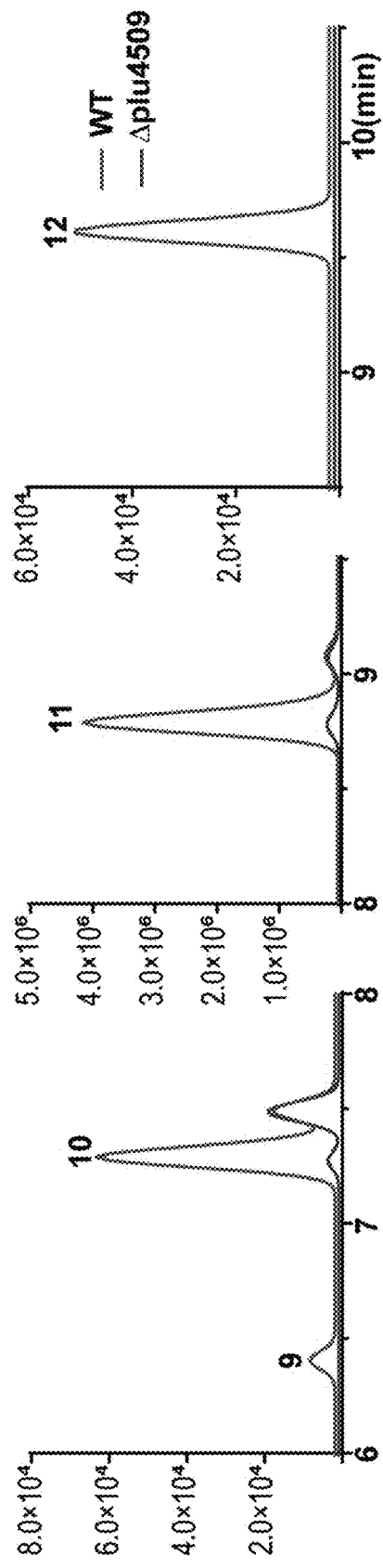
Figure 3B:
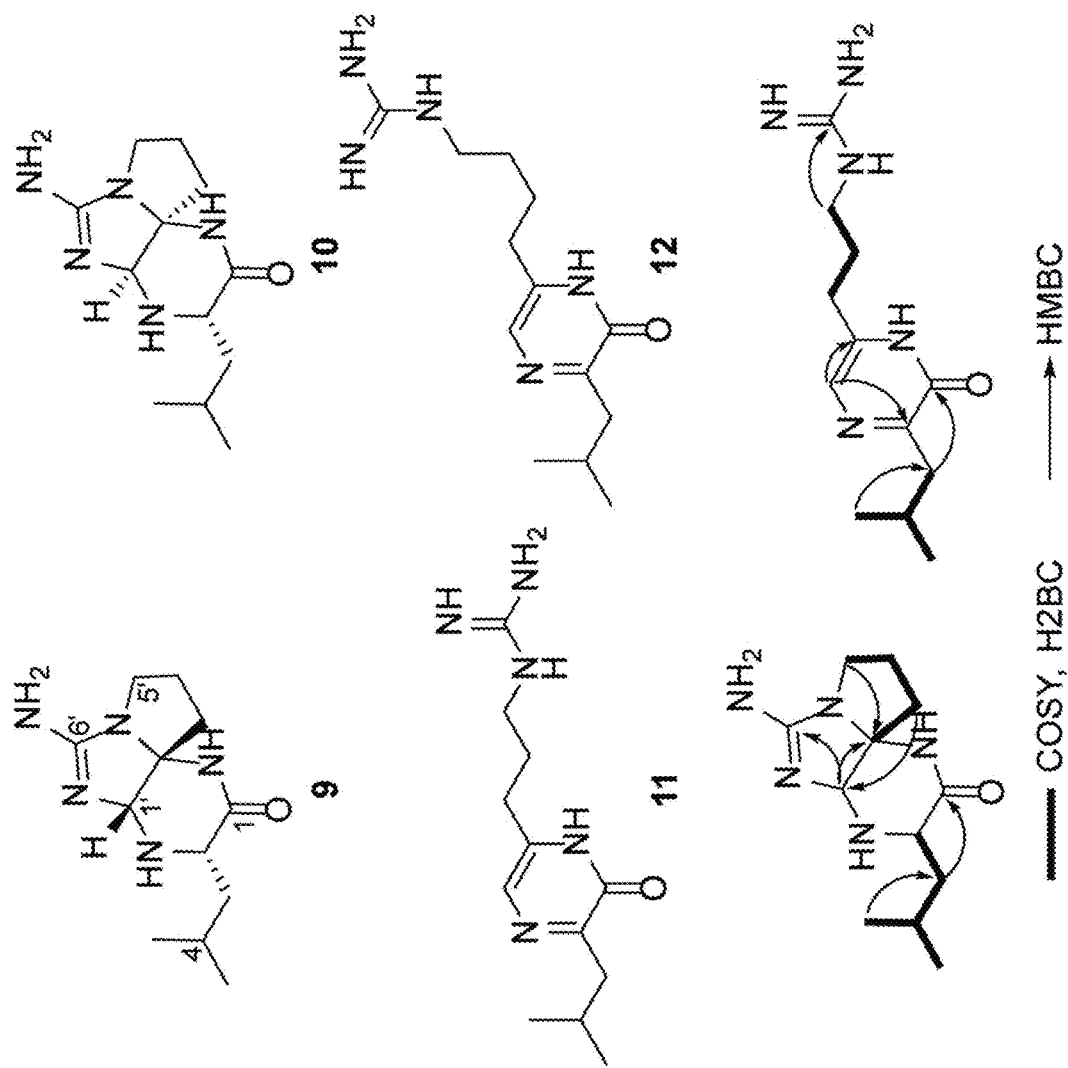

Comparative metabolomics was then conducted on the organic extracts between wildtype and the Δplu4509 strain cultivated in a hemolymph mimetic medium, which led to the characterization of differentially regulated Leu-Arg-derived pyrazinones (FIG. 3A). These metabolites were robustly produced in wildtype bacteria, whereas they were largely abrogated in the plu4509 mutant.

Figure 3D:
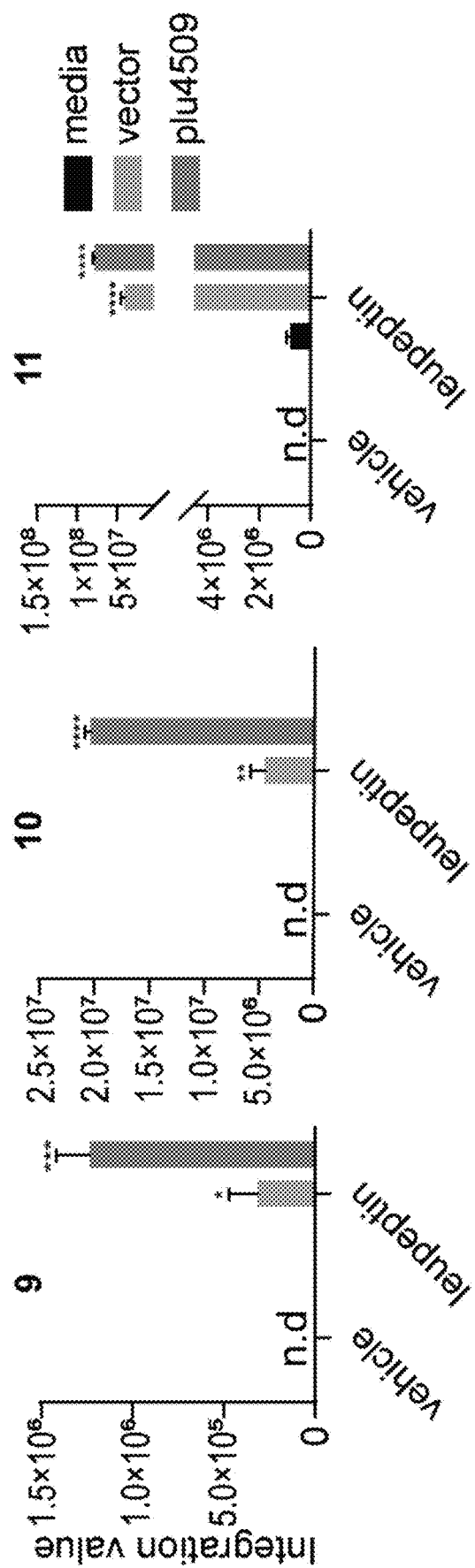
Figure 3E:
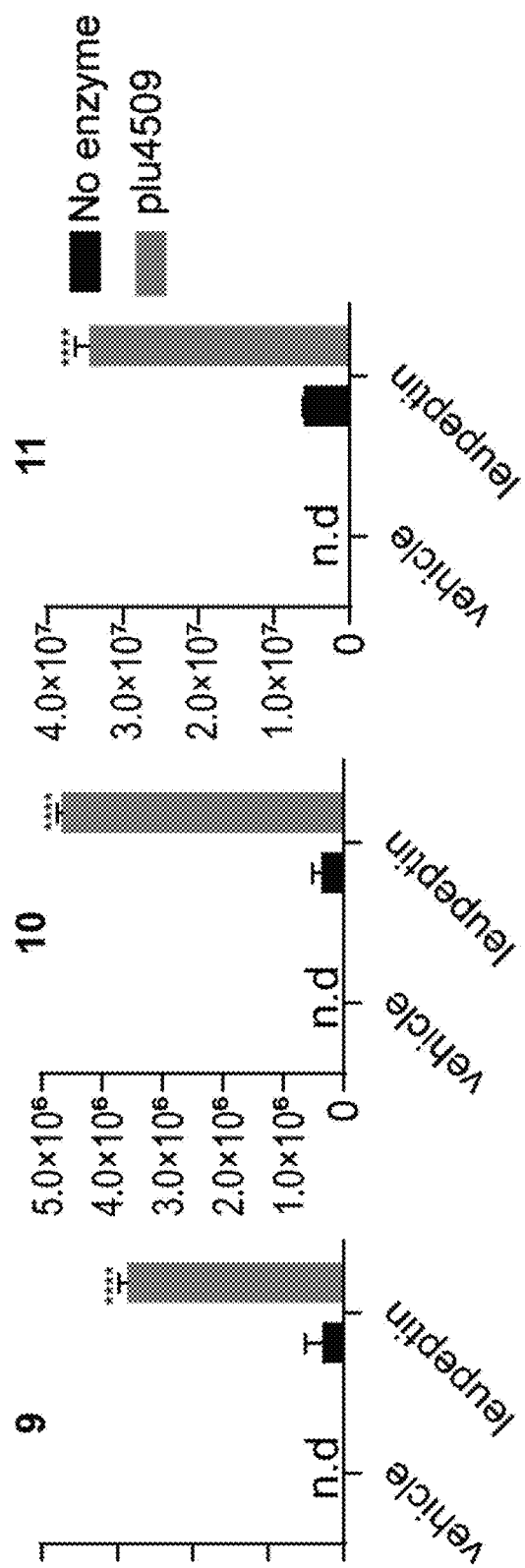

The absolute structures of 9-12 were established by NMR (1D NMR, gCOSY, gHSQCAD, gH2BCAD, gHMBCAD, and ROESY), chemical degradation and chiral derivatization (Marfey's approach), biomimetic synthesis, and chromatographic comparisons between natural materials and synthetic standards. Metabolites 9 and 10 are newly reported molecules featuring a novel tricyclic core comprised of tetrahydropyrrole, dihydroimidazole, and piperazine moieties, whereas 11 and 12 were previously identified in *Streptomyces* species. *Photorhabdus* bacteria engage in phase variation between P- and M-forms, in which the P-form is responsible for producing metabolites associated with insect virulence and nematode mutualism. In genetic variants of *P. luminescens* "locked" in the M- or P-forms, these metabolites were detected exclusively in the P-form variant. Under aerobic conditions, "pro-pyrazinones" 9 and 10 spontaneously converted to their pyrazinone counterpart 11. Given the structural similarities of these metabolites (Leu-Arg core) to leupeptin A and the identification of lumizinone A, without wishing to be bound by theory, it was hypothesized that the pyrazinones are derived from the leupeptin pathway via the unknown activity of hypothetical protein Plu4509. To test this hypothesis, plu4509 was first expressed in *E. coli* in the presence of leupeptin A versus water vehicle control and compared these samples to vector control samples (FIG. 3C). In these studies, *E. coli* control cultures were capable of generating both metabolites 10 and 11 with plu4509 providing an enhancement in production over controls. This suggested some functional redundancy in precursor degradation in *E. coli* and that Plu4509 may be a new type of protease. Consequently, in vitro protein biochemical studies were conducted to test this hypothesis. Candidate protease Plu4509 was purified as a $His_{6x}$-tagged variant, and production of metabolites 10 and 11 was monitored using leupeptin A as a substrate (FIG. 3D; end point analysis; 1 h, 35° C.). In line with the heterologous expression results, addition of enzyme indeed significantly enhanced production of 10 and 11 supporting the identification of a new type of leupeptin inactivating enzyme. Taken together, the genetics studies in *P. luminescens*, the heterologous expression studies in *E. coli*, and the protein biochemical studies support Plu4509 as a new type of protease that is capable of cleaving leupeptin analogs, leading to the formation of pyrazinone-type molecules.

Example 4: Phylogenetic and Syntenic Relationships of the Leup Operon

Figure 4:
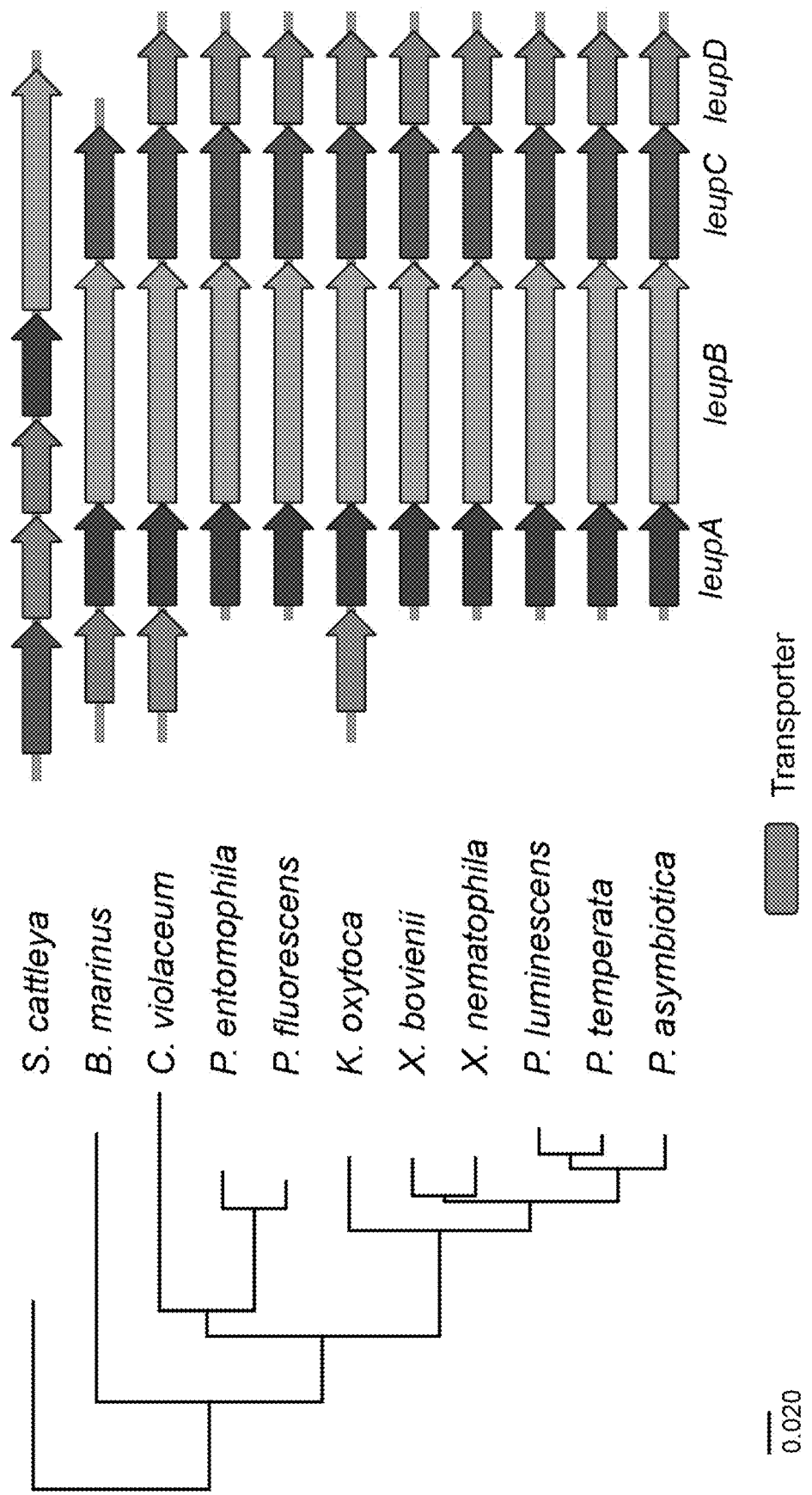
FIG. 4 illustrates the phylogenetic and syntenic relationships of the leup operon. The neighbor-joining tree is based on 16S rRNA sequences from *Streptomyces cattleya*, *Bacteriovorax marinus*, *Chromobacterium violaceum*, *Pseudomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperata* and *Photorhabdus asymbiotica*. The scale bar represents 0.02 substitutions per site. Orthologs are shown with the same color: leupA (fatty acid ligase) in green, leupB (reductase-ligase) in yellow, leupC (AMP-ligase) in navy, leupD (acetyltransferase) in orange, and an additional putative transporter in blue.

With the new leupeptin biosynthetic gene cluster being defined, studies were then conducted to determine if the pathway is more widely distributed in bacteria. Both *Xenorhabdus* and *Photorhabdus* species harbor the gene cluster (FIGS. 1A-1D, FIG. 4). The pathway was also conserved in the entomopathogens *Pseudomonas fluorescens* and *Pseudomonas entomophila*, in the germ-eating bacterium *Bacteriovorax marinus*, and in the human pathogens *Chromobacterium violaceum* and *Klebsiella oxytoca* (FIG. 4). Lastly, the pathway is found in multiple *Streptomyces* species, including *S. cattleya, S. albulus*, and the known leupeptin producer *S. roseochromogenes*. The pathway was distinct from recent NRPS bioinformatic proposals. To confirm production in non-*Photorhabdus/Xenorhabdus* isolates, leupABCD from *K. oxytoca* was first expressed in *E. coli* BL21(DE3). Leupeptin A (1) and analogs were produced, although the profile differed. Specifically, leupeptins, acetyl-Leu-Leu-Lys-aldehyde (13) and acetyl-Leu-Val-Lys-aldehyde (14), were produced at similar levels, whereas leupeptins B and C were undetectable under the conditions of these studies. This suggests that related leup operons exhibit variable substrate selectivity, which would affect the pathway's protease inhibitory spectrum (i.e., the chymotrypsin inhibitors were lacking in this pathway). An environmental isolate of *C. violaceum* was also confirmed to be a leupeptin producer.

Peptide aldehyde protease inhibitors are widely distributed in the human microbiota and are derived from bacterial NRPS pathways. The leupeptin protease inhibitor may in certain embodiments also be produced by an NRPS pathway; however, these predictions have not been experimentally confirmed. In the present disclosure, the leupeptin biosynthetic gene cluster was identified to consists of discrete ligases and accessory enzymes that are shared among *Streptomyces* and a collection of gammaproteobacterial pathogens. Host protease inhibition is an established virulence strategy in other pathogens. The leup operon encodes a diversity of leupeptin analogs that could regulate broad-spectrum protease inhibition, which may have contributed to the evolution of a new class of proteases with Plu4509 being the founding member. Together, these newly identified biosynthetic pathways make and break leupeptins, which may regulate developmental decisions at the host-bacteria interface.

Example 5: Synthesis Procedures

Leupeptin-Related Metabolites
Synthesis of Ac-L-Isoleucine.

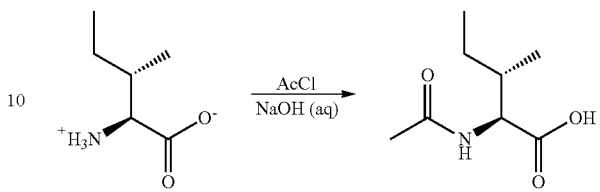

L-Isoleucine (1.8 g, 0.014 mol, 1.0 eq) was dissolved in 10 mL of $ddH_2O$ added with NaOH aqueous solution (5 N, 5.6 mL). A solution of acetyl chloride (1.0 mL in 4.0 mL acetonitrile, 0.014 mol, 1.0 eq) was then added gradually to the above solution at room temperature and stirred for 1 hour. The whole solution was then dried with $N_2$ and subjected to reverse phase $C_{18}$ flash chromatography with water/acetonitrile with 0.1% TFA. Fractions were collected and dried with $N_2$ and yielded 100.0 mg (4.2%). $^1$H NMR (400 MHz, Methanol-$d_4$) δ 2.03 (s, 3H), 4.36 (d, 1H), 1.88 (m, 1H), 1.52 (m, 2H), 0.98 (d, 3H), 0.94 (t, 3H). HRMS-ESI (m/z): $[M+H]^+$ calcd for $C_8H_{16}NO_3$, 174.1125; found 174.1129.

Synthesis of Ac-L-Leu-L-Leu Dipeptide.

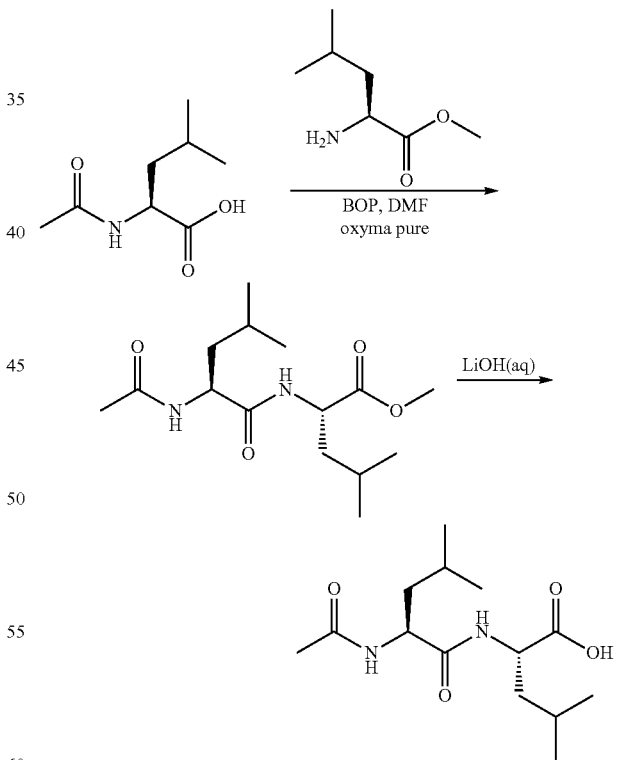

DMF (4.0 mL) was used to dissolve Ac-L-Leu (104.0 mg, 0.60 mmol, 1.0 eq), BOP (225.0 mg, 0.5090 mmol, 0.85 eq), oxyma pure (81.0 mg, 0.570 mmol, 0.95 eq), and DIPEA (298 μL, 1.71 mmol, 2.85 eq) was added and reacted until the solution turned yellow. The above solution was added to L-LeuOMe HCl (138.0 mg, 0.7600 mmol, 1.27 eq) in 2.0 mL of DMF and reacted at room temperature for 2 hours. The solution was dried with N₂ overnight and subjected to reverse phase $C_{18}$ flash chromatography with water/acetonitrile. The fractions were collected and dried under reduced pressure and yielded 40.0 mg (22%).

Purified Ac-L-Leu-L-LeuOMe was dissolved in 1.6 mL methanol and added 1.6 mL of 1 M LiOH aqueous solution and stirred for 2 hours. The solution was dried under N₂ and purified with reverse phase $C_{18}$ flash chromatography with water/acetonitrile with 0.1% TFA. The fractions were dried with reduced pressure and yielded 26.0 mg (0.091 mmol, 68%). ¹H NMR (400 MHz, Methanol-d₄) δ 1.97 (s, 3H), 8.07 (d, 1H, NH), 8.21 (d, 1H, NH), 4.43 (m, 2H, αH), 1.50-1.67 (m, 4H, βH), 1.72 (m, 2H, γH), 0.87-1.00 (m, 12H, δH). HRMS-ESI (m/z): [M+H]⁺ calcd for $C_{14}H_{27}N_2O_4$, 287.1965; found 287.1980.

Synthesis of Ac-L-Leu-L-Ile Dipeptide.

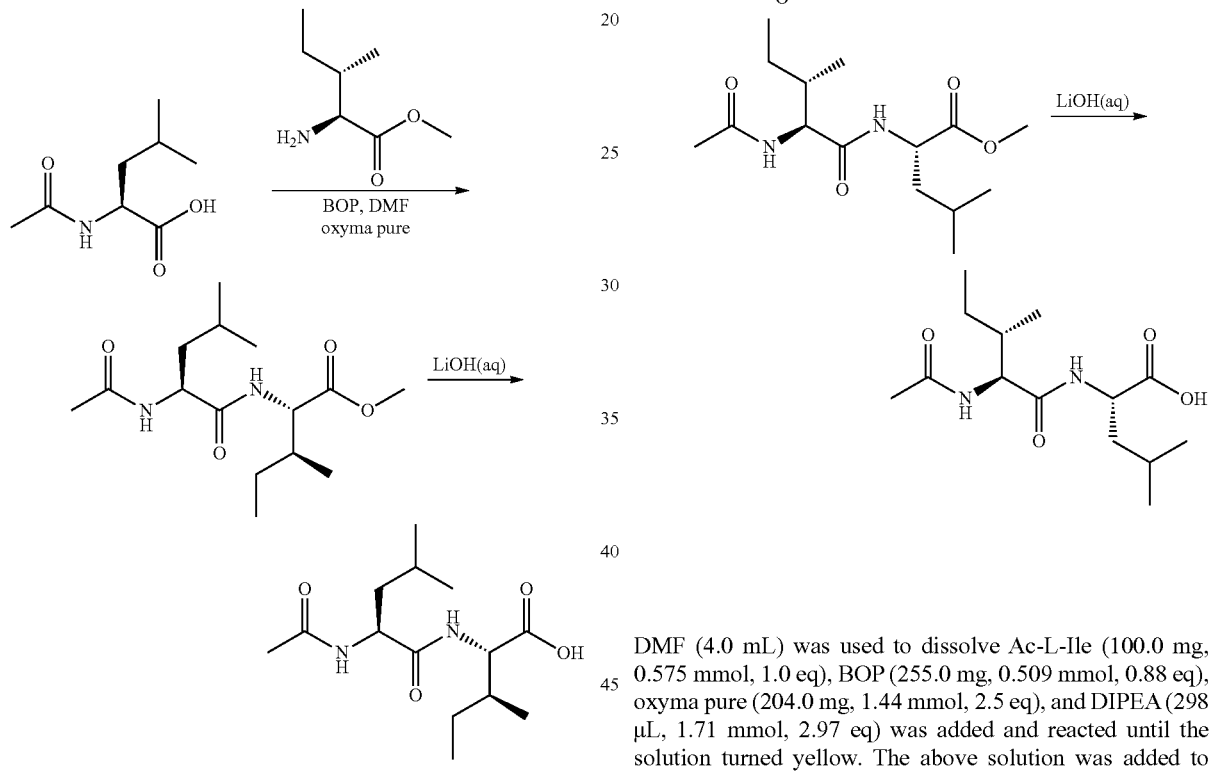

DMF (4.0 mL) was used to dissolve Ac-L-Leu (95.0 mg, 0.546 mmol, 1.0 eq), BOP (208.0 mg, 0.471 mmol, 0.86 eq), oxyma pure (118.0 mg, 0.831 mmol, 1.52 eq), and DIPEA (298 μL, 1.71 mmol, 3.13 eq) was added and reacted until the solution turned yellow. The above solution was added to L-IleOMe HCl (135.0 mg, 0.743 mmol, 1.36 eq) in 2.0 mL of DMF and reacted at room temperature for 2 hours. The solution was dried with N₂ overnight and subjected to reverse phase $C_{18}$ flash chromatography with water/acetonitrile. The fractions were collected and dried under reduced pressure and yielded 23.0 mg (14%).

Purified Ac-L-Leu-L-IleOMe was dissolved in 1.6 mL methanol and added 1.6 mL of 1 M LiOH aqueous solution and stirred for 2 hours. The solution was dried under N₂ and purified with reverse phase $C_{18}$ flash chromatography with water/acetonitrile with 0.1% TFA. The fractions were dried with reduced pressure and yielded 15.0 mg (0.052 mmol, 68%). ¹H NMR (400 MHz, Methanol-d₄) δ 1.97 (s, 3H), 8.02 (d, 1H, Ile-NH), 8.13 (d, 1H, Leu-NH), 4.45 (m, 1H, Leu-αH), 4.36 (m, 1H, Ile-αH), 1.57 (m, 2H, Leu-βH), 1.89 (m, 1H, Ile-βH), 1.26, 1.51 (m, 2H, Ile-γH), 1.68 (m, 1H, Leu-γH), 0.88-1.00 (m, 12H, CH3). HRMS-ESI (m/z): [M+H]⁺ calcd for $C_{14}H_{27}N_2O_4$, 287.1965; found 287.1971.

Synthesis of Ac-L-Ile-L-Leu Dipeptide.

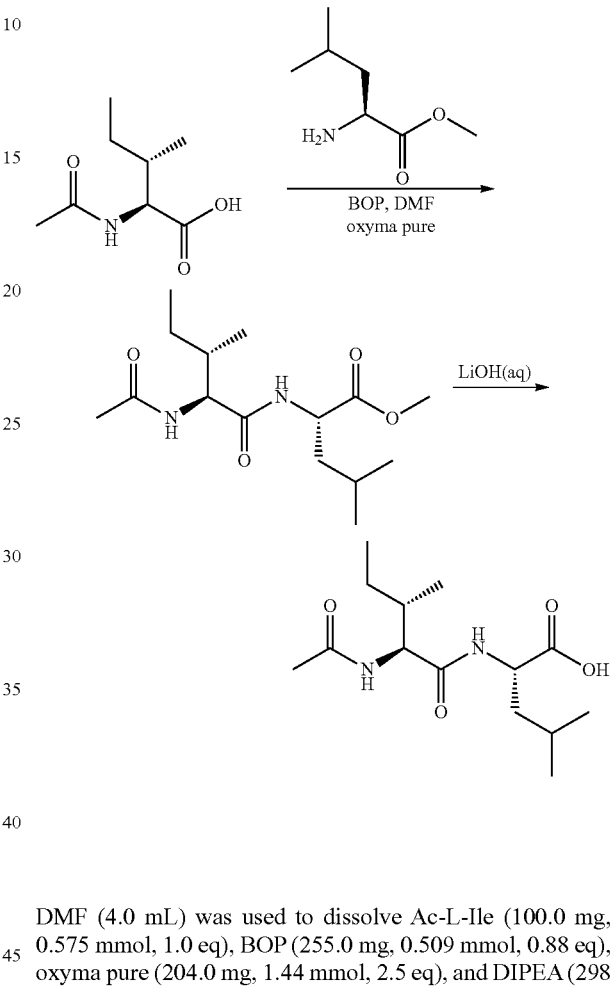

DMF (4.0 mL) was used to dissolve Ac-L-Ile (100.0 mg, 0.575 mmol, 1.0 eq), BOP (255.0 mg, 0.509 mmol, 0.88 eq), oxyma pure (204.0 mg, 1.44 mmol, 2.5 eq), and DIPEA (298 μL, 1.71 mmol, 2.97 eq) was added and reacted until the solution turned yellow. The above solution was added to L-LeuOMe HCl (135.0 mg, 0.743 mmol, 1.3 eq) in 2.0 mL of DMF and reacted at room temperature for 2 hours. The solution was dried with N₂ overnight and subjected to reverse phase $C_{18}$ flash chromatography with water/acetonitrile. The fractions were collected and dried under reduced pressure and yielded 105.0 mg (61%).

Purified Ac-L-Ile-L-LeuOMe was dissolved in 1.6 mL methanol and added 1.6 mL of 1 M LiOH aqueous solution and stirred for 2 hours. The solution was dried under N₂ and purified with reverse phase $C_{18}$ flash chromatography with water/acetonitrile with 0.1% TFA. The fractions were dried with reduced pressure and yielded 38.0 mg (0.132 mmol, 38%). ¹H NMR (400 MHz, Methanol-d₄) δ 1.98 (s, 3H), 7.96 (d, 1H, Ile-NH), 8.25 (d, 1H, Leu-NH), 4.44 (m, 1H, Leu-αH), 4.25 (m, 1H, Ile-αH), 1.64 (m, 2H, Leu-βH), 1.83 (m, 1H, Ile-βH), 1.19, 1.55 (m, 2H, Ile-γH), 1.72 (m, 1H, Leu-γH), 0.89-0.97 (m, 12H, CH3). HRMS-ESI (m/z): [M+H]⁺ calcd for $C_{14}H_{27}N_2O_4$, 287.1965; found 287.1967.

Synthesis of Ac-L-Leu-L-Leu-L-Phenylalaniol.

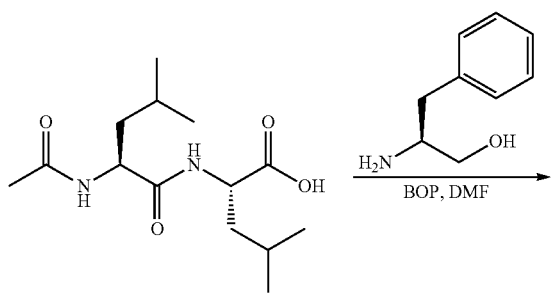

DMF (2 mL) was used to dissolve Ac-L-Leu-L-Leu (37.1 mg, 0.130 mmol, 1.0 eq), BOP (125.0 mg, 0.283 mmol, 2.18 eq), oxyma pure (38.0 mg, 0.268 mmol, 2.05 eq), and DIPEA (50 µL, 0.287 mmol, 2.21 eq) was added and reacted until the solution turned yellow. The above solution was added to L-phenylalaniol HCl (39.0 mg, 0.208 mmol, 1.60 eq) in 3 mL of DMF and reacted at room temperature for 2 hours. The solution was dried with $N_2$ and subjected to reverse phase $C_{18}$ flash chromatography with water/acetonitrile. The fractions were collected and dried under reduced pressure and yielded 38.3 mg (0.0914 mmol, 70%). $^1$H NMR (400 MHz, Methanol-$d_4$) δ 1.98 (s, 3H), 8.10 (d, 1H, NH), 7.92 (d, 1H, NH), 7.67 (d, 1H, Phe-NH), 4.33 (m, 2H, Leu-αH), 1.56 (m, 4H, Leu-βH), 1.67 (m, 2H, Leu-γH), 0.85-1.00 (m, 12H, δH), 4.08 (m, Phe-αH), 3.50 (d, 2H, Phe-βH), 2.75, 2.89 (dd, 2H, Phe-βH), 7.12-7.29 (m, 5H).

Synthesis of Ac-LeuLeuPhe-aldoxime (Leupeptin C Aldoxime).

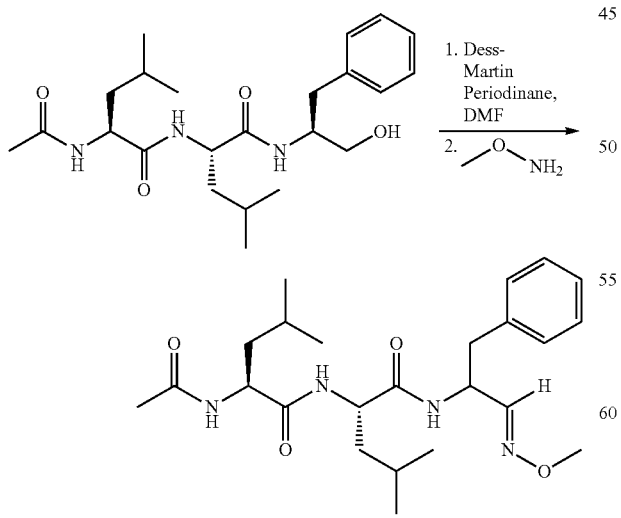

DMF (3.0 mL) was used to dissolve Ac-L-Leu-L-Leu-L-phenylalaniol (38.0 mg, 0.0907 mmol, 1.0 eq) and Dess-Martin periodinane (122 mg, 0.288 mmol, 3.17 eq) and stirred overnight at room temperature overnight. A DMSO solution of 680 mM methoxyamine (200 µL, 0.136 mmol, 1.4 eq) was added to the above solution and stirred overnight at room temperature. The solution was dried under $N_2$ overnight, extracted with ethyl acetate and water. The ethyl acetate layer was dried and purified on HPLC using a semiprep column (flow rate 2.0 mL/min, a linear gradient of water:acetonitrile with 0.1% formic acid, 48% to 60% in 24 min) and yielded 1.0 mg (2.4%) as a white solid. HRMS-ESI (m/z): [M+H]$^+$ calcd for $C_{24}H_{39}N_4O_4$, 447.2966; found 447.2968. NMR, see Table S4.

Biomimetic Synthetic Procedures of 9-12

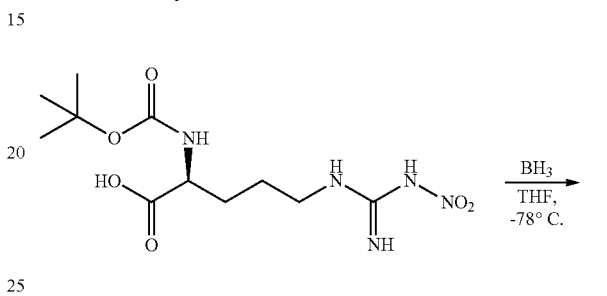

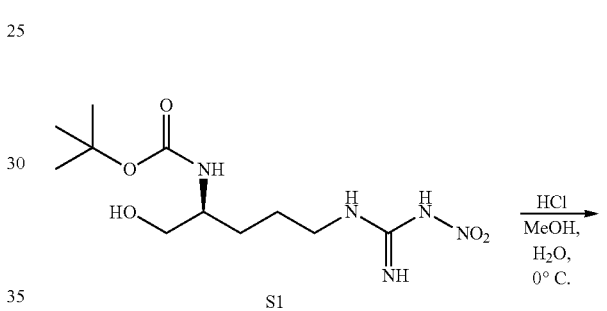

S1

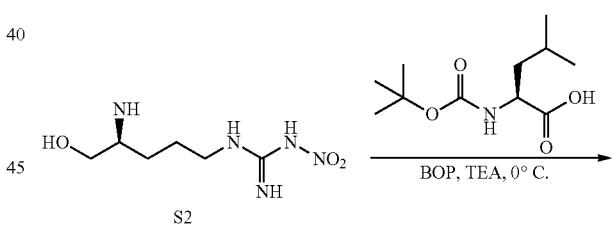

S2

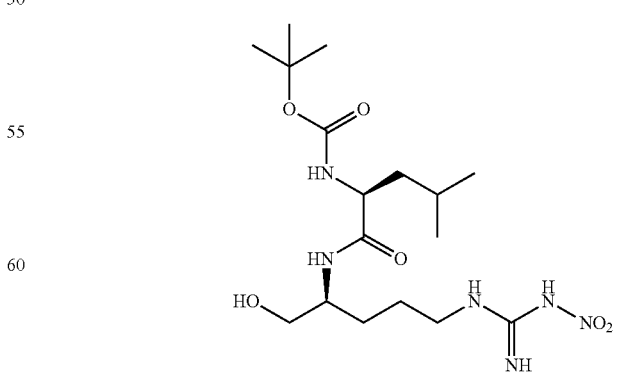

S3

-continued

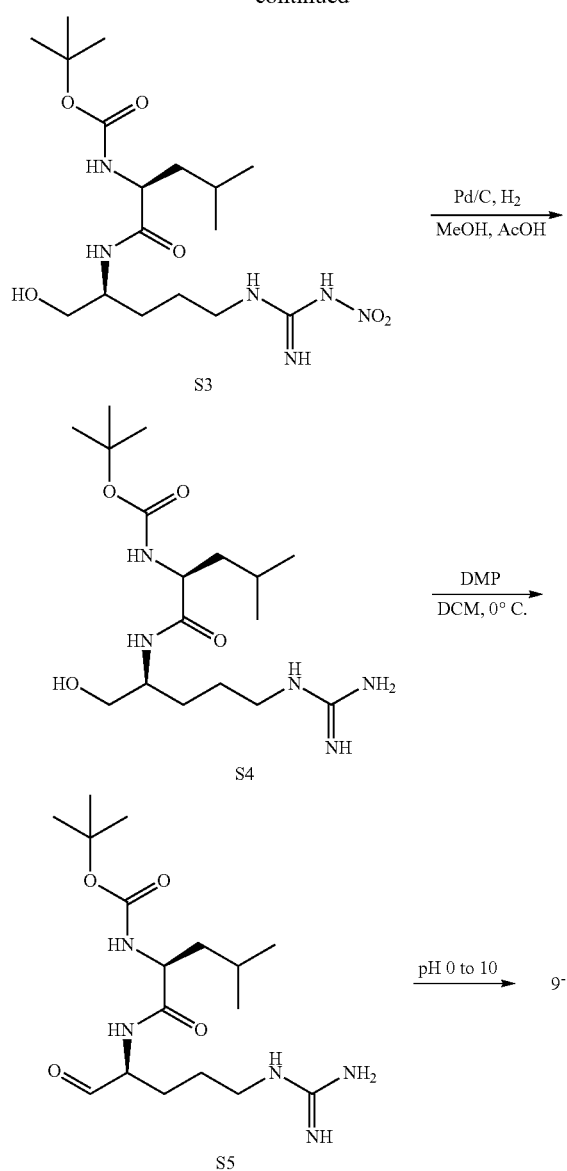

Synthesis of S1

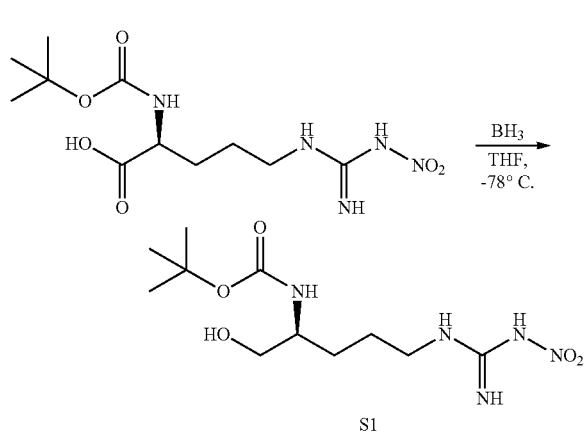

A solution of the starting material (5 g) in dry THF (200 mL) was cooled at −78° C. and borane tetrahydrofuran complex solution 1.0 M in THF (50 mL) was added. The reaction was kept overnight, and methanol and $H_2O$ were added slowly to remove the residual $BH_3$ at 0° C. The diluted product mixture was concentrated and purified employing RP HPLC to provide S1 (65%).

Synthesis of S2

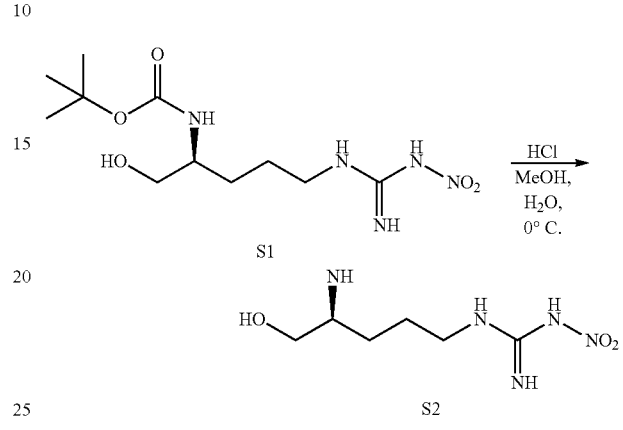

To a solution of S1 (4 g) in MeOH/$H_2O$ (1:1, 100 mL) was added HCl (~37%, 10 mL) at 0° C. and the reaction mixture was stirred for 4 h (r.t.). Upon the completion of deprotection, the reaction mixture was neutralized with NaOH and proceeded to the next step without purification (80%).

Synthesis of S3

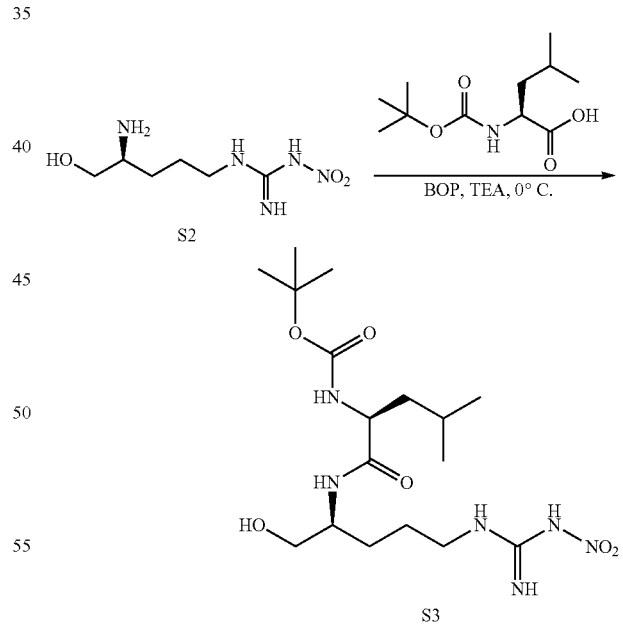

A solution of S2 (2 g) and N-Boc-L-leucine in DMF (250 mL) was added with BOP followed by TEA (10 mL) at 0° C., and the reaction mixture was stirred overnight. The reaction mixture was then neutralized and concentrated and S3 was acquired upon purification with RP HPLC (50%).

Synthesis of S4

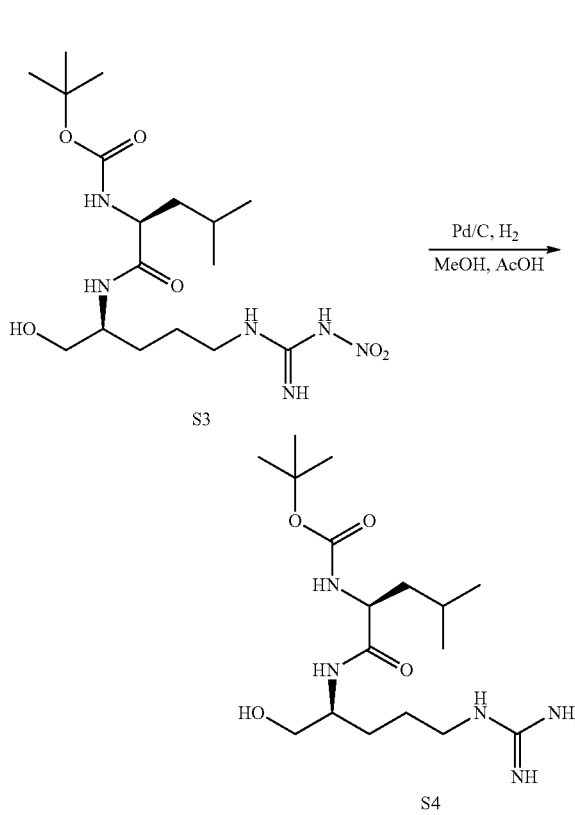

S3 (2 g) was dissolved in dichloromethane (100 mL) and acetic acid (100 mL), and the solution was degassed with nitrogen for 10 min. 10% Pd/C (1 g) were added and re-degassed the solution for 10 min. Then hydrogen gas was applied to the mixture at room temperature overnight. The reaction mixture was washed over Celite 535 with methanol and the filtrate was evaporated to yield a slurry. This reaction crude was purified using RP-HPLC to acquire S4 (70%).

Synthesis of S5

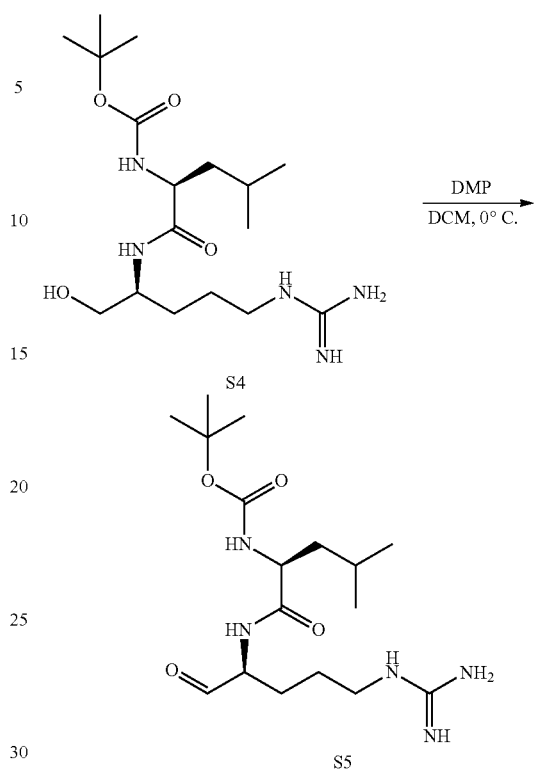

To a mixture of S4 (1 g) in DCM (100 mL) was added Dess-Martin periodinane (DMP, 2 g) in an ice bath and incubated for 4 h. The reaction was not quenched using a standard protocol using saturated $Na_2S_2O_4$ and $NaHCO_3$ since this process created other by-products of S5. Instead, the reaction mixture was diluted with addition of MeOH (200 mL) and concentrated. The LC-MS analysis of the reaction mixture showed corresponding peaks for S5 and its rearranged products such as diol products, leading their purification to be impractical. RP-HPLC was performed to collect fractions containing S5 with the rearranged products and those fractions were combined for the next step.

Synthesis of 9-11

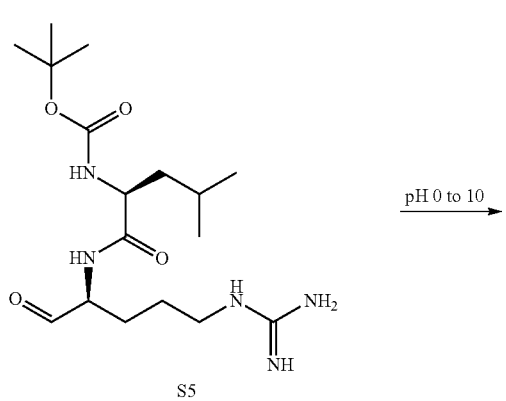

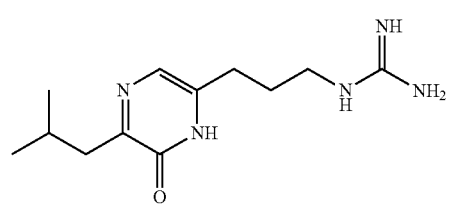

A mixture of S5 and rearranged products (500 mg) was dissolved in MeOH/H$_2$O (2:1, 100 mL) and deprotection was implemented with addition of HCl (~37%, 5 mL). After 1 h, the starting material was fully consumed and compound 11 was shown after another 2 h reaction, based on LC-MS monitoring. Then, pH was increased to ~10 by addition of 10 N NaOH and the reaction was stirred for another 2 h and the synthesis of compounds 9 and 10 was confirmed by LC-MS traces. The reaction mixtures were neutralized and concentrated to be subjected to RP-HPLC purification (9:10:11=40%:20%:30).

Synthesis of 12

The synthesis of 12 was achieved utilizing the identical manner to 11 with exception of the use of homoarginine instead of arginine.

TABLE 1

Primers used in this study.

| Primer | SEQ ID NO: | Sequence (5' to 3') | Description |
|---|---|---|---|
| NdeIfw | 6. | CTGAACcatatgACTTCTCTTGCTTATGTTGACGCC | Forward primer to clone leupeptin pathway from *X bovienii* str felitae Moldova |
| AvrIIrv | 7. | CTGAACcctaggTTACCTTTCGGCACAGGCAAACAG | Reverse primer to clone leupeptin pathway from *X bovienii* str felitae Moldova |
| KO1-1 | 8. | gtaaaaaatCATATGTATTTAGTTAATGGCGAGGTTAT | Clean knockout (KO) of leupA by PCR amplify the whole plasmid and ligate it back with restriction site NdeI, forward |
| KO1-2 | 9. | GtaaaaaatcatatgtatatctccttcttatacttaactaatatactaagatG | Clean KO of leupA by PCR amplify the whole plasmid and ligate it back with restriction site NdeI, reverse |
| KO2-1 | 10. | gtaaaaaaTTAATTAAGGAGATATACCATGACTTTATCATTACACGATCTAGTGG | Clean KO of leupB by PCR amplify the whole plasmid without leupB, insert RBS and ligate it back with restriction site PacI, forward |
| KO2-2 | 11. | gtaaaaaaTTAATTAATCAGGATTCCTTAATCAACTCAGAA | Clean KO of leupB by PCR amplify the whole plasmid without leupB, insert RBS and ligate it back with restriction site PacI, reverse |
| KO3-1 | 12. | gtaaaaaaTTAATTAAGGAGATATACCATGAATATAAATCCAGTCATGCCGT | Clean KO of leupC by PCR amplify the whole plasmid without leupB, insert RBS and ligate it back with restriction site PacI, forward |
| KO3-2 | 13. | gtaaaaaaTTAATTAATCAGACGCGATAATCCAGCACT | Clean KO of leupC by PCR amplify the whole plasmid without leupB, insert RBS and ligate it back with restriction site PacI, reverse |
| KO4-1 | 14. | gtaaaaaatcctaggctgctgccacc | Clean KO of leupD by PCR amplify the whole plasmid and ligate it back with restriction site AvrII, forward |
| KO4-2 | 15. | gtaaaaaatCCTAGGTCATGCTGTCTTCTCTTCAGCATTATAACAAC | Clean KO of leupD by PCR amplify the whole plasmid and ligate it back with restriction site AvrII, reverse |

TABLE 1-continued

Primers used in this study.

| Primer | SEQ ID NO: | Sequence (5' to 3') | Description |
| --- | --- | --- | --- |
| NKOX AscI | 16. | gtaaaaaatGGCGCGCCTGGACACTTTATCCTGCGTC | Forward primer to clone leup operon from *K. oxytoca* KCTC1686 with AscI |
| CKOX HindIII | 17. | gtaaaaaatAAGCTTGCGTCAGATAAAAGGGATTGTCA | Reverse primer to clone leup operonfrom *K. oxytoca* KCTC1686 with HindIII |
| 4509NdeIfw | 18. | CTGAACcatatgCCTAATATTTTCATGGGAGAATGGTCTCC | Forward primer to clone plu4509 with His$_6$-tag |
| 4509HindIIIrv | 19. | CTGAACaagcttTtATGCGATCCTCCTGTAATAAAGC | Reverse primer to clone plu4509 |
| npsB_f | 20. | CTCGACGTTTTATCTCTGCTG | This study |
| npsB_r | 21. | TTCCTGAAGTATCTGCCCTGC | This study |
| gapA_fwd | 22. | gaacccagtcacgacgttgtatgaagtatgactccactcacgg | (Herzog etal. 2014) |
| gapA_rev | 23. | ttgtgagcggataacaatacaacgcctacattgcgccttcggaa | (Herzog etal. 2014) |
| leupA | 24. | ATGAAGATAGCGATTCACAAC | This study |
| leupB_r | 25. | GCGTGGTCTTTTAGCTGTTC | This study |
| leupDr | 26. | CATATCGGTAAAACCTGCTCG | This study |

$^a$ Overhang sequences are underlined.

TABLE 2

Key bacterial strains and plasmids in this study.

| Plasmid or strain | Description | Source or Reference |
| --- | --- | --- |
| Plasmids | | |
| pCDF-Leup | pCDFDuet with Leup operon (XBFM1_900063, XBFM1_900062, XBFM1_900061, XBFM1_900060) | This work |
| pCDF-ΔleupA | pCDFDuet with Leup operon (XBFM1_900062, XBFM1_900061, XBFMl_900060) | This work |
| pCDF-ΔleupB | pCDFDuet with Leup operon (XBFM1_900063, XBFM1_900061, XBFMl_900060) | This work |
| pCDF -ΔleupC | pCDFDuet with Leup operon (XBFM1_900063, XBFM1_900062, XBFMl_900060) | This work |
| pCDF-ΔleupD | pCDFDuet with Leup operon (XBFM1_900063, XBFM1_900062, XBFM1_900061) | This work |
| pCDF-LeupKOX | pCDFDuet with *K. oxytoca* Leup operon (KOX07030, KOX07025, KOX07020, KOX07015) | This work |
| Strains | | |
| *E. coli* DH5a | General cloning strain. | |
| *E. coli* BL21(DE3) | General expression strain. | |
| *X. bovienii* SS-2004 | | In house |
| *X. bovienii* str. felitae Moldova | | In house |
| *X. nematophila* HGB1320 | *X. nematophila* wild-type ΔlrhA2 | (Richards and Goodrich-Blair, 2010) |

TABLE 2-continued

Key bacterial strains and plasmids in this study.

| Plasmid or strain | Description | Source or Reference |
|---|---|---|
| P. luminescens TTO1 | | In house |
| P. luminescens TTO1 Δplu4509 | | In house |
| P. asymbiotica ATCC 43949 | | In house |
| P. temperata J3 | | In house |
| K. oxytoca KCTC1686 | K. oxytoca ATCC8724 | Thermo-Fischer |

TABLE 3

NMR assignment of Leupeptin B-aldoxime.

| | | δH | δC |
|---|---|---|---|
| Acetyl | $CH_3$ | 1.98, s, 3H | 20.97 |
| | C=O | | 172.07 |
| Leucine | α | 4.34, m, 2H | 51.84 |
| | β | 1.51, m, 4H | 40.36 |
| | γ | 1.67, m, 2H | 24.42 |
| | δ | 0.90, m, 3H | 20.54 |
| | | 0.86, m, 3H | 20.58 |
| | | 0.94, m, 3H | 21.98 |
| | | 0.91, m, 3H | 21.93 |
| | C=O | | 172.96 |
| | | | 173.07 |
| Tyrosine | α | 4.62 (major), m, 1H | 50.31 (major) |
| | | 5.07 (minor), m | 47.02 (minor) |
| | β | 2.86 (major), m, 2H | 37.34 (major) |
| | | 2.84 (minor), m | 36.06 (minor) |
| | γ | | 127.52 |
| | δ | 7.01, d, J = 8.5 Hz, 2H | 130.00 |
| | ε | 6.69, d, J = 8.5 Hz, 2H | 114.74 |
| | C—OH | | 155.75 |
| | CH=N | 7.30 (major), d, J = 5.4 Hz, 1H | 148.67 (major) |
| | | 6.61 (minor), d, J = 6.2 Hz | 150.18 (minor) |
| Methoxy | $CH_3$ | 3.74 (major), s, 3H | 60.52 (major) |
| | | 3.80 (minor) | 60.88 (minor) |

[a] Leucines are not distinguished.
[b] Measured in methanol-$d_4$

TABLE 4

NMR Assignment of Leupeptin C-aldoxime.

| | | δH |
|---|---|---|
| Acetyl | $CH_3$ | 1.97, s, 3H |
| Leucine | α | 4.33, 4.27, m, 2H |
| | β | 1.52, 1.34, m, 4H |
| | γ | 1.67, 1.40, m, 2H |
| | δ | 0.90, 0.82, m, 12H |
| Phenylalanine | α | 4.75 (major), m, 1H |
| | | 5.20 (minor), m |
| | β | 2.88, 3.06 (major), m, 2H |
| | | 2.81, 3.07 (minor), m |
| | Aromatic | 7.17-7.28, m, 5H |
| | CH=N | 7.35 (major), d, J = 5.4 Hz, 1H |
| | | 6.66 (minor), d, J = 6.0 Hz |
| Methoxy | $CH_3$ | 3.78 (major), s, 3H |
| | | 3.86 (minor) |

[a] Measured in methanol-$d_4$
[b] Leucines are not distinguished

TABLE 5

Tripeptide aldehydes identified in E. coli leup+, X. bovienii, X. nematophila and P. luminescens. All of the products were detected in E. coli leup+. Aldehydes were characterized as the corresponding oximes.

| Compound | Molecular Formula | [MH+] | X. bovienii SS-2004 | X. nematophila HGB1320 | P. luminescens TTO1 |
|---|---|---|---|---|---|
| Ac-LLY-OH | $C_{23}H_{35}N_3O_6$ | 450.2599 | | | |
| Ac-LLY-oxime | $C_{24}H_{38}N_4O_5$ | 463.2915 | Yes | Yes | Yes |
| Ac-LLF-OH | $C_{23}H_{35}N_3O_5$ | 434.2649 | | | |
| Ac-LLF-oxime | $C_{24}H_{38}N_4O_4$ | 447.2966 | Yes | Yes | Yes |
| Ac-LLM-OH | $C_{19}H_{35}N_3O_5S$ | 418.2370 | | | |
| Ac-LLM-oxime | $C_{20}H_{38}N_4O_4S$ | 431.2687 | Yes | | |
| Ac-LLV-OH | $C_{19}H_{35}N_3O_5$ | 386.2649 | | | |
| Ac-LLV-oxime | $C_{20}H_{38}N_4O_4$ | 399.2966 | Yes | | |
| Ac-LMR-OH | $C_{19}H_{36}N_6O_5S$ | 461.2541 | | | |
| Ac-LMR-oxime | $C_{20}H_{39}N_7O_4S$ | 474.2857 | Yes | Yes | Yes |
| Ac-MLR-OH | $C_{19}H_{36}N_6O_5S$ | 461.2541 | | | |
| Ac-MLR-oxime | $C_{20}H_{39}N_7O_4S$ | 474.2857 | Yes | Yes | Yes |
| Ac-LMY-OH | $C_{22}H_{33}N_3O_6S$ | 468.2163 | | | |
| Ac-LMY-oxime | $C_{23}H_{36}N_4O_5S$ | 481.2479 | Yes | Yes | Yes |
| Ac-MLY-OH | $C_{22}H_{33}N_3O_6S$ | 468.2163 | | | |
| Ac-MLY-oxime | $C_{23}H_{36}N_4O_5S$ | 481.2479 | Yes | Yes | Yes |
| Ac-LMF-OH | $C_{22}H_{33}N_3O_5S$ | 452.2214 | | | |
| Ac-LMF-oxime | $C_{23}H_{36}N_4O_4S$ | 465.2530 | Yes | | Yes |
| Ac-MLF-OH | $C_{22}H_{33}N_3O_5S$ | 452.2214 | | | |
| Ac-MLF-oxime | $C_{23}H_{36}N_4O_4S$ | 465.2530 | Yes | | Yes |
| Ac-LMM-OH | $C_{18}H_{33}N_3O_5S_2$ | 436.1934 | | | |
| Ac-LMM-oxime | $C_{19}H_{36}N_4O_4S_2$ | 449.2251 | Yes | | |
| Ac-MLM-OH | $C_{18}H_{33}N_3O_5S_2$ | 436.1934 | | | |

TABLE 5-continued

Tripeptide aldehydes identified in *E. coli* leup+, *X. bovienii*,
*X. nematophila* and *P. luminescens*. All of the products were detected in
*E. coli* leup+. Aldehydes were characterized as the corresponding oximes.

| Compound | Molecular Formula | [MH+] | X. bovienii SS-2004 | X. nematophila HGB1320 | P. luminescens TTO1 |
|---|---|---|---|---|---|
| Ac-LFR-oxime | $C_{24}H_{39}N_7O_4$ | 490.3136 | Yes | Yes | Yes |
| Ac-FLR-OH | $C_{23}H_{36}N_6O_5$ | 477.2820 | | | |
| Ac-FLR-oxime | $C_{24}H_{39}N_7O_4$ | 490.3136 | Yes | Yes | Yes |
| Ac-LFY-oxime | $C_{27}H_{36}N_4O_5$ | 497.2758 | Yes | | |
| Ac-FLY-OH | $C_{26}H_{33}N_3O_6$ | 484.2442 | | | |
| Ac-FLY-oxime | $C_{27}H_{36}N_4O_5$ | 497.2758 | Yes | | |
| Ac-LFF-OH | $C_{26}H_{33}N_3O_5$ | 468.2493 | | | |
| Ac-LFF-oxime | $C_{27}H_{36}N_4O_4$ | 481.2809 | | | |
| Ac-FLF-OH | $C_{26}H_{33}N_3O_5$ | 468.2493 | | | |
| Ac-FLF-oxime | $C_{27}H_{36}N_4O_4$ | 481.2809 | | | |
| Ac-FLM-OH | $C_{22}H_{33}N_3O_5S$ | 452.2214 | | | |
| Ac-MFR-OH | $C_{22}H_{34}N_6O_5S$ | 495.2384 | | | |
| Ac-FMR-OH | $C_{22}H_{34}N_6O_5S$ | 495.2384 | | | |
| Ac-FMR-oxime | $C_{23}H_{37}N_7O_4S$ | 508.2700 | | | |
| Ac-MFY-oxime | $C_{26}H_{34}N_4O_5S$ | 515.2323 | | | |
| Ac-FMY-OH | $C_{25}H_{31}N_3O_6S$ | 502.2006 | | | |
| Ac-FMY-oxime | $C_{26}H_{34}N_4O_5S$ | 515.2323 | | | |
| Ac-MFF-OH | $C_{25}H_{31}N_3O_5S$ | 486.2057 | | | |
| Ac-MFF-oxime | $C_{26}H_{34}N_4O_4S$ | 499.2374 | | | |
| Ac-FMF-OH | $C_{25}H_{31}N_3O_5S$ | 486.2057 | | | |
| Ac-FMF-oxime | $C_{26}H_{34}N_4O_4S$ | 499.2374 | | | |
| Ac-MMR-OH | $C_{18}H_{34}N_6O_5S_2$ | 479.2105 | | | |
| Ac-MMR-oxime | $C_{19}H_{37}N_7O_4S_2$ | 492.2421 | Yes | | |
| Ac-MMY-OH | $C_{21}H_{31}N_3O_6S_2$ | 486.1727 | | | |
| Ac-MMY-oxime | $C_{22}H_{34}N_4O_5S_2$ | 499.2043 | | | |
| Ac-MMF-OH | $C_{21}H_{31}N_3O_5S_2$ | 470.1778 | | | |
| Ac-MMF-oxime | $C_{22}H_{34}N_4O_4S_2$ | 483.2094 | | | |

TABLE 6

$^1$H and $^{13}$C NMR spectroscopic data of natural and synthetic 9 and 10 (25° C., $D_2O$).

| | 9 (synthetic)$^a$ | | 10 (natural) | | 10 (synthetic) | |
|---|---|---|---|---|---|---|
| Position | $\delta_H$, mult. (J in Hz) | $\delta_C$ | $\delta_H$, mult. (J in Hz) | $\delta_C$ | $\delta_H$, mult. (J in Hz) | $\delta_C$ |
| 1 | | 173.7 | | 177.9 | | 176.9 |
| 2 | 3.63, dd (6, 10) | 52.3 | 3.43, dd (4, 10) | 48.4 | 3.53, dd (4, 9) | 48.5 |
| 3 | 1.45, dd (5, 10) | 38.1 | 1.32, t (10) | 37.0 | 1.31, t (10) | 36.5 |
|  | 1.50, dd (6, 10) |  | 1.66, dd (4, 10) |  | 1.66, dd (4, 10) |  |
| 4 | 1.67, m | 23.8 | 1.64, m | 23.8 | 1.60, m | 23.8 |
| 5 | 0.76, d (6) | 20.4 | 0.79, d (6) | 20.2 | 0.74, d (6) | 20.2 |
| 6 | 0.78, d (6) | 21.9 | 0.84, d (6) | 22.5 | 0.79, d (6) | 22.3 |
| 1' | 5.33, s | 67.8 | 5.20, s | 71.4 | 5.30, s | 70.5 |
| 2' | | 82.7 | | 81.9$^b$ | | 82.6 |
| 3' | 1.95, 2.09, m | 35.3 | 2.03, 2.09, m | 34.8 | 2.00, 2.07, m | 34.7 |
| 4' | 2.14, m | 23.4 | 2.15, m | 24.5 | 2.13, m | 24.3 |
| 5' | 3.35, 3.40, m | 46.1 | 3.34, 3.38, m | 45.8 | 3.31, 3.36, m | 45.7 |
| 6' | | 160.2 | | 160.4 | | 160.4 |

$^a$NMR spectroscopic data for natural 9 is not available-see Structural characterization of 9-12,
$^b$Recorded in methanol-$d_4$ due to weak signal in $D_2O$

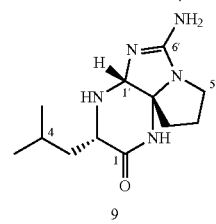

9

TABLE 6-continued

¹H and ¹³C NMR spectroscopic data of natural and synthetic 9 and 10 (25° C., D₂O).

|  | 9 (synthetic)[a] | | 10 (natural) | | 10 (synthetic) | |
|---|---|---|---|---|---|---|
| Position | $\delta_H$, mult. (J in Hz) | $\delta_C$ | $\delta_H$, mult. (J in Hz) | $\delta_C$ | $\delta_H$, mult. (J in Hz) | $\delta_C$ |

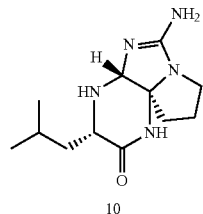 [SMILES: CC(C)C[C@@H]1N[C@@H]2N=C(N)N3CCC[C@]23NC1=O]

10

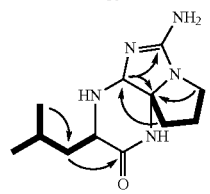

— COSY, H2BC

25

TABLE 7

¹H and ¹³C NMR spectroscopic data and assignment of S1-S4 (methanol-d₄)[a]

| | S1 | | S2 | | S3 | | S4 | |
|---|---|---|---|---|---|---|---|---|
| Position | $\delta_H$ mult. (J in Hz) | $\delta_C$ | $\delta_H$ | $\delta_C$ | $\delta_H$ | $\delta_C$ | $\delta_H$ | $\delta_C$ |
| 1 | 3.45, qd (10, 5) | 63.9 | 3.56, dd (11, 7); 3.76, dd (11, 4) | 59.8 | 3.48, m | 62.9 | 3.49, qd (10, 5) | 62.8 |
| 2 | 3.52, br m | 51.7 | 3.25, m | 52.1 | 3.91, br m | 49.6 | 3.87, m | 49.7 |
| 3 | 1.39, 1.64, br m | 28.2 | 1.68, br m | 25.3 | 150 t (7); 1.65 m | 27.2 | 1.48, 1.64, m | 27.1 |
| 4 | 1.68, br m | 24.8 | 1.68, br m | 25.3 | 1.64, m | 27.3 | 1.59, 1.62, m | 24.1 |
| 5 | 3.23, m | 40.7 | 3.29, m | 39.7 | 3.21, br | 40.0 | 3.14, 3.22, m | 40.0 |
| 6 | | 159.5 | | 158.8 | | 158.7 | | 156.5 |
| 1' | | | | | | 174.1 | | 174.0 |
| 2' | | | | | 4.05, t (7) | 52.7 | 4.02, t (7) | 52.8 |
| 3' | | | | | 1.50, m | 40.1 | 1.51, m | 40.0 |
| 4' | | | | | 1.67, m | 23.8 | 1.67, m | 23.7 |
| 5' | | | | | 0.91, d (7) | 19.8 | 0.91, d (7) | 19.8 |
| 6' | | | | | 0.93, d (7) | 21.3 | 0.93, d (7) | 21.3 |
| 1" | | 157.0 | | | | 155.8 | | 155.8 |
| 2" | | 78.7 | | | | 78.5 | | 78.5 |
| 3" | 1.42, s | 27.3 | | | 1.42, s | 26.6 | 1.42, s | 26.6 |
| 2-NH[b] | 6.40, d (10) | | | | 7.75, br d | | 7.79, d (9) | |
| 2'-NH[b] | | | | | 6.73, d (6) | | 6.78, d (7) | |

[a]The NMR spectroscopic data of S5 are not available due to its inseparable rearranged products, see Synthetic Procedure section.
[b]Despite use of protic deuterated solvent, some exchangeable protons were detectable with variable intensities.

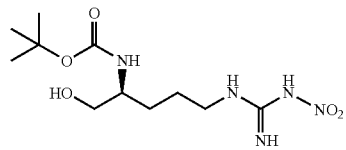

S1

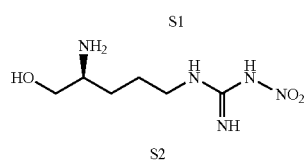

S2

TABLE 7-continued $^1$H and $^{13}$C NMR spectroscopic data and assignment of S1-S4 (methanol-$d_4$)$^a$

| | S1 | | S2 | | S3 | | S4 | |
|---|---|---|---|---|---|---|---|---|
| Position | $\delta_H$ mult. (J in Hz) | $\delta_C$ | $\delta_H$ | $\delta_C$ | $\delta_H$ | $\delta_C$ | $\delta_H$ | $\delta_C$ |

Figure 7:
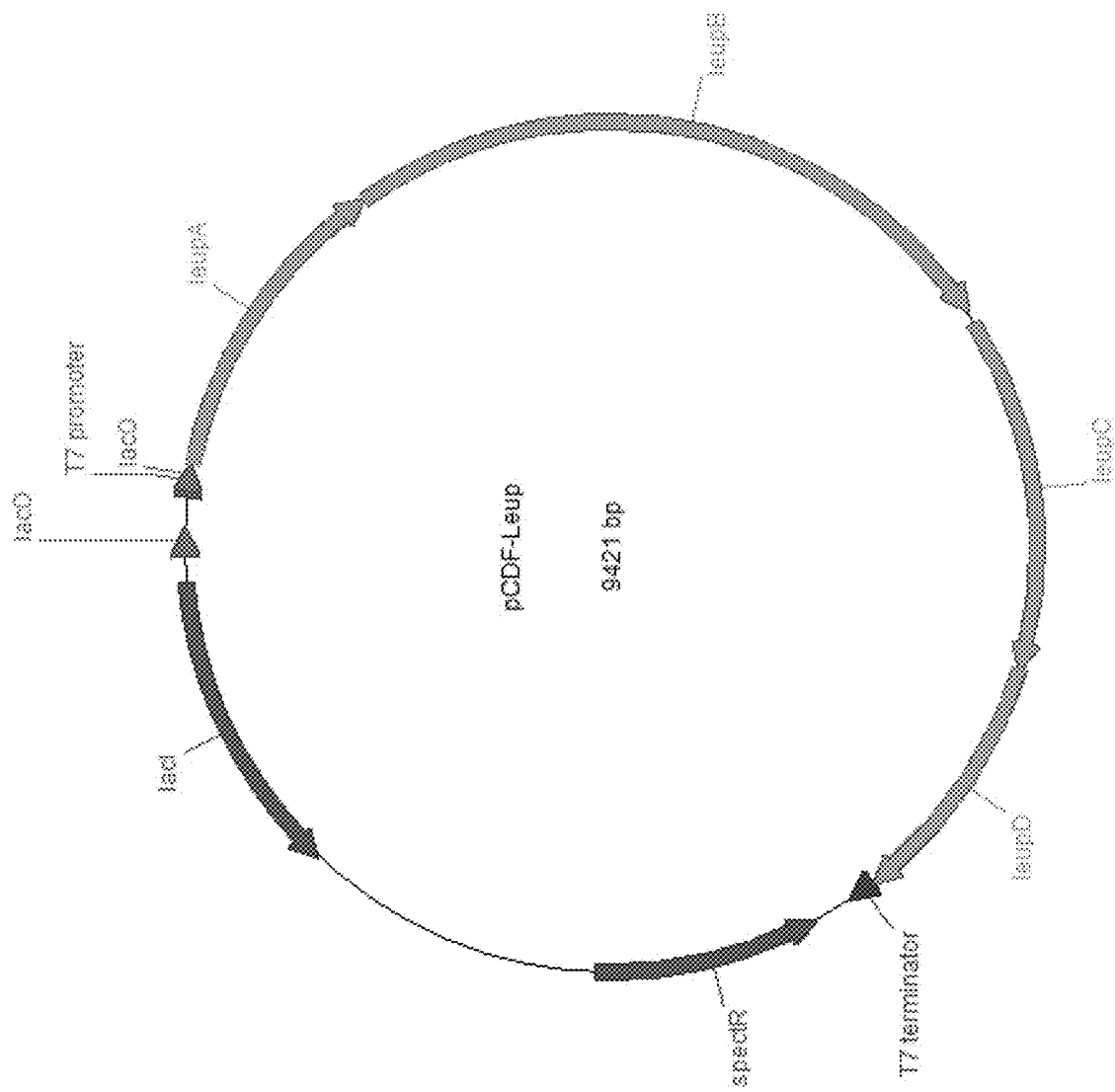
FIG. 7 illustrates a non-limiting construct within the disclosure.

Exemplary Sequences of the Disclosure (See FIG. 7 as Well):

LeupA
(SEQ ID NO: 1)
ATGACTTCTCTTGCTTATGTTGACGCCCTTTGCGCGCTTGATCACCCCTATCGTGCCG

ATAGCGATTGTGACCAACTATTCGATGCGGCTATGCGTGAATTGACACGGTACCATT

GTGAAAACAGCCCCGGTTACCATCAGTGGTTGAAAGTGAATGGTTTGGACGATAAA

AAACTAGAAAAATTGCATGACTGGTCGCGTTTACCACCTATTTTCGCCAATTATTTC

AAACATCAGCTGCTGCTAAGTCACACCGGTATAGATGCGCTGGAATTGACTTCATCT

GGGACAACCGGTCAAAAGAGCCGTATGCGGTACGATACGCGCAGCATACAGGCAGC

CCAGAGAATGGTTGAACGTATTTTCGAATATTACGGCTGGAATACACCACAACAGCC

TTGTAACTACATATTATTGAGCTATGAACCCGCCGGAGCAATTACGCTGGGAACCGC

CTATACCGATCAATATCTGTGTCAGTACGCACCGGTATCGCAAGCTTGTTATGCACT

GCGCCACAATGGAAAAAGCAATGAATTCGACCCATTTGGTGTGATCCGTGCCTTGCA

GGAATTTGCCGCACAAGGGCTGCCAGTGCGTTTCTTAGGCTTCCCGGCCTTCCTCTG

GTTCACGCTGGAACGGATGCGGGAAATGAATTTACCCCCACTACAATTGCATCCCGA

ATCTTTGGTCTTTTTAGGGGGTGGCTGGAAAACCCACGCCGATAAAGCCATTCCACG

ATCGCTGCTGTACCAGCGCTTGAATGAACAACTGGGCATTCCTGATGAACGCTGCCG

GGATGGCTATGGTTCAGTTGAGCATCCTGTACCTTATGTTGAGTGTCAGAATCACCA

TTTTCATGTGCCGTCCTATGCCCGTGCTTATGTCCGTGATACCGCCAATATGGCGGTG

CAATCCTATGGTAAACCGGGTTTTCTGCATCTGACATCACCCTATATCACTTCCAGTC

CAGCACACAGTATCGTGGTGAGCGATTTGGCGGTATTGCATCCCGCCGCAGAGTGTG

GATGTGGATTAGCTACCGATTGGTTTGAACTGCTGGGCCGTGTCGGTACGAGTAAAA

GCCGTAGTTGTGCGATTGCCGCTTCTGAGTTGATTAAGGAATCCTGA

LeupB
(SEQ ID NO: 2)
ATGTATTTAGTTAATGGCGAGGTTATCTCTAACTTGGAACCGGCGGCCGCACTGGCC

GATCTTAAAAACCGTCTTGCCGACGCCTTGGCTTGTCCTCCAACTGTACAAGAAGTG

TTGGATTGCGCCGAGCGTTTTGCCAACAGTCTCAAAACCATGGCAACTGATTTTGCA

CTGGATGCAACCACAATCAGCACGTTACGCCACTTTTGCCATCGTGACGCACTGGAA

GAAAAGCTGCGCCATGAATTGGGAGAACAGCCGTTTTCCCTGCGCCGTTTCGATTAT

ACCCAGCCGCGCTTTGAGACTTGGCAACCTTTGGGGTTGGTGGTGCATATCACTCCG

GCCAACGCACCATTGCTACCATTTATGGCTGTATTGGAAAGTCTGTTAGTTGGCAAT

ATCAACTGGTTGCGCCCCAGTAGCAGTGATAATGGCCTCAATGCACGGATACTGGCT

GAATTTCTGCGCCATGATCTCAGTGGCAAATTAGCGTCTTACGTCTCCGTAATGCCG

CTACCGTCCGATCAATTGTCAGAATTACTTGCCTGTGCCGATGCCGTGTCTGCCTGG

GGCAGCAATGCCGCATTGACGGCTATCCGCAGCCAGTTACGACCAGGTTGCCGCTG

GATCGATTGGGGCATCGCATCAGTTTTGCCTATCTCGACCCGATAGCAGCCAGCAA

CGCTGACTACGATGCCCTGGCTGATGATGTTTGCCGTTTTGATCAACAGGCTTGTTCC

AGCCCGCAGTGCCTGTTGGTAGATAGTACCGACGAGAATGTTTTGCGCGAAGTGGCT

GATGCCGTGGCTTCGGCACTGGAACGACGCGCACCGGTATGGCCGGCCTTACAGCC

AGATATCCAAGAAGCGGCTGAAATCAGCAGTCAGATGGCATTTCTGCGCTTGGATC

ACACGTTTGCCGACGTTGCCGGTTCGGTAACTGAAGGCACAGGATGGCGGGTCGCG

-continued

```
TGGACGCAACGTCAGGAACTGGCGGCATCTCCACTGTACCGTACTCTGCAAATTCGT

CCTGTGCCGCGTGCGCAGTTGATCAACGTATTGCTGCCGTGGCGCCCCTATTTACAG

AGTTGTGGTTTGATCGCCGGAGAACACGAATTGCCGGCCTTGAGCCGTCAGTTGCTG

GCGGCGGGTGTCAGCCGGATATGTCAGGCCGGCGCTATGCATGAGGGTTATGAAGG

AGAACCTCATGATGGAGTTTATGCATTGACGCGGCTTGCACGCAGGGTCTCAGTCAG

TGTGAAAGCTGAACAACTGCCAAACCATGTCACGCTGGATAAATTATCCATCAGGCC

GCCGGATCTGGCAGGGCTGCCAATCATGGGCAAAGAACAGTTTCAGCAAAGTGGCA

CGACACCGAAAGCACAAGTGTTTTTCCGCAGTGGCGGGAGTACAGGAGCGCCAAAA

TTAGCGGGATTCAGTCATAGAGATTATCACATCCAAATGCAAGCAGCGGCAGATGG

CCTATTTTCCGCCGGTCTCGATCCGGCACAGGATCGCGTCATTAATCTCCTGTACGG

CGGCAATTTGTATGGTGGCCTACTTAGCTTTTTCACTGTTCTGGATAAATTGTCCGTG

CCGCATTACCCGATGGGTGGCCCGATAGACGACGATTTTAGCCAGATCCTACAAGTT

ATTGTCACGCAAGGCGTTAATACGTTGGTAGGAATGCCAAGCACGATATATCAGCTG

TTTGAACGTGAAGAGGCCGCGTTACGCGCTTATGGTGGTGTGCGCAAAATTTTCGCC

GGTGGTGAGCATGTCAGTGAAGAACGGCGTCAATTCTTATCCAGTTTTGGCGTGCAG

GTGATCCGTTCAGCAATTTACGGTTCCGTTGATGCGGGCCCATTGGGTCATGCTTGC

ACTTGTTGCAACGAGGGCGAATTCCATCTGTTATCTGATATTCAGTGGCTGGAAATA

TTAGATCTGGACAGCGAACAACCTGTTCAGTCAGGCGAGACAGGTCGGCTGGTGTTT

ACCCCTCTGGCACGGGAAGGACAAGTCGTTCAACGCTATGAGGTGGGCGATTTAGG

CCACTGGTTATCGGAACCTTGTACCTGCGGATTATCGACACCACGCTTTAGACTGGA

AGGCCGACATGGTGGATTGATACGGGTAGGTTCTATTTTTGTGAACCCAACGGCATT

GTCAGCCGATCTGGCGTTTCCGGTGCAATGGTTAGTCGGAAATCTCGATAAGGGTGG

CGAATATATCCATGTGTTGGCTGATGGCGATGTTAACCAGGTACGTCAACATCTACT

GCAACATGAAATGCTGAATCAGGTTGTCAGTGGTGAATTGTTGCAATTGGAAATCAC

GTCTACGCCAGCCGGACAGTTCCGTCGTCATTCCCAAAGTGGCAAGACGCCGTTAGT

GCTGGATTATCGCGTCTGA
```

LeupC
 (SEQ ID NO: 3)
```
ATGACTTTATCATTACACGATCTAGTGGAATACGCCCGTCACCACGCGCCCTTTTTA

GGGATCTTTATAATGATTTGCCACAATCCGGCTGGGCACTAACGGATTTACCTTTAA

TCGATCCTGCTGCTTACTGGCAGCAATCGCAGCCATTGGAGAATTGGCCGGTACTCA

CCGGCCCTATCAACAGTGGCCATATTTTAAAACCGGCGGCTCTACCAGCGAAGGG

AGGTTGTCGGTGTTCAGTCGCAGCGAATGGCAAGCCTTTGTGCGTTCGTTCGGCCAA

GGTCTTGCACAACAATTACAGCCTAGCGACCGTGTTGCCAATCTCTTTTTTGCCGGA

GATCTGTATACCAGCCTGTTGTTTATTCACGGAGCGTTATCTCATTCACCGGTTCCGG

TGGTGGAATATCCGTTTACCTGTTCAGTCGATGATCAGGCGTTGGCTGACGCCATTG

TTAGCTTAGGGATTAATGTACTGGCTGGAGTGCCGGTACAATTGTTGCGTTTTGCCA

GTACCTTGCAGCGTTCAGGCCAGTTTATGCCCAATATTGATCGCCTGTTGTACGGTG

GCGAAAGCCTGTTTCCGGAACAACTGGCTCTTTTGAATACGGTATTTCCCAACGTGT

GCATTGGTTCAATCGGATGTGCCAGTGTTGACGCAGGTCTGATTGGTGCCGCCTCTC

CTGATTGTCACCACGGTGAACATCGGGTTTTTGATGAAGATTCGATTGTCGAAATTA

TTGACGAATCCAATGGTCAGCCCATTACTGAGTCTGGACGCAATGGCATGTTAGTTG
```

```
TTACCAACCTACAACGTCGTCTAATGCCGGTGATCCGCTACCCCACAGGCGATCTGG

CCTGCTGGTGTGAAGAGCCGGGAAGACTGAACCGCAAATTTGCTTTACAGGGTCGG

GCTGGAAGTGCTCACCGGATCCGGGTTTCCACGTTATCCCTGTTTCCCGATCAAATT

GCCCGCTTACTGCAACAACAGAAAGGAATACTGGCTTGGCAGCTATTGTTAAGCCGT

CAGGACGGCATAGATAAGATAAAACTGCTATTAGCCAGCGACTCACCACAGATGCC

ATCAACAGCATCAATCCATCAGGCGTTAGTCACTGCCCAGCCCGCTATGGCAGAACT

CTGTAGCCAAGGGGTGTTACAGGTGGAGGTAGCCTCTTGCGCTCTGGAAAATATGGT

GACGCACCCACGTTCCGGCAAGCTGATACGGGTCGTGGATCATCGTTGTTATAATGC

TGAAGAGAAGACAGCATGA
```

LeupD
                                                    (SEQ ID NO: 4)
```
ATGAATATAAATCCAGTCATGCCGTTGATTCGCTTATTCCGGGAAGAAGATTCCACC

GGAGTCAGCGCGTTGTTTCGAGTCGTTTACGGCGAAGATTACGTCTATCCGGAAGTC

TACCTACCAACCATGCTGAGTCGTTATAATGCGGCCAGACACTGGTATTCTGCCGTT

GCAATACAGGATGGGCAAGTATTGGGACACGCGACATTGTGGCGGAATGGGCGTTG

CCCATCAAGTGCAGAGCTCGCGCTTATCGCGGTACATCCACAAGCGCGCGGACAGG

GTATTGCGACCGCGCTGGGCCGATATTTGTGTGATCAAGCCAAAGAAATGGGATTG

GGTATACTCACGATTAAACAGGTATCGTCGCATAATCACAGCCAGCGTCTGGCTCAA

AATTTGGGCTTTCACACCACGGGTTTATTACCGGATTATGTGACATCTCCCTTTGATC

AAGCACGTCCGGAAAGCATTGTACTCGGTTGCCTGCCTTTGCAACGCTGGCCGTTTC

CAGAATTACACTGGCCGGTAAATTGGCAAACGTGGCTGACATCGGTCACTCAAATAT

TTGGTCAAGAACCGCTAAAACCTGCGGTTCCAATAGATACGGGTATTAGCATCGCCA

GTCATGGTGGCCGATTGGAAGTCTGGATAGAAACGCAGACAACGGAGCGGGTAAAA

GAAGTGACAGAACTGCCGGCGCACAAGCTGATATATGTGAAACTGCCGGTCGGAGA

AGAGACTCTCCACGCGGTACAAATTTTGCAGCAAGCCGGATTTGCCTGCACAGGATT

TGTGCCTGGTCACCATCATCGTTGGGAAGTGCTTCTGGTTCGGGGACATAGCAGAAA

AGAACTGGCTCTAAGTTGCCAGTTTGCCCACAATCTACATCAGCAAAGTCTGTTTGC

CTGTGCCGAAAGGTAA
``` pCDF-Leup Construct
                                                    (SEQ ID NO: 5)
```
ggggaattgtgagcggataacaattcccctgtagaaataattttgtttaactttaata aggagatataccatgggcagcagccatcaccatcatcaccacagccaggatccgaatt cgagctcggcgcgcctgcaggtcgacaagcttgcggccgcataatgcttaagtcgaac agaaagtaatcgtattgtacacggccgcataatcgaaattaatacgactcactatagg ggaattgtgagcggataacaattccccatcttagtatattagttaagtataagaagg agatatacatatgACTTCTCTTGCTTATGTTGACGCCCTTTGCGCGCTTGATCACCC

CTATCGTGCCGATAGCGATTGTGACCAACTATTCGATGCGGCTATGCGTGAATTGAC

ACGGTACCATTGTGAAAACAGCCCCGGTTACCATCAGTGGTTGAAAGTGAATGGTTT

GGACGATAAAAAACTAGAAAAATTGCATGACTGGTCGCGTTTACCACCTATTTTCGC

CAATTATTTCAAACATCAGCTGCTGCTAAGTCACACCGGTATAGATGCGCTGGAATT

GACTTCATCTGGGACAACCGGTCAAAAGAGCCGTATGCGGTACGATACGCGCAGCA

TACAGGCAGCCCAGAGAATGGTTGAACGTATTTTCGAATATTACGGCTGGAATACAC
```

-continued

```
CACAACAGCCTTGTAACTACATATTATTGAGCTATGAACCCGCCGGAGCAATTACGC

TGGGAACCGCCTATACCGATCAATATCTGTGTCAGTACGCACCGGTATCGCAAGCTT

GTTATGCACTGCGCCACAATGGAAAAAGCAATGAATTCGACCCATTTGGTGTGATCC

GTGCCTTGCAGGAATTTGCCGCACAAGGGCTGCCAGTGCGTTTCTTAGGCTTCCCGG

CCTTCCTCTGGTTCACGCTGGAACGGATGCGGGAAATGAATTTACCCCCACTACAAT

TGCATCCCGAATCTTTGGTCTTTTTAGGGGGTGGCTGGAAAACCCACGCCGATAAAG

CCATTCCACGATCGCTGCTGTACCAGCGCTTGAATGAACAACTGGGCATTCCTGATG

AACGCTGCCGGGATGGCTATGGTTCAGTTGAGCATCCTGTACCTTATGTTGAGTGTC

AGAATCACCATTTTCATGTGCCGTCCTATGCCCGTGCTTATGTCCGTGATACCGCCAA

TATGGCGGTGCAATCCTATGGTAAACCGGGTTTTCTGCATCTGACATCACCCTATAT

CACTTCCAGTCCAGCACACAGTATCGTGGTGAGCGATTTGGCGGTATTGCATCCCGC

CGCAGAGTGTGGATGTGGATTAGCTACCGATTGGTTTGAACTGCTGGGCCGTGTCGG

TACGAGTAAAAGCCGTAGTTGTGCGATTGCCGCTTCTGAGTTGATTAAGGAATCCTG

AAATGTATTTAGTTAATGGCGAGGTTATCTCTAACTTGGAACCGGCGGCCGCACTGG

CCGATCTTAAAAACCGTCTTGCCGACGCCTTGGCTTGTCCTCCAACTGTACAAGAAG

TGTTGGATTGCGCCGAGCGTTTTGCCAACAGTCTCAAAACCATGGCAACTGATTTTG

CACTGGATGCAACCACAATCAGCACGTTACGCCACTTTTGCCATCGTGACGCACTGG

AAGAAAAGCTGCGCCATGAATTGGGAGAACAGCCGTTTTCCCTGCGCCGTTTCGATT

ATACCCAGCCGCGCTTTGAGACTTGGCAACCTTTGGGGTTGGTGGTGCATATCACTC

CGGCCAACGCACCATTGCTACCATTTATGGCTGTATTGGAAAGTCTGTTAGTTGGCA

ATATCAACTGGTTGCGCCCCAGTAGCAGTGATAATGGCCTCAATGCACGGATACTGG

CTGAATTTCTGCGCCATGATCTCAGTGGCAAATTAGCGTCTTACGTCTCCGTAATGCC

GCTACCGTCCGATCAATTGTCAGAATTACTTGCCTGTGCCGATGCCGTGTCTGCCTG

GGGCAGCAATGCCGCATTGACGGCTATCCGCAGCCAGTTACGACCAGGTTGCCGCT

GGATCGATTGGGGGCATCGCATCAGTTTTGCCTATCTCGACCCGATAGCAGCCAGCA

ACGCTGACTACGATGCCCTGGCTGATGATGTTTGCCGTTTTGATCAACAGGCTTGTTC

CAGCCCGCAGTGCCTGTTGGTAGATAGTACCGACGAGAATGTTTTGCGCGAAGTGGC

TGATGCCGTGGCTTCGGCACTGGAACGACGCGCACCGGTATGGCCGGCCTTACAGC

CAGATATCCAAGAAGCGGCTGAAATCAGCAGTCAGATGGCATTTCTGCGCTTGGATC

ACACGTTTGCCGACGTTGCCGGTTCGGTAACTGAAGGCACAGGATGGCGGGTCGCG

TGGACGCAACGTCAGGAACTGGCGGCATCTCCACTGTACCGTACTCTGCAAATTCGT

CCTGTGCCGCGTGCGCAGTTGATCAACGTATTGCTGCCGTGGCGCCCCTATTTACAG

AGTTGTGGTTTGATCGCCGGAGAACACGAATTGCCGGCCTTGAGCCGTCAGTTGCTG

GCGGCGGGTGTCAGCCGGATATGTCAGGCCGGCGCTATGCATGAGGGTTATGAAGG

AGAACCTCATGATGGAGTTTATGCATTGACGCGGCTTGCACGCAGGGTCTCAGTCAG

TGTGAAAGCTGAACAACTGCCAAACCATGTCACGCTGGATAAATTATCCATCAGGCC

GCCGGATCTGGCAGGGCTGCCAATCATGGGCAAAGAACAGTTTCAGCAAAGTGGCA

CGACACCGAAAGCACAAGTGTTTTTCCGCAGTGGCGGGAGTACAGGAGCGCCAAAA

TTAGCGGGATTCAGTCATAGAGATTATCACATCCAAATGCAAGCAGCGGCAGATGG

CCTATTTTCCGCCGGTCTCGATCCGGCACAGGATCGCGTCATTAATCTCCTGTACGG

CGGCAATTTGTATGGTGGCCTACTTAGCTTTTTCACTGTTCTGGATAAATTGTCCGTG
```

-continued

```
CCGCATTACCCGATGGGTGGCCCGATAGACGACGATTTTAGCCAGATCCTACAAGTT

ATTGTCACGCAAGGCGTTAATACGTTGGTAGGAATGCCAAGCACGATATATCAGCTG

TTTGAACGTGAAGAGGCCGCGTTACGCGCTTATGGTGGTGTGCGCAAAATTTTCGCC

GGTGGTGAGCATGTCAGTGAAGAACGGCGTCAATTCTTATCCAGTTTTGGCGTGCAG

GTGATCCGTTCAGCAATTTACGGTTCCGTTGATGCGGGCCCATTGGGTCATGCTTGC

ACTTGTTGCAACGAGGGCGAATTCCATCTGTTATCTGATATTCAGTGGCTGGAAATA

TTAGATCTGGACAGCGAACAACCTGTTCAGTCAGGCGAGACAGGTCGGCTGGTGTTT

ACCCCTCTGGCACGGGAAGGACAAGTCGTTCAACGCTATGAGGTGGGCGATTTAGG

CCACTGGTTATCGGAACCTTGTACCTGCGGATTATCGACACCACGCTTTAGACTGGA

AGGCCGACATGGTGGATTGATACGGGTAGGTTCTATTTTTGTGAACCCAACGGCATT

GTCAGCCGATCTGGCGTTTCCGGTGCAATGGTTAGTCGGAAATCTCGATAAGGGTGG

CGAATATATCCATGTGTTGGCTGATGGCGATGTTAACCAGGTACGTCAACATCTACT

GCAACATGAAATGCTGAATCAGGTTGTCAGTGGTGAATTGTTGCAATTGGAAATCAC

GTCTACGCCAGCCGGACAGTTCCGTCGTCATTCCCAAAGTGGCAAGACGCCGTTAGT

GCTGGATTATCGCGTCTGAAACAATATACCCAATAGATTTCAAAACGACTTTTGAGC

TAATCATGACTTTATCATTACACGATCTAGTGGAATACGCCCGTCACCACGCGCCCT

TTTTTAGGGATCTTTATAATGATTTGCCACAATCCGGCTGGGCACTAACGGATTTACC

TTTAATCGATCCTGCTGCTTACTGGCAGCAATCGCAGCCATTGGAGAATTGGCCGGT

ACTCACCGGCCCTATCAACAGTGGCCATATTTTTAAAACCGGCGGCTCTACCAGCGA

AGGGAGGTTGTCGGTGTTCAGTCGCAGCGAATGGCAAGCCTTTGTGCGTTCGTTCGG

CCAAGGTCTTGCACAACAATTACAGCCTAGCGACCGTGTTGCCAATCTCTTTTTTGCC

GGAGATCTGTATACCAGCCTGTTGTTTATTCACGGAGCGTTATCTCATTCACCGGTTC

CGGTGGTGGAATATCCGTTTACCTGTTCAGTCGATGATCAGGCGTTGGCTGACGCCA

TTGTTAGCTTAGGGATTAATGTACTGGCTGGAGTGCCGGTACAATTGTTGCGTTTTGC

CAGTACCTTGCAGCGTTCAGGCCAGTTTATGCCCAATATTGATCGCCTGTTGTACGG

TGGCGAAAGCCTGTTTCCGGAACAACTGGCTCTTTTGAATACGGTATTTCCCAACGT

GTGCATTGGTTCAATCGGATGTGCCAGTGTTGACGCAGGTCTGATTGGTGCCGCCTC

TCCTGATTGTCACCACGGTGAACATCGGGTTTTTGATGAAGATTCGATTGTCGAAAT

TATTGACGAATCCAATGGTCAGCCCATTACTGAGTCTGGACGCAATGGCATGTTAGT

TGTTACCAACCTACAACGTCGTCTAATGCCGGTGATCCGCTACCCCACAGGCGATCT

GGCCTGCTGGTGTGAAGAGCCGGGAAGACTGAACCGCAAATTTGCTTTACAGGGTC

GGGCTGGAAGTGCTCACCGGATCCGGGTTTCCACGTTATCCCTGTTTCCCGATCAAA

TTGCCCGCTTACTGCAACAACAGAAAGGAATACTGGCTTGGCAGCTATTGTTAAGCC

GTCAGGACGGCATAGATAAGATAAAACTGCTATTAGCCAGCGACTCACCACAGATG

CCATCAACAGCATCAATCCATCAGGCGTTAGTCACTGCCCAGCCCGCTATGGCAGAA

CTCTGTAGCCAAGGGGTGTTACAGGTGGAGGTAGCCTCTTGCGCTCTGGAAAATATG

GTGACGCACCCACGTTCCGGCAAGCTGATACGGGTCGTGGATCATCGTTGTTATAAT

GCTGAAGAGAAGACAGCATGAATATAAATCCAGTCATGCCGTTGATTCGCTTATTCC

GGGAAGAAGATTCCACCGGAGTCAGCGCGTTGTTTCGAGTCGTTTACGGCGAAGATT

ACGTCTATCCGGAAGTCTACCTACCAACCATGCTGAGTCGTTATAATGCGGCCAGAC
```

```
ACTGGTATTCTGCCGTTGCAATACAGGATGGGCAAGTATTGGGACACGCGACATTGT

GGCGGAATGGGCGTTGCCCATCAAGTGCAGAGCTCGCGCTTATCGCGGTACATCCA

CAAGCGCGCGGACAGGGTATTGCGACCGCGCTGGGCCGATATTTGTGTGATCAAGC

CAAAGAAATGGGATTGGGTATACTCACGATTAAACAGGTATCGTCGCATAATCACA

GCCAGCGTCTGGCTCAAAATTTGGGCTTTCACACCACGGGTTTATTACCGGATTATG

TGACATCTCCCTTTGATCAAGCACGTCCGGAAAGCATTGTACTCGGTTGCCTGCCTTT

GCAACGCTGGCCGTTTCCAGAATTACACTGGCCGGTAAATTGGCAAACGTGGCTGAC

ATCGGTCACTCAAATATTTGGTCAAGAACCGCTAAAACCTGCGGTTCCAATAGATAC

GGGTATTAGCATCGCCAGTCATGGTGGCCGATTGGAAGTCTGGATAGAAACGCAGA

CAACGGAGCGGGTAAAAGAAGTGACAGAACTGCCGGCGCACAAGCTGATATATGTG

AAACTGCCGGTCGGAGAAGAGACTCTCCACGCGGTACAAATTTTGCAGCAAGCCGG

ATTTGCCTGCACAGGATTTGTGCCTGGTCACCATCATCGTTGGGAAGTGCTTCTGGTT

CGGGGACATAGCAGAAAAGAACTGGCTCTAAGTTGCCAGTTTGCCCACAATCTACA

TCAGCAAAGTCTGTTTGCCTGTGCCGAAAGGTAAcctaggctgctgccaccgctgagcaata actagcataacccatggggcctctaaacgggtcttgagggttttttgctgaaacctcaggc atttgagaagcacacggtcacactgatccggtagtcaataaaccggtaaaccagcaatagac ataagcggctatttaacgaccctgccctgaaccgacgaccgggtcatcgtggccggatcttg cggcccctcggcttgaacgaattgttagacattatttgccgactaccttggtgatctcgcat tcacgtagtggacaaattatccaactgatctgcgcgcgaggccaagcgatcttcttcttgtc caagataagcctgtctagcttcaagtatgacgggctgatactgggccggcaggcgctccatt gcccagtcggcagcgacatccttcggcgcgattttgccggttactgcgctgtaccaaatgcg ggacaacgtaagcactacatttcgctcatcgccagcccagtcgggcggcgagttccatagcg ttaaggtttcatttagcgcctcaaatagatcctgttcaggaaccggatcaaagagttcctcc gccgctggacctaccaaggcaacgctatgttctcttgcttttgtcagcaagatagccagatc aatgtcgatcgtggctggctcgaagatacctgcaagaatgtcattgcgctgccattctccaa attgcagttcgcgcttagctggataacgccacggaatgatgtcgtcgtgcacaacaatggtg acttctacagcgcggagaatctcgctctctccaggggaagccgaagtttccaaaaggtcgtt gatcaaagctcgccgcgttgtttcatcaagccttacggtcaccgtaaccagcaaatcaatat cactgtgtggcttcaggccgccatccactgcggagccgtacaaatgtacggccagcaacgtc ggttcgagatggcgctcgatgacgccaactacctctgatagttgagtcgatacttcggcgat caccgctttccctcatactcttcctttttcaatattattgaagcatttatcagggttattgtc tcatgagcggatacatatttgaatgtatttagaaaaataaacaaatagctagctcactcggt cgctacgctccgggcgtgagactgcggcgggcgctgcggacacatacaaagttacccacaga ttccgtggataagcaggggactaacatgtgaggcaaaacagcagggccgcgccggtggcgtt tttccataggctccgccctcctgccagagttcacataaacagacgcttttccggtgcatctg tgggagccgtgaggctcaaccatgaatctgacagtacgggcgaaacccgacaggacttaaag atccccaccgtttccggcgggtcgctccctcttgcgctctcctgttccgaccctgccgttta ccggatacctgttccgcctttctcccttacgggaagtgtggcgctttctcatagctcacaca ctggtatctcggctcggtgtaggtcgttcgctccaagctgggctgtaagcaagaactccccg ttcagcccgactgctgcgccttatccggtaactgttcacttgagtccaacccggaaaagcac ggtaaaacgccactggcagcagccattggtaactgggagttcgcagaggatttgtttagcta
```

-continued

```
aacacgcggttgctcttgaagtgtgcgccaaagtccggctacactggaaggacagatttggt tgctgtgctctgcgaaagccagttaccacggttaagcagttccccaactgacttaaccttcg atcaaaccacctccccaggtggttttttcgtttacagggcaaaagattacgcgcagaaaaaa aggatctcaagaagatcctttgatcttttctactgaaccgctctagatttcagtgcaattta tctcttcaaatgtagcacctgaagtcagccccatacgatataagttgtaattctcatgttag tcatgcccgcgcccaccggaaggagctgactgggttgaaggctctcaagggcatcggtcga gatcccggtgcctaatgagtgagctaacttacattaattgcgttgcgctcactgccgcttt ccagtcgggaaacctgtcgtgccagctgcattaatgaatcggccaacgcgcgggagaggcg gtttgcgtattgggcgccagggtggtttttcttttcaccagtgagacgggcaacagctgatt gcccttcaccgcctggccctgagagagttgcagcaagcggtccacgctggtttgccccagca ggcgaaaatcctgtttgatggtggttaacggcgggatataacatgagctgtcttcggtatcg tcgtatcccactaccgagatgtccgcaccaacgcgcagcccggactcggtaatggcgcgcat tgcgcccagcgccatctgatcgttggcaaccagcatcgcagtgggaacgatgccctcattca gcatttgcatggtttgttgaaaaccggacatggcactccagtcgccttcccgttccgctatc ggctgaatttgattgcgagtgagatatttatgccagccagccagacgcagacgcgccgagac agaacttaatgggcccgctaacagcgcgatttgctggtgacccaatgcgaccagatgctcca cgcccagtcgcgtaccgtcttcatgggagaaaataatactgttgatgggtgtctggtcagag acatcaagaaataacgccggaacattagtgcaggcagcttccacagcaatggcatcctggtc atccagcggatagttaatgatcagcccactgacgcgttgcgcgagaagattgtgcaccgccg ctttacaggcttcgacgccgcttcgttctaccatcgacaccaccacgctggcacccagttga tcggcgcgagatttaatcgccgcgacaatttgcgacggcgcgtgcagggccagactggaggt ggcaacgccaatcagcaacgactgtttgcccgccagttgttgtgccacgcggttgggaatgt aattcagctccgccatcgccgcttccacttttttcccgcgtttcgcagaaacgtggctggcc tggttcaccacgcgggaaacggtctgataagagacaccggcatactctgcgacatcgtataa cgttactggtttcacattcaccaccctgaattgactctcttccgggcgctatcatgccatac cgcgaaaggttttgcgccattcgatggtgtccgggatctcgacgctctcccttatgcgactc ctgcattaggaaattaatacgactcactata
```

TABLE 8

Annotated features of pCDF-Leup (SEQ ID NO: 5)

| Name | Direction | Type | Location |
|---|---|---|---|
| lacO | >>> | Misc_binding | 2 ... 29 |
| T7 promoter | >>> | promoter | 214 ... 232 |
| lacO | >>> | Misc_binding | 233 ... 259 |
| leupA | >>> | gene | 300 ... 1430 |
| leupB | >>> | gene | 1432 ... 3837 |
| leupC | >>> | gene | 3881 ... 5152 |
| leupD | >>> | gene | 5149 ... 6072 |
| T7 terminator | >>> | terminator | 6107 ... 6142 |
| spectR | <<< | gene | Rev: 6320 ... 7111 |
| lacI | <<< | gene | Rev: 8199 ... 9290 |

ENUMERATED EMBODIMENTS

The following enumerated embodiments are provided, the numbering of which is not to be construed as designating levels of importance.

Embodiment 1 provides a construct comprising a leupeptin biosynthesis operon, the operon comprising leupA, leupB, leupC, and leupD genes operably linked to one or more promoters.

Embodiments 2 provides the construct of embodiment 1, wherein the leupeptin biosynthesis operon is derived from a gammaproteobacteria.

Embodiment 3 provides the construct of embodiment 2, wherein the gammaproteobacteria is selected from group consisting of a *Xenorhabdus*, a *Photorhabdus*, and a *Klebsiella*.

Embodiment 4 provides the construct of any one of embodiments 1-3, wherein the gammaproteobacteria is selected from the group consisting of *Bacteriovorax marinus*, *Chromobacterium violaceum*, *Psuedomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperate*, and *Photorhabdus asymbiotica*.

Embodiment 5 provides the construct of any one of embodiments 1-4, wherein the construct comprises the nucleic acid sequence of any one of SEQ ID NOs: 1-5.

Embodiment 6 provides a cell comprising a construct comprising a leupeptin biosynthesis operon, the operon comprising leupA, leupB, leupC, and leupD genes operably linked to a promoter.

Embodiment 7 provides the cell of embodiment 6, wherein the leupeptin biosynthesis operon is derived from a gammaproteobacteria.

Embodiment 8 provides the cell of embodiment 7, wherein the gammaproteobacteria is selected from group consisting of a *Xenorhabdus*, a *Photorhabdus*, and a *Klebsiella*.

Embodiment 9 provides the cell of any one of claims 6-8, wherein the gammaproteobacteria is selected from the group consisting of *Bacteriovorax marinus*, *Chromobacterium violaceum*, *Psuedomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperate*, and *Photorhabdus asymbiotica*.

Embodiment 10 provides the cell of any one of embodiments 6-9, wherein the cell is a bacterial cell.

Embodiment 11 provides the cell of any one of embodiments 6-10, wherein the cell does not comprise an endogenous leupeptin biosynthesis pathway.

Embodiment 12 provides the cell of any one of embodiments 6-11, wherein the construct comprises the nucleic acid sequence of any one of SEQ ID NOs: 1-5.

Embodiment 13 provides a method of producing a leupeptin peptide, the method comprising contacting a bacterial cell with the construct of any one of embodiments 1-5, culturing the bacterial cell, and isolating the leupeptin peptide produced by the bacterial cell.

Embodiment 14 provides the method of embodiment 13, wherein the bacterial cell is *E. coli*.

Embodiment 15 provides the method of any one of embodiments 13-14, wherein the construct is heterologous with respect to the bacterial cell.

Embodiment 16 provides a compound selected from the group consisting of:

Ac-LLV-H

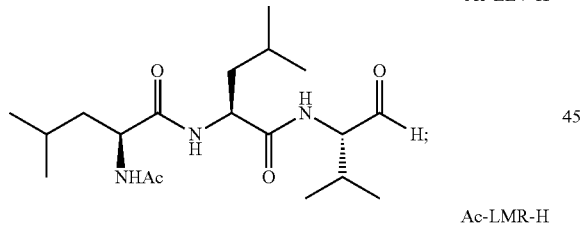

Ac-LMR-H

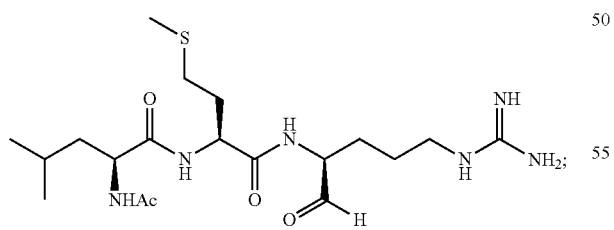

Ac-MLR-H

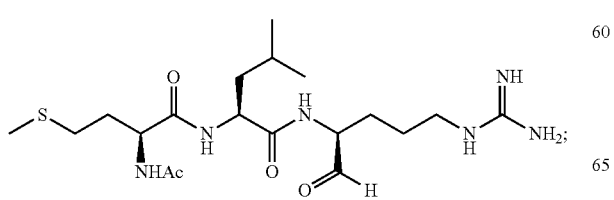

Ac-LMY-H

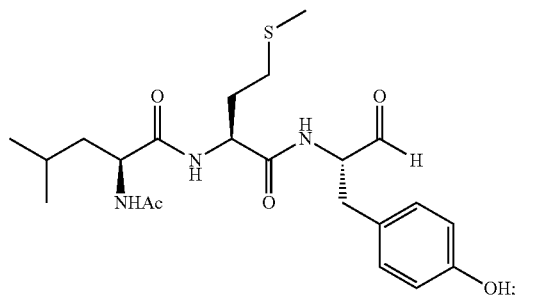

Ac-MLY-H

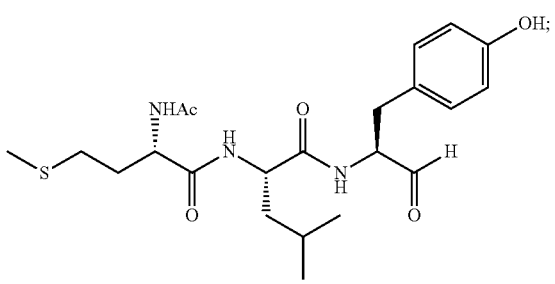

Ac-LMF-H

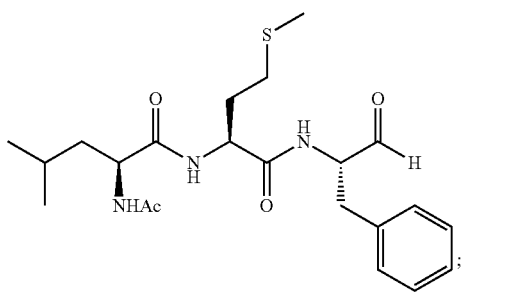

Ac-MLF-H

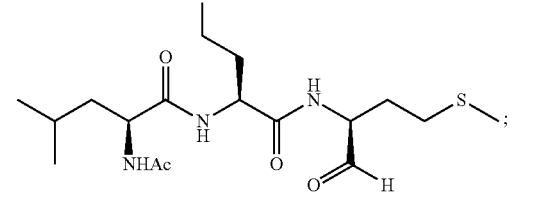

Ac-LMM-H

Ac-LFY-H
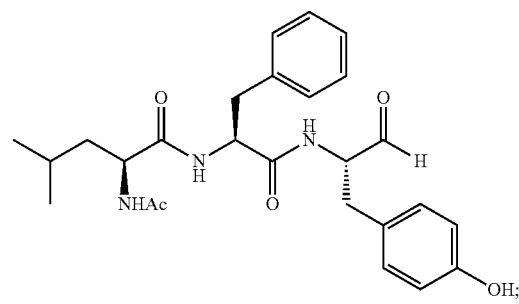
Ac-FLY-H
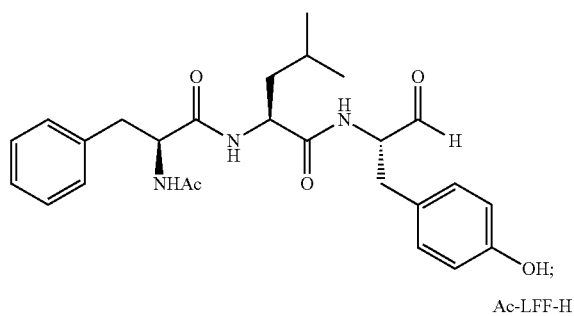
Ac-LFF-H
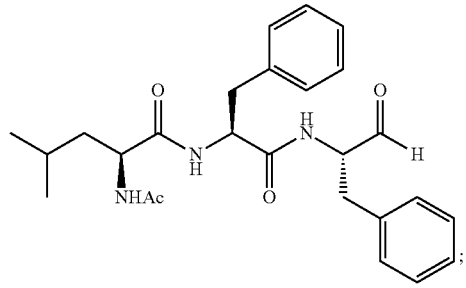
Ac-FLF-H
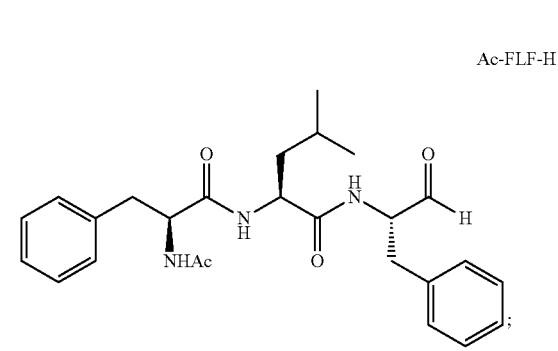
Ac-FMR-H
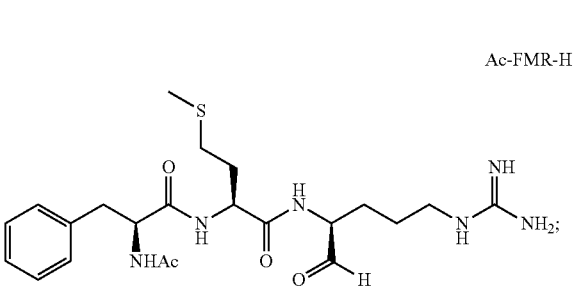
Ac-MFY-H
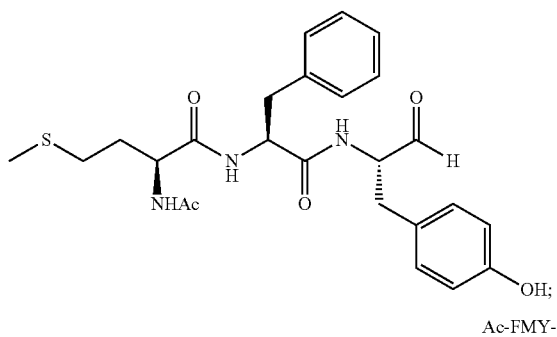
Ac-FMY-H
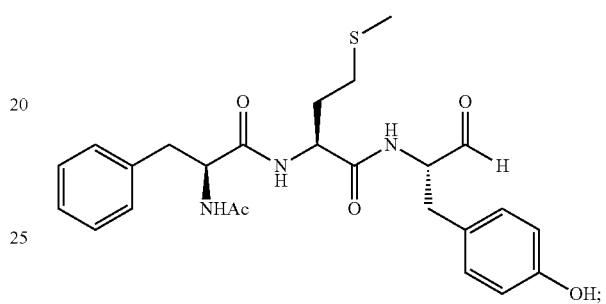
Ac-MFF-H
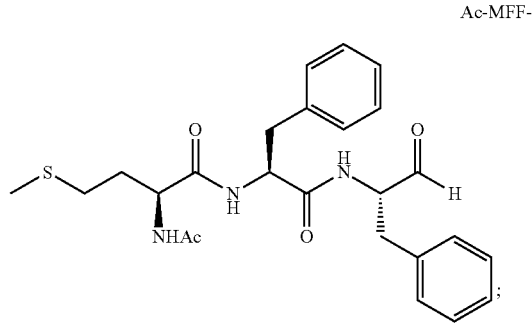
Ac-FMF-H
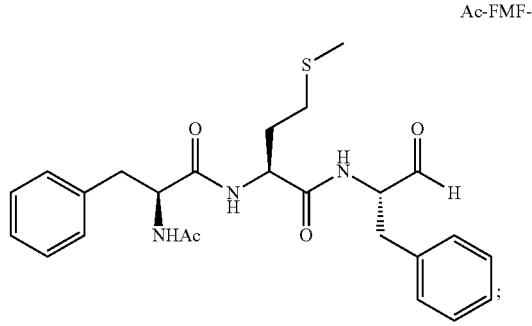
Ac-MMR-H
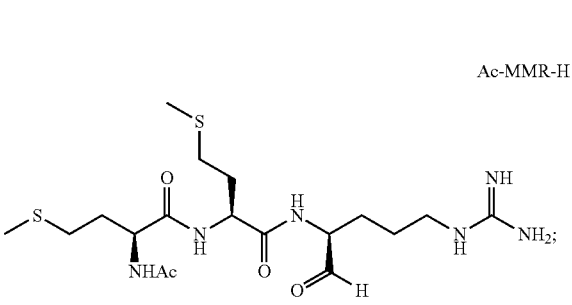

77
-continued

Ac-MMY-H

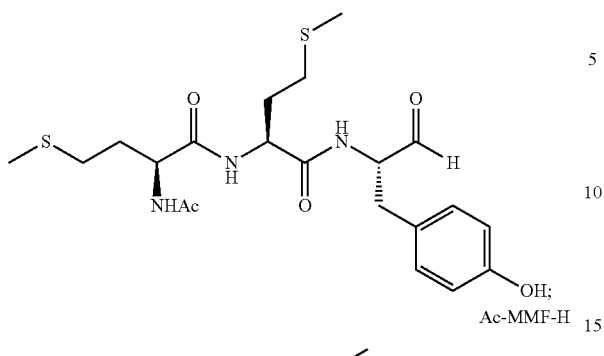

Ac-MMF-H

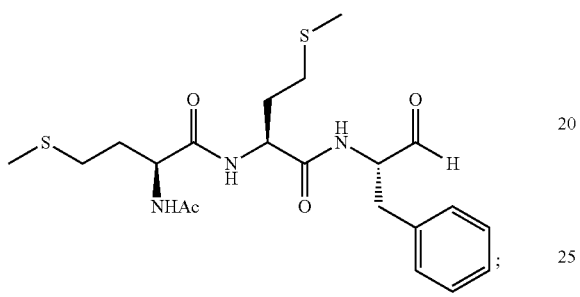

or a salt, solvate, geometric isomer, or stereoisomer thereof.

Embodiment 17 provides A compound selected from the group consisting of:

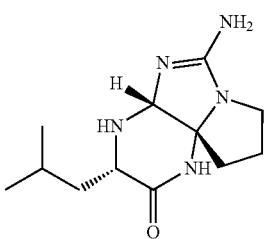

78
-continued

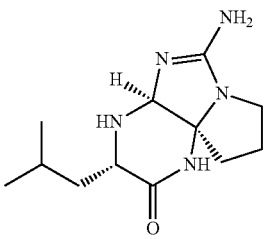

or a salt, solvate, geometric isomer, or stereoisomer thereof.

Embodiment 18 provides a pharmaceutical composition comprising at least one pharmaceutically acceptable carrier and at least one compound of any one of embodiments 16-17.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed is:

1. A heterologous construct comprising a leupeptin biosynthesis operon,
   the operon comprising leupeptin A (leupA), leupeptin B (leupB), leupeptin C (leupC), and leupeptin D (leupD) genes operably linked to one or more promoters,
   wherein the leupeptin biosynthesis operon is derived from a gammaproteobacterium selected from the group consisting of a *Bacteriovorax*, a *Chromobacterium*, a *Pseudomonas*, a *Xenorhabdus*, a *Photorhabdus*, and a *Klebsiella*.

2. The construct of claim 1, wherein the gammaproteobacterium is selected from the group consisting of *Bacteriovorax marinus*, *Chromobacterium violaceum*, *Pseudomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperate*, and *Photorhabdus asymbiotica*.

3. The construct of claim 1, which comprises the nucleic acid sequences of SEQ ID NO 1, SEQ ID NO: 2, SEQ ID NO: 3, and SEQ ID NO: 4.

4. A cell comprising a heterologous construct comprising a leupeptin biosynthesis operon,
   the operon comprising leupeptin A (leupA), leupeptin B (leupB), leupeptin C (leupC), and leupeptin D (leupD) genes operably linked to one or more promoters,
   wherein the leupeptin biosynthesis operon is derived from a gammaproteobacterium selected from the group consisting of a *Bacteriovorax*, a *Chromobacterium*, a *Pseudomonas*, a *Xenorhabdus*, a *Photorhabdus*, and a *Klebsiella*.

5. The cell of claim 4, wherein the gammaproteobacterium is selected from the group consisting of *Bacteriovorax marinus*, *Chromobacterium violaceum*, *Pseudomonas entomophila*, *Pseudomonas fluorescens*, *Klebsiella oxytoca*, *Xenorhabdus nematophila*, *Xenorhabdus bovienii*, *Photorhabdus luminescens*, *Photorhabdus temperate*, and *Photorhabdus asymbiotica*.

6. The cell of claim 4, wherein the cell is a bacterial cell.

7. The cell of claim 4, wherein the cell does not comprise an endogenous leupeptin biosynthesis pathway.

8. The cell of claim 4, wherein the construct comprises the nucleic acid sequences of SEQ ID NO 1, SEQ ID NO: 2, SEQ ID NO: 3, and SEQ ID NO: 4.

* * * * *

SEQUENCE LISTING

```
<160> NUMBER OF SEQ ID NOS: 26

<210> SEQ ID NO 1
<211> LENGTH: 1131
<212> TYPE: DNA
<213> ORGANISM: Artificial Sequence
<220> FEATURE:
<223> OTHER INFORMATION: LeupA

<400> SEQUENCE: 1
atgacttctc ttgcttatgt tgacgccctt tgcgcgcttg atcaccccta tcgtgccgat      60
agcgattgtg accaactatt cgatgcggct atgcgtgaat tgacacggta ccattgtgaa     120
aacagccccg gttaccatca gtggttgaaa gtgaatggtt tggacgataa aaaactagaa     180
aaattgcatg actggtcgcg tttaccacct attttcgcca attatttcaa acatcagctg     240
ctgctaagtc acaccggtat agatgcgctg gaattgactt catctgggac aaccggtcaa     300
aagagccgta tgcggtacga tacgcgcagc atacaggcag cccagagaat ggttgaacgt     360
```

| | |
|---|---|
| attttcgaat attacggctg aatacacca caacagcctt gtaactacat attattgagc | 420 |
| tatgaacccg ccggagcaat tacgctggga accgcctata ccgatcaata tctgtgtcag | 480 |
| tacgcaccgg tatcgcaagc ttgttatgca ctgcgccaca atggaaaaag caatgaattc | 540 |
| gacccatttg gtgtgatccg tgccttgcag gaatttgccg cacaagggct gccagtgcgt | 600 |
| ttcttaggct tcccggcctt cctctggttc acgctggaac ggatgcggga aatgaattta | 660 |
| cccccactac aattgcatcc cgaatctttg gtcttttag ggggtggctg gaaaacccac | 720 |
| gccgataaag ccattccacg atcgctgctg taccagcgct gaatgaaca actgggcatt | 780 |
| cctgatgaac gctgccggga tggctatggt tcagttgagc atcctgtacc ttatgttgag | 840 |
| tgtcagaatc accattttca gtgccgtcc tatgcccgtg cttatgtccg tgataccgcc | 900 |
| aatatggcgg tgcaatccta tggtaaaccg gttttctgc atctgacatc acctatatc | 960 |
| acttccagtc cagcacacag tatcgtggtg agcgatttgg cggtattgca tcccgccgca | 1020 |
| gagtgtggat gtggattagc taccgattgg tttgaactgc tgggccgtgt cggtacgagt | 1080 |
| aaaagccgta gttgtgcgat tgccgcttct gagttgatta aggaatcctg a | 1131 |

<210> SEQ ID NO 2
<211> LENGTH: 2406
<212> TYPE: DNA
<213> ORGANISM: Artificial Sequence
<220> FEATURE:
<223> OTHER INFORMATION: LeupB

<400> SEQUENCE: 2

| | |
|---|---|
| atgtatttag ttaatggcga ggttatctct aacttggaac cggcggccgc actggccgat | 60 |
| cttaaaaacc gtcttgccga cgccttggct tgtcctccaa ctgtacaaga agtgttggat | 120 |
| tgcgccgagc gttttgccaa cagtctcaaa accatggcaa ctgattttgc actggatgca | 180 |
| accacaatca gcacgttacg ccacttttgc catcgtgacg cactggaaga aaagctgcgc | 240 |
| catgaattgg gagaacagcc gttttccctg cgccgtttcg attatacccca gccgcgcttt | 300 |
| gagacttggc aacctttggg gttggtggtg catatcactc cggccaacgc caattgcta | 360 |
| ccatttatgg ctgtattgga aagtctgtta gttggcaata tcaactggtt gcgccccagt | 420 |
| agcagtgata atggcctcaa tgcacggata ctggctgaat ttctgcgcca tgatctcagt | 480 |
| ggcaaattag cgtcttacgt ctccgtaatg ccgctaccgt ccgatcaatt gtcagaatta | 540 |
| cttgcctgtg ccgatgccgt gtctgcctgg ggcagcaatg ccgcattgac ggctatccgc | 600 |
| agccagttac gaccaggttg ccgctggatc gattggggggc atcgcatcag ttttgcctat | 660 |
| ctcgacccga tagcagccag caacgctgac tacgatgccc tggctgatga tgtttgccgt | 720 |
| tttgatcaac aggcttgttc cagcccgcag tgcctgttgg tagatagtac cgacgagaat | 780 |
| gttttgcgcg aagtggctga tgccgtggct tcggcactgg aacgacgcgc accggtatgg | 840 |
| ccggccttac agccagatat ccaagaagcg gctgaaatca gcagtcagat ggcatttctg | 900 |
| cgcttggatc acacgtttgc cgacgttgcc ggttcggtaa ctgaaggcac aggatggcgg | 960 |
| gtcgcgtgga cgcaacgtca ggaactggcg gcatctccac tgtaccgtac tctgcaaatt | 1020 |
| cgtcctgtgc cgcgtgcgca gttgatcaac gtattgctgc cgtggcgccc ctatttacag | 1080 |
| agttgtggtt tgatcgccgg agaacacgaa ttgccggcct tgagccgtca gttgctggcg | 1140 |
| gcgggtgtca gccggatatg tcaggccggc gctatgcatg agggttatga aggagaacct | 1200 |
| catgatggag tttatgcatt gacgcggctt gcacgcaggg tctcagtcag tgtgaaagct | 1260 |

-continued

| | |
|---|---|
| gaacaactgc caaaccatgt cacgctggat aaattatcca tcaggccgcc ggatctggca | 1320 |
| gggctgccaa tcatgggcaa agaacagttt cagcaaagtg gcacgacacc gaaagcacaa | 1380 |
| gtgttttcc gcagtggcgg gagtacagga gcgccaaaat tagcgggatt cagtcataga | 1440 |
| gattatcaca tccaaatgca agcagcggca gatggcctat tttccgccgg tctcgatccg | 1500 |
| gcacaggatc gcgtcattaa tctcctgtac ggcggcaatt tgtatggtgg cctacttagc | 1560 |
| tttttcactg ttctggataa attgtccgtg ccgcattacc cgatgggtgg cccgatagac | 1620 |
| gacgatttta gccagatcct acaagttatt gtcacgcaag gcgttaatac gttggtagga | 1680 |
| atgccaagca cgatatatca gctgtttgaa cgtgaagagg ccgcgttacg cgcttatggt | 1740 |
| ggtgtgcgca aaattttcgc cggtggtgag catgtcagtg aagaacggcg tcaattctta | 1800 |
| tccagttttg gcgtgcaggt gatccgttca gcaatttacg gttccgttga tgcgggccca | 1860 |
| ttgggtcatg cttgcacttg ttgcaacgag ggcgaattcc atctgttatc tgatattcag | 1920 |
| tggctggaaa tattagatct ggacagcgaa caacctgttc agtcaggcga acaggtcgg | 1980 |
| ctggtgttta cccctctggc acgggaagga caagtcgttc aacgctatga ggtgggcgat | 2040 |
| ttaggccact ggttatcgga accttgtacc tgcggattat cgacaccacg ctttagactg | 2100 |
| gaaggccgac atggtggatt gatacgggta ggttctattt ttgtgaaccc aacggcattg | 2160 |
| tcagccgatc tggcgtttcc ggtgcaatgg ttagtcggaa atctcgataa gggtggcgaa | 2220 |
| tatatccatg tgttggctga tggcgatgtt aaccaggtac gtcaacatct actgcaacat | 2280 |
| gaaatgctga atcaggttgt cagtggtgaa ttgttgcaat ggaaatcac gtctacgcca | 2340 |
| gccggacagt tccgtcgtca ttcccaaagt ggcaagacgc cgttagtgct ggattatcgc | 2400 |
| gtctga | 2406 |

<210> SEQ ID NO 3
<211> LENGTH: 1272
<212> TYPE: DNA
<213> ORGANISM: Artificial Sequence
<220> FEATURE:
<223> OTHER INFORMATION: LeupC

<400> SEQUENCE: 3

| | |
|---|---|
| atgactttat cattacacga tctagtggaa tacgcccgtc accacgcgcc ctttttagg | 60 |
| gatctttata tgatttgcc acaatccggc tgggcactaa cggatttacc tttaatcgat | 120 |
| cctgctgctt actggcagca atcgcagcca ttggagaatt ggccggtact caccggccct | 180 |
| atcaacagtg gccatatttt taaaaccggc ggctctacca gcgaagggag gttgtcggtg | 240 |
| ttcagtcgca gcgaatggca agcctttgtg cgttcgttcg gccaaggtct tgcacaacaa | 300 |
| ttacagccta gcgaccgtgt tgccaatctc ttttttgccg gagatctgta taccagcctg | 360 |
| ttgtttattc acggagcgtt atctcattca ccggttccgg tggtggaata tccgtttacc | 420 |
| tgttcagtcg atgatcaggc gttggctgac gccattgtta gcttagggat taatgtactg | 480 |
| gctggagtgc cggtacaatt gttgcgtttt gccagtacct tgcagcgttc aggccagttt | 540 |
| atgcccaata ttgatcgcct gttgtacggt ggcgaaagcc tgtttccgga caactggct | 600 |
| cttttgaata cggtatttcc caacgtgtgc attggttcaa tcggatgtgc cagtgttgac | 660 |
| gcaggtctga ttggtgccgc ctctcctgat tgtcaccacg gtgaacatcg gttttttgat | 720 |
| gaagattcga ttgtcgaaat tattgacgaa tccaatggtc agcccattac tgagtctgga | 780 |
| cgcaatggca tgttagttgt taccaaccta aacgtcgtc taatgccggt gatccgctac | 840 |
| cccacaggcg atctggcctg ctggtgtgaa gagccgggaa gactgaaccg caaatttgct | 900 |

| | | |
|---|---|---|
| ttacagggtc gggctggaag tgctcaccgg atccgggttt ccacgttatc cctgtttccc | 960 |
| gatcaaattg cccgcttact gcaacaacag aaaggaatac tggcttggca gctattgtta | 1020 |
| agccgtcagg acggcataga taagataaaa ctgctattag ccagcgactc accacagatg | 1080 |
| ccatcaacag catcaatcca tcaggcgtta gtcactgccc agcccgctat ggcagaactc | 1140 |
| tgtagccaag gggtgttaca ggtggaggta gcctcttgcg ctctggaaaa tatggtgacg | 1200 |
| cacccacgtt ccggcaagct gatacgggtc gtggatcatc gttgttataa tgctgaagag | 1260 |
| aagacagcat ga | 1272 |

<210> SEQ ID NO 4
<211> LENGTH: 924
<212> TYPE: DNA
<213> ORGANISM: Artificial Sequence
<220> FEATURE:
<223> OTHER INFORMATION: LeupD

<400> SEQUENCE: 4

| | | |
|---|---|---|
| atgaatataa atccagtcat gccgttgatt cgcttattcc gggaagaaga ttccaccgga | 60 |
| gtcagcgcgt tgtttcgagt cgtttacggc gaagattacg tctatccgga agtctaccta | 120 |
| ccaaccatgc tgagtcgtta taatgcggcc agacactggt attctgccgt tgcaatacag | 180 |
| gatgggcaag tattgggaca cgcgacattg tggcggaatg ggcgttgccc atcaagtgca | 240 |
| gagctcgcgc ttatcgcggt acatccacaa gcgcgcggac agggtattgc gaccgcgctg | 300 |
| ggccgatatt tgtgtgatca agccaaagaa atgggattgg gtatactcac gattaaacag | 360 |
| gtatcgtcgc ataatcacag ccagcgtctg gctcaaaatt gggctttca caccacgggt | 420 |
| ttattaccgg attatgtgac atctcccttt gatcaagcac gtccggaaag cattgtactc | 480 |
| ggttgcctgc ctttgcaacg ctggccgttt ccagaattac actggccggt aaattggcaa | 540 |
| acgtggctga catcggtcac tcaaatattt ggtcaagaac cgctaaaacc tgcggttcca | 600 |
| atagatacgg tattagcat cgccagtcat ggtggccgat tggaagtctg gatagaaacg | 660 |
| cagacaacgg agcgggtaaa agaagtgaca gaactgccgg cgcacaagct gatatatgtg | 720 |
| aaaactgccgg tcggagaaga gactctccac gcggtacaaa ttttgcagca agccggattt | 780 |
| gcctgcacag gatttgtgcc tggtcaccat catcgttggg aagtgcttct ggttcgggga | 840 |
| catagcagaa aagaactggc tctaagttgc agtttgccc acaatctaca tcagcaaagt | 900 |
| ctgtttgcct gtgccgaaag gtaa | 924 |

<210> SEQ ID NO 5
<211> LENGTH: 9421
<212> TYPE: DNA
<213> ORGANISM: Artificial Sequence
<220> FEATURE:
<223> OTHER INFORMATION: pCDF-Leup Construct

<400> SEQUENCE: 5

| | | |
|---|---|---|
| ggggaattgt gagcggataa caattcccct gtagaaataa ttttgtttaa ctttaataag | 60 |
| gagatatacc atgggcagca gccatcacca tcatcaccac agccaggatc cgaattcgag | 120 |
| ctcggcgcgc ctgcaggtcg acaagcttgc ggccgcataa tgcttaagtc gaacagaaag | 180 |
| taatcgtatt gtacacggcc gcataatcga attaatacg actcactata ggggaattgt | 240 |
| gagcggataa caattcccca tcttagtata ttagttaagt ataagaagga gatatacata | 300 |
| tgacttctct tgcttatgtt gacgccctt gcgcgcttga tcaccctat cgtgccgata | 360 |

```
gcgattgtga ccaactattc gatgcggcta tgcgtgaatt gacacggtac cattgtgaaa      420
acagccccgg ttaccatcag tggttgaaag tgaatggttt ggacgataaa aaactagaaa      480
aattgcatga ctggtcgcgt ttaccaccta ttttcgccaa ttatttcaaa catcagctgc      540
tgctaagtca caccggtata gatgcgctgg aattgacttc atctgggaca accggtcaaa      600
agagccgtat gcggtacgat acgcgcagca tacaggcagc ccagagaatg gttgaacgta      660
ttttcgaata ttacgctgg  aatacaccac aacagccttg taactacata ttattgagct      720
atgaacccgc cggagcaatt acgctgggaa ccgcctatac cgatcaatat ctgtgtcagt      780
acgcaccggt atcgcaagct tgttatgcac tgcgccacaa tggaaaaagc aatgaattcg      840
acccatttgg tgtgatccgt gccttgcagg aatttgccgc acaagggctg ccagtgcgtt      900
tcttaggctt cccggccttc ctctggttca cgctggaacg gatgcgggaa atgaatttac      960
ccccactaca attgcatccc gaatctttgg tcttttttagg gggtggctgg aaaacccacg     1020
ccgataaagc cattccacga tcgctgctgt accagcgctt gaatgaacaa ctgggcattc     1080
ctgatgaacg ctgccgggat ggctatggtt cagttgcagca tcctgtacct tatgttgagt    1140
gtcagaatca ccattttcat gtgccgtcct atgcccgtgc ttatgtccgt gataccgcca     1200
atatggcggt gcaatcctat ggtaaaccgg ttttctgca  tctgacatca ccctatatca     1260
cttccagtcc agcacacagt atcgtggtga gcgatttggc ggtattgcat cccgccgcag     1320
agtgtggatg tggattagct accgattggt ttgaactgct gggccgtgtc ggtacgagta     1380
aaagccgtag ttgtgcgatt gccgcttctg agttgattaa ggaatcctga aatgtattta     1440
gttaatggcg aggttatctc taacttggaa ccggcggccg cactggccga tcttaaaaac     1500
cgtcttgccg acgccttggc ttgtcctcca actgtacaag aagtgttgga ttgcgccgag     1560
cgttttgcca acagtctcaa aaccatggca actgattttg cactggatgc aaccacaatc     1620
agcacgttac gccacttttg ccatcgtgac gcactggaag aaaagctgcg ccatgaattg     1680
ggagaacagc cgttttccct gcgccgtttc gattataccc agccgcgctt tgagacttgg     1740
caacctttgg ggttggtggt gcatatcact ccggccaacg caccattgct accattttatg    1800 gctgtattgg aaagtctgtt agttggcaat atcaactggt tgcgccccag tagcagtgat    1860
aatggcctca atgcacggat actggctgaa tttctgcgcc atgatctcag tggcaaatta     1920
gcgtcttacg tctccgtaat gccgctaccg tccgatcaat tgtcagaatt acttgcctgt    1980
gccgatgccg tgtctgcctg ggcagcaat  gccgcattga cggctatccg cagccagtta    2040
cgaccaggtt gccgctggat cgattggggg catcgcatca gttttgccta tctcgacccg    2100
atagcagcca gcaacgctga ctacgatgcc ctggctgatg atgtttgccg ttttgatcaa    2160
caggcttgtt ccagcccgca gtgcctgttg gtagatagta ccgacgagaa tgttttgcgc    2220
gaagtggctg atgccgtggc ttcggcactg gaacgacgcg caccggtatg gccggcctta    2280
cagccagata tccaagaagc ggctgaaatc agcagtcaga tggcatttct gcgcttggat    2340
cacacgtttg ccgacgttgc cggttcggta actgaaggca caggatggcg ggtcgcgtgg    2400
acgcaacgtc aggaactggc ggcatctcca ctgtaccgta ctctgcaaat tcgtcctgtg    2460
ccgcgtgcgc agttgatcaa cgtattgctg ccgtggcgcc cctatttaca gagttgtggt    2520
ttgatcgccg gagaacacga attgccggcc ttgagccgtc agttgctggc ggcgggtgtc    2580
agccggatat gtcaggccgg cgctatgcat gagggttatg aaggagaacc tcatgatgga    2640
gtttatgcat tgacgcggct tgcacgcagg gtctcagtca gtgtgaaagc tgaacaactg    2700
ccaaaccatg tcacgctgga taaattatcc atcaggccgc cggatctggc agggctgcca    2760
```

```
atcatgggca aagaacagtt tcagcaaagt ggcacgacac cgaaagcaca agtgtttttc   2820
cgcagtggcg ggagtacagg agcgccaaaa ttagcgggat tcagtcatag agattatcac   2880
atccaaatgc aagcagcggc agatggccta ttttccgccg gtctcgatcc ggcacaggat   2940
cgcgtcatta atctcctgta cggcggcaat ttgtatggtg gcctacttag cttttttcact  3000 gttctggata aattgtccgt gccgcattac ccgatgggtg gcccgataga cgacgatttt   3060
agccagatcc tacaagttat tgtcacgcaa ggcgttaata cgttggtagg aatgccaagc   3120
acgatatatc agctgtttga acgtgaagag gccgcgttac gcgcttatgg tggtgtgcgc   3180
aaaattttcg ccggtggtga gcatgtcagt gaagaacggc gtcaattctt atccagtttt   3240
ggcgtgcagg tgatccgttc agcaatttac ggttccgttg atgcgggccc attgggtcat   3300
gcttgcactt gttgcaacga gggcgaattc catctgttat ctgatattca gtggctggaa   3360
atattagatc tggacagcga acaacctgtt cagtcaggcg agacaggtcg gctggtgttt   3420
acccctctgg cacgggaagg acaagtcgtt caacgctatg aggtgggcga tttaggccac   3480
tggttatcgg aaccttgtac ctgcggatta tcgacaccac gctttagact ggaaggccga   3540
catggtggat tgatacgggt aggttctatt tttgtgaacc caacggcatt gtcagccgat   3600
ctggcgtttc cggtgcaatg gttagtcgga atctcgata  agggtggcga atatatccat   3660
gtgttggctg atgcgatgt  taaccaggta cgtcaacatc tactgcaaca tgaaatgctg   3720
aatcaggttg tcagtggtga attgttgcaa ttggaaatca cgtctacgcc agccggacag   3780
ttccgtcgtc attcccaaag tggcaagacg ccgttagtgc tggattatcg cgtctgaaac   3840 aatatacccca atagatttca aaacgacttt tgagctaatc atgactttat cattacacga   3900
tctagtggaa tacgcccgtc accacgcgcc cttttttagg gatctttata atgatttgcc   3960
acaatccggc tgggcactaa cggatttacc tttaatcgat cctgctgctt actggcagca   4020
atcgcagcca ttggagaatt ggccggtact caccggccct atcaacagtg gccatatttt   4080
taaaaccggc ggctctacca gcgaagggag gttgtcggtg ttcagtcgca gcgaatggca   4140
agcctttgtg cgttcgttcg gccaaggtct tgcacaacaa ttacagccta gcgaccgtgt   4200
tgccaatctc ttttttgccg gagatctgta taccagcctg ttgtttattc acggagcgtt   4260
atctcattca ccggttccgg tggtggaata tccgtttacc tgttcagtcg atgatcaggc   4320
gttggctgac gccattgtta gcttagggat taatgtactg gctggagtgc cggtacaatt   4380
gttgcgtttt gccagtacct tgcagcgttc aggccagttt atgcccaata ttgatcgcct   4440
gttgtacggt ggcgaaagcc tgtttccgga caactggcct cttttgaata cggtatttcc   4500
caacgtgtgc attggttcaa tcggatgtgc cagtgttgac gcaggtctga ttggtgccgc   4560
ctctcctgat tgtcaccacg gtgaacatcg ggttttgat gaagattcga ttgtcgaaat    4620
tattgacgaa tccaatggtc agcccattac tgagtctgga cgcaatggca tgttagttgt   4680
taccaaccta caacgtcgtc taatgccggt gatccgctac cccacaggcg atctggcctg   4740
ctggtgtgaa gagccgggaa gactgaaccg caaatttgct ttacagggtc gggctggaag   4800
tgctcaccgg atccgggttt ccacgttatc cctgtttccc gatcaaattg cccgcttact   4860
gcaacaacag aaaggaatac tggcttggca gctattgtta agccgtcagg acggcataga   4920
taagataaaa ctgctattag ccagcgactc accacagatg ccatcaacag catcaatcca   4980
tcaggcgtta gtcactgccc agcccgctat ggcagaactc tgtagccaag gggtgttaca   5040
ggtggaggta gcctcttgcg ctctggaaaa tatggtgacg cacccacgtt ccggcaagct   5100
```

```
gatacgggtc gtggatcatc gttgttataa tgctgaagag aagacagcat gaatataaat    5160
ccagtcatgc cgttgattcg cttattccgg gaagaagatt ccaccggagt cagcgcgttg    5220
tttcgagtcg tttacggcga agattacgtc tatccggaag tctacctacc aaccatgctg    5280
agtcgttata tgcggccag acactggtat tctgccgttg caatacagga tgggcaagta    5340
ttgggacacg cgacattgtg gcggaatggg cgttgcccat caagtgcaga gctcgcgctt    5400
atcgcggtac atccacaagc gcgcggacag ggtattgcga ccgcgctggg ccgatatttg    5460
tgtgatcaag ccaaagaaat gggattgggt atactcacga ttaaacaggt atcgtcgcat    5520
aatcacagcc agcgtctggc tcaaaatttg ggctttcaca ccacgggttt attaccggat    5580
tatgtgacat ctcccttga tcaagcacgt ccggaaagca ttgtactcgg ttgcctgcct    5640
ttgcaacgct ggccgtttcc agaattacac tggccggtaa attggcaaac gtggctgaca    5700
tcggtcactc aaatatttgg tcaagaaccg ctaaaacctg cggttccaat agatacgggt    5760
attagcatcg ccagtcatgg tggccgattg gaagtctgga tagaaacgca gacaacggag    5820
cgggtaaaag aagtgacaga actgccggcg cacaagctga tatatgtgaa actgccggtc    5880
ggagaagaga ctctccacgc ggtacaaatt ttgcagcaag ccggatttgc ctgcacagga    5940
tttgtgcctg gtcaccatca tcgttgggaa gtgcttctgg ttcggggaca tagcagaaaa    6000
gaactggctc taagttgcca gtttgcccac aatctacatc agcaaagtct gtttgcctgt    6060
gccgaaaggt aacctaggct gctgccaccg ctgagcaata actagcataa ccccttgggg    6120
cctctaaacg ggtcttgagg ggttttttgc tgaaacctca ggcatttgag aagcacacgg    6180
tcacactgct tccggtagtc aataaaccgg taaaccagca atagacataa gcggctattt    6240
aacgaccctg ccctgaaccg acgaccgggt catcgtggcc ggatcttgcg gcccctcggc    6300
ttgaacgaat tgttagacat tatttgccga ctaccttggt gatctcgcct ttcacgtagt    6360
ggacaaattc ttccaactga tctgcgcgcg aggccaagcg atcttcttct tgtccaagat    6420
aagcctgtct agcttcaagt atgacgggct gatactgggc cggcaggcgc tccattgccc    6480
agtcggcagc gacatccttc ggcgcgattt tgccggttac tgcgctgtac caaatgcggg    6540
acaacgtaag cactacattt cgctcatcgc cagcccagtc gggcggcgag ttccatagcg    6600
ttaaggtttc atttagcgcc tcaaatagat cctgttcagg aaccggatca aagagttcct    6660
ccgccgctgg acctaccaag gcaacgctat gttctcttgc ttttgtcagc aagatagcca    6720
gatcaatgtc gatcgtggct ggctcgaaga tacctgcaag aatgtcattg cgctgccatt    6780
ctccaaattg cagttcgcgc ttagctggat aacgccacgg aatgatgtcg tcgtgcacaa    6840
caatggtgac ttctacagcg cggagaatct cgctctctcc aggggaagcc gaagtttcca    6900
aaaggtcgtt gatcaaagct cgccgcgttg tttcatcaag ccttacggtc accgtaacca    6960
gcaaatcaat atcactgtgt ggcttcaggc cgccatccac tgcggagccg tacaaatgta    7020
cggccagcaa cgtcggttcg agatggcgct cgatgacgcc aactacctct gatagttgag    7080
tcgatacttc ggcgatcacc gcttccctca tactcttcct ttttcaatat tattgaagca    7140
tttatcaggg ttattgtctc atgagcggat acatatttga atgtatttag aaaaataaac    7200
aaatagctag ctcactcggt cgctacgctc cgggcgtgag actgcggcgg gcgctgcgga    7260
cacatacaaa gttacccaca gattccgtgg ataagcaggg gactaacatg tgaggcaaaa    7320
cagcagggcc gcgccggtgg cgttttttcca taggctccgc cctcctgcca gagttcacat    7380
aaacagacgc ttttccggtg catctgtggg agccgtgagg ctcaaccatg aatctgcacag    7440 tacgggcgaa acccgacagg acttaaagat ccccaccgtt tccggcgggt cgctccctct    7500
```

```
tgcgctctcc tgttccgacc ctgccgttta ccggatacct gttccgcctt tctcccttac    7560
gggaagtgtg gcgctttctc atagctcaca cactggtatc tcggctcggt gtaggtcgtt    7620
cgctccaagc tgggctgtaa gcaagaactc cccgttcagc ccgactgctg cgccttatcc    7680
ggtaactgtt cacttgagtc caacccggaa aagcacggta aaacgccact ggcagcagcc    7740
attggtaact gggagttcgc agaggatttg tttagctaaa cacgcggttg ctcttgaagt    7800
gtgcgccaaa gtccggctac actggaagga cagatttggt tgctgtgctc tgcgaaagcc    7860
agttaccacg gttaagcagt tccccaactg acttaacctt cgatcaaacc acctccccag    7920
gtggtttttt cgtttacagg gcaaaagatt acgcgcagaa aaaaggatc tcaagaagat    7980 cctttgatct tttctactga accgctctag atttcagtgc aatttatctc ttcaaatgta    8040
gcacctgaag tcagccccat acgatataag ttgtaattct catgttagtc atgccccgcg    8100
cccaccggaa ggagctgact gggttgaagg ctctcaaggg catcggtcga gatcccggtg    8160
cctaatgagt gagctaactt acattaattg cgttgcgctc actgcccgct ttccagtcgg    8220
gaaacctgtc gtgccagctg cattaatgaa tcggccaacg cgcgggggaga gcggtttgc    8280 gtattgggcg ccagggtggt tttcttttc accagtgaga cggcaacag ctgattgccc    8340 ttcaccgcct ggccctgaga gagttgcagc aagcggtcca cgctggtttg ccccagcagg    8400
cgaaaatcct gtttgatggt ggttaacggc gggatataac atgagctgtc ttcggtatcg    8460
tcgtatccca ctaccgagat gtccgcacca acgcgcagcc cggactcggt aatggcgcgc    8520
attgcgccca cgccatctg atcgttggca accagcatcg cagtgggaac gatgccctca    8580
ttcagcattt gcatggtttg ttgaaaaccg gacatggcac tccagtcgcc ttcccgttcc    8640
gctatcggct gaatttgatt gcgagtgaga tatttatgcc agccagccag acgcagacgc    8700
gccgagacag aacttaatgg gcccgctaac agcgcgattt gctggtgacc caatgcgacc    8760
agatgctcca cgcccagtcg cgtaccgtct tcatgggaga aaataatact gttgatgggt    8820
gtctggtcag agacatcaag aaataacgcc ggaacattag tgcaggcagc ttccacagca    8880
atggcatcct ggtcatccag cggatagtta atgatcagcc cactgacgcg ttgcgcgaga    8940
agattgtgca ccgccgcttt acaggcttcg acgccgcttc gttctaccat cgacaccacc    9000
acgctggcac ccagttgatc ggcgcgagat taatcgccg cgacaatttg cgacggcgcg    9060
tgcagggcca gactggaggt ggcaacgcca atcagcaacg actgtttgcc cgccagttgt    9120
tgtgccacgc ggttgggaat gtaattcagc tccgccatcg ccgcttccac ttttcccgc    9180 gttttcgcag aaacgtggct ggcctggttc accacgcggg aaacggtctg ataagagaca    9240
ccggcatact ctgcgacatc gtataacgtt actggtttca cattcaccac cctgaattga    9300
ctctcttccg ggcgctatca tgccataccg cgaaaggttt tgcgccattc gatggtgtcc    9360
gggatctcga cgctctccct tatgcgactc ctgcattagg aaattaatac gactcactat    9420
a                                                                   9421
```

<210> SEQ ID NO 6
<211> LENGTH: 36
<212> TYPE: DNA
<213> ORGANISM: Artificial Sequence
<220> FEATURE:
<223> OTHER INFORMATION: NdeIfw

<400> SEQUENCE: 6
ctgaaccata tgacttctct tgcttatgtt gacgcc                                36

<210> SEQ ID NO 7
<211> LENGTH: 36
<212> TYPE: DNA
<213> ORGANISM: Artificial Sequence
<220> FEATURE:
<223> OTHER INFORMATION: AvrIIrv

<400> SEQUENCE: 7
ctgaacccta ggttaccttt cggcacaggc aaacag        36

<210> SEQ ID NO 8
<211> LENGTH: 38
<212> TYPE: DNA
<213> ORGANISM: Artificial Sequence
<220> FEATURE:
<223> OTHER INFORMATION: KO1-1

<400> SEQUENCE: 8
gtaaaaaatc atatgtattt agttaatggc gaggttat        38

<210> SEQ ID NO 9
<211> LENGTH: 53
<212> TYPE: DNA
<213> ORGANISM: Artificial Sequence
<220> FEATURE:
<223> OTHER INFORMATION: KO1-2

<400> SEQUENCE: 9
gtaaaaaatc atatgtatat ctccttctta tacttaacta atatactaag atg        53

<210> SEQ ID NO 10
<211> LENGTH: 55
<212> TYPE: DNA
<213> ORGANISM: Artificial Sequence
<220> FEATURE:
<223> OTHER INFORMATION: KO2-1

<400> SEQUENCE: 10
gtaaaaaatt aattaaggag ataccatg actttatcat tacacgatct agtgg        55

<210> SEQ ID NO 11
<211> LENGTH: 41
<212> TYPE: DNA
<213> ORGANISM: Artificial Sequence
<220> FEATURE:
<223> OTHER INFORMATION: KO2-2

<400> SEQUENCE: 11
gtaaaaaatt aattaatcag gattccttaa tcaactcaga a        41

<210> SEQ ID NO 12
<211> LENGTH: 52
<212> TYPE: DNA
<213> ORGANISM: Artificial Sequence
<220> FEATURE:
<223> OTHER INFORMATION: KO3-1

<400> SEQUENCE: 12
gtaaaaaatt aattaaggag ataccatg aatataaatc cagtcatgcc gt        52

<210> SEQ ID NO 13
<211> LENGTH: 38
<212> TYPE: DNA
<213> ORGANISM: Artificial Sequence
<220> FEATURE:
<223> OTHER INFORMATION: KO3-2

<400> SEQUENCE: 13
gtaaaaaatt aattaatcag acgcgataat ccagcact                                  38

<210> SEQ ID NO 14
<211> LENGTH: 26
<212> TYPE: DNA
<213> ORGANISM: Artificial Sequence
<220> FEATURE:
<223> OTHER INFORMATION: KO4-1

<400> SEQUENCE: 14
gtaaaaaatc ctaggctgct gccacc                                               26

<210> SEQ ID NO 15
<211> LENGTH: 47
<212> TYPE: DNA
<213> ORGANISM: Artificial Sequence
<220> FEATURE:
<223> OTHER INFORMATION: KO4-2

<400> SEQUENCE: 15
gtaaaaaatc ctaggtcatg ctgtcttctc ttcagcatta taacaac                        47

<210> SEQ ID NO 16
<211> LENGTH: 37
<212> TYPE: DNA
<213> ORGANISM: Artificial Sequence
<220> FEATURE:
<223> OTHER INFORMATION: NKOXAscI

<400> SEQUENCE: 16
gtaaaaaatg gcgcgcctgg acactttatc ctgcgtc                                   37

<210> SEQ ID NO 17
<211> LENGTH: 38
<212> TYPE: DNA
<213> ORGANISM: Artificial Sequence
<220> FEATURE:
<223> OTHER INFORMATION: CKOXHindIII

<400> SEQUENCE: 17
gtaaaaaata agcttgcgtc agataaaagg gattgtca                                  38

<210> SEQ ID NO 18
<211> LENGTH: 41
<212> TYPE: DNA
<213> ORGANISM: Artificial Sequence
<220> FEATURE:
<223> OTHER INFORMATION: 4509NdeIfw

<400> SEQUENCE: 18
ctgaaccata tgcctaatat tttcatggga gaatggtctc c                              41

<210> SEQ ID NO 19
<211> LENGTH: 37
<212> TYPE: DNA
<213> ORGANISM: Artificial Sequence
<220> FEATURE:
<223> OTHER INFORMATION: 4509HindIIIrv

<400> SEQUENCE: 19
ctgaacaagc ttttatgcga tcctcctgta ataaagc                                   37

<210> SEQ ID NO 20

```
<211> LENGTH: 21
<212> TYPE: DNA
<213> ORGANISM: Artificial Sequence
<220> FEATURE:
<223> OTHER INFORMATION: npsB_f

<400> SEQUENCE: 20
ctcgacgttt tatctctgct g                                          21

<210> SEQ ID NO 21
<211> LENGTH: 21
<212> TYPE: DNA
<213> ORGANISM: Artificial Sequence
<220> FEATURE:
<223> OTHER INFORMATION: npsB_r

<400> SEQUENCE: 21
ttcctgaagt atctgccctg c                                          21

<210> SEQ ID NO 22
<211> LENGTH: 45
<212> TYPE: DNA
<213> ORGANISM: Artificial Sequence
<220> FEATURE:
<223> OTHER INFORMATION: gapA_fwd

<400> SEQUENCE: 22
gttttcccag tcacgacgtt gtatgaagta tgactccact cacgg                45

<210> SEQ ID NO 23
<211> LENGTH: 46
<212> TYPE: DNA
<213> ORGANISM: Artificial Sequence
<220> FEATURE:
<223> OTHER INFORMATION: gapA_rev

<400> SEQUENCE: 23
ttgtgagcgg ataacaattt caacgccttt cattgcgcct tcggaa               46

<210> SEQ ID NO 24
<211> LENGTH: 21
<212> TYPE: DNA
<213> ORGANISM: Artificial Sequence
<220> FEATURE:
<223> OTHER INFORMATION: leupA

<400> SEQUENCE: 24
atgaagatag cgattcacaa c                                          21

<210> SEQ ID NO 25
<211> LENGTH: 20
<212> TYPE: DNA
<213> ORGANISM: Artificial Sequence
<220> FEATURE:
<223> OTHER INFORMATION: leupB_r

<400> SEQUENCE: 25
gcgtggtctt ttagctgttc                                            20

<210> SEQ ID NO 26
<211> LENGTH: 21
```

```
<212> TYPE: DNA
<213> ORGANISM: Artificial Sequence
<220> FEATURE:
<223> OTHER INFORMATION: leupD r

<400> SEQUENCE: 26
catatcggta aaacctgctc g                                          21
```